United States Patent
Plettenburg et al.

(10) Patent No.: US 8,399,482 B2
(45) Date of Patent: Mar. 19, 2013

(54) 6-SUBSTITUTED ISOQUINOLINES AND ISOQUINOLINONES

(75) Inventors: Oliver Plettenburg, Frankfurt am Main (DE); Katrin Lorenz, Frankfurt am Main (DE); Matthias Loehn, Frankfurt am Main (DE); John Weston, Frankfurt am Main (DE); Heinz-Werner Kleemann, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/970,376

(22) Filed: Dec. 16, 2010

(65) Prior Publication Data

US 2011/0190339 A1 Aug. 4, 2011

Related U.S. Application Data

(63) Continuation of application No. PCT/EP2009/004420, filed on Jun. 19, 2009.

(60) Provisional application No. 61/153,145, filed on Feb. 17, 2009.

(30) Foreign Application Priority Data

Jun. 24, 2008 (EP) ..................................... 08290605

(51) Int. Cl.
  A61K 31/4725 (2006.01)
  C07D 217/24 (2006.01)
  C07D 405/12 (2006.01)
(52) U.S. Cl. ......... 514/309; 514/307; 546/139; 546/141
(58) Field of Classification Search .................. None
See application file for complete search history.

(56) References Cited

U.S. PATENT DOCUMENTS

| | | | |
|---|---|---|---|
| 5,480,883 A | 1/1996 | Spada et al. | |
| 6,903,107 B1 | 6/2005 | Timmers et al. | |
| 7,217,722 B2 | 5/2007 | Takami et al. | |
| 7,618,985 B2 | 11/2009 | Ray et al. | |
| 2003/0220368 A1 | 11/2003 | Ozaki et al. | |
| 2004/0138286 A1 | 7/2004 | Imazaki et al. | |
| 2006/0079556 A1 | 4/2006 | Sher et al. | |
| 2007/0060595 A1 | 3/2007 | Yoshizawa et al. | |
| 2008/0045566 A1 | 2/2008 | Ray et al. | |
| 2008/0242699 A1 | 10/2008 | Plettenburg et al. | |
| 2009/0088429 A1 | 4/2009 | Plettenburg et al. | |
| 2009/0093518 A1 | 4/2009 | Plettenburg et al. | |
| 2010/0056518 A1 | 3/2010 | Plettenburg et al. | |
| 2010/0056553 A1 | 3/2010 | Plettenburg et al. | |
| 2010/0056566 A1 | 3/2010 | Plettenburg et al. | |
| 2010/0056568 A1 | 3/2010 | Plettenburg et al. | |
| 2010/0063025 A1 | 3/2010 | Plettenburg et al. | |
| 2010/0081671 A1 | 4/2010 | Plettenburg et al. | |
| 2010/0105650 A1 | 4/2010 | Plettenburg et al. | |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087629 A | 4/1998 |
| WO | 9202476 | 2/1992 |
| WO | 9706802 | 2/1997 |
| WO | 9723214 | 7/1997 |
| WO | WO98/06433 | 2/1998 |
| WO | 9911642 | 3/1999 |
| WO | 0024718 | 5/2000 |
| WO | 0073299 | 12/2000 |
| WO | WO01/39726 A2 | 6/2001 |
| WO | 0153288 | 7/2001 |
| WO | 0156988 | 8/2001 |
| WO | 0164656 | 9/2001 |
| WO | WO01/64238 A2 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | WO03/053330 A2 | 7/2003 |
| WO | 2004113297 | 12/2004 |
| WO | WO2004/106325 A1 | 12/2004 |
| WO | 2005035933 | 2/2005 |
| WO | 2005035516 | 4/2005 |
| WO | WO2005/030130 A2 | 4/2005 |
| WO | WO2005/030791 A2 | 4/2005 |
| WO | 2005054202 | 6/2005 |
| WO | 2005074535 | 8/2005 |

(Continued)

OTHER PUBLICATIONS

International Preliminary Report on Patentability dated Jan. 5, 2011.
Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.
Takami, A. et al., "Design and Synthesis of Rho Kinase Inhibitors (I)" Bioorganic & Medicinal Chemistry (2004) pp. 2115-2137, vol. 12.
Iwakubo, M. et al., "Design and Synthesis of Rho Kinase Inhibitors (III)" Bioorganic & Medicinal Chemistry (2007) pp. 1022-1033, vol. 15.

(Continued)

*Primary Examiner* — Zinna Northington Davis
(74) *Attorney, Agent, or Firm* — Scully, Scott, Murphy & Presser, P.C.

(57) ABSTRACT

The invention relates to 6-substituted isoquinoline and isoquinolinone derivatives of the formula (I) useful for the treatment and/or prevention of diseases associated with Rho-kinase and/or Rho-kinase mediated phosphorylation of myosin light chain phosphatase, and compositions containing such compounds.

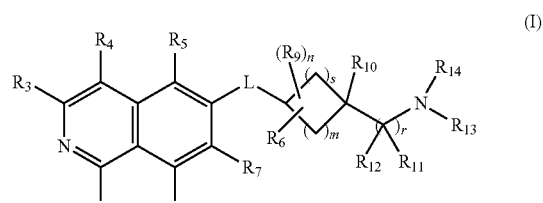

46 Claims, No Drawings

FOREIGN PATENT DOCUMENTS

| WO | 2005087226 | | 9/2005 |
|---|---|---|---|
| WO | 2005095362 | | 10/2005 |
| WO | WO2007/012421 | A1 | 2/2007 |
| WO | WO2007/012422 | A1 | 2/2007 |
| WO | 2007039563 | A1 | 4/2007 |
| WO | 2007065916 | | 6/2007 |
| WO | 2008020081 | | 2/2008 |
| WO | WO2008/020081 | A1 | 2/2008 |
| WO | 2008077555 | A2 | 7/2008 |
| WO | 2008077556 | A1 | 7/2008 |

OTHER PUBLICATIONS

Iwakubo, M. et al., "Design and Synthesis of Rho Kinase Inhibitors (II)" Bioorganic & Medicinal Chemistry (2007) pp. 350-364, vol. 15.

Tamura, M. et al., "Development of Specific Rho-Kinase Inhibitors and Their Clinical Application" Biochimicia et Biophysica Acta (2005) pp. 245-252, vol. 1754.

Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.

Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.

Caron, S. et al., "The Synthesis of a Selective PDE4/TNFα Inhibitor" Organic Process Research and Development (2001) pp. 587-592, vol. 5.

U.S. Appl. No. 13/000,754, filed Apr. 20, 2011, Inventor: Plettenburg et al., entitled: "Substituted Isoquinolines and Isoquinolinones as Rho Kinase Inhibitors".

U.S. Appl. No. 13/000,202, filed Dec. 20, 2010, Inventor: Plettenburg et al., entitled: "Bi- and Polycyclic Substituted Isoquinoline and Isoquinolinone Derivatives".

Alvarez, M. et al., "Product Class 6: Isoquinolinones," Science of Synthesis (2005), vol. 15, pp. 839-906.

Alvarez, M. et al., "Product Class 5: Isoquinolinones," Science of Synthesis (2005), vol. 15, pp. 661-838.

Ai, Shingo et al., "Rho-Rho kinase is involved in smooth muscle cell migration through myosin light chain phosphorylation-dependent and independent pathways," Atherosclerosis (2001), vol. 155, pp. 321-327.

Bauer, Marcus et al., "Dichotomous Regulation of Myosin Phosphorylation and Shape Change by Rho-Kinase and Calcium in Intact Human Platelets," Blood (1999), vol. 94, pp. 1665-1672.

Becker, Daniel P. et al., "A Short Synthesis of 1-Azaadamantan-4-one and the 4r and 4s Isomers of 4-Amino-1-azaadamantane," Synthesis (1992), vol. 11, pp. 1080-1082.

Chellaiah, Meenakshi A. et al., "Rho-dependent Rho kinase activation increases CD44 surface expression and bone resorption in osteoclasts," The Journal of Biological Chemistry (2003), vol. 278, pp. 29086-29097.

Chitaley, Kanchan et al., "Antagonism of Rho-kinase stimulates rat penile erection via a nitric oxide-independent pathway," Nature Medicine (2001), vol. 7, pp. 119-122.

Maruoka, Shuichiro et al., "Elastase Anti-elastase imbalance in the Pathogenesis of COPD," Nippon Rinsho (1999), vol. 57, p. 1982-1987.

Demiryürek, Ş eniz et al., "Effects of fasudil, a Rho-kinase inhibitor, on myocardial preconditioning in anesthetized rats," European Journal of Pharmacology (2005), vol. 527, pp. 129-140.

Retzer, Michaela et al., "Mildly oxidised low density lipoprotein induces platelet shape change via Rho-kinase-dependent phosphorylation of myosin light chain and moesin," FEBS Letters (2000), vol. 466, pp. 70-74.

Kimura, Kazushi et al., "Regulation of the Association of Adducin with Actin Filaments by Rho-associated Kinase (Rho-kinase) and Myosin Phosphatase," The Journal of Biological Chemistry (1998), vol. 273, pp. 5542-5548.

Fukumoto, Y. et al., "Acute vasodilator effects of a Rho-kinase inhibitor, fasudil, in patients with severe pulmonary hypertension," Heart (2005), vol. 91, pp. 391-392.

Gingras, Denis et al., "Tyrosine phosphorylation of the vascular endothelial-growth-factor receptor-2 (VEGFR-2) is modulated by Rho proteins," Biochemical Journal (2000), vol. 348, pp. 273-280.

Gokina, Natalia I. et al., "Effects of Rho kinase inhibition on cerebral artery myogenic tone and reactivity," Journal of Applied Physiology (2005), vol. 98, p. 1940-1948.

Okada, Hiroshi et al., "Synthesis and Antitumor Activities of Prodrugs of Benzoylphenylureas," Chemical and Pharmaceutical Bulletin (1994), vol. 42, pp. 57-61.

Yoshida, Yoshiki et al., "Studies on Anti-*Helicobacter pylori* Agents. Part 1: Benzyloxyisoquinoline Derivatives," Bioorganic and Medical Chemistry (1999), vol. 7, pp. 2647-2666.

Hara, Masahito et al., "Protein kinase inhibition by fasudil hydrochloride promotes neurological recovery after spinal cord injury in rats," Journal of Neurosurgery: Spine 1 (2000), vol. 93, pp. 94-101.

Hattori, Tsuyoshi et al., "Long-Term Inhibition of Rho-Kinase Suppresses Left Ventricular Remodeling After Myocardial Infarction in Mice," Circulation (2004), vol. 109, pp. 2234-2239.

Hitomi, Asako et al., "Hemorheological abnormalities in experimental cerebral ischemia and effects of protein kinase inhibitor on blood fluidity," Life Sciences (2000), vol. 67, pp. 1929-1939.

Honjo, Megumi et al., "Effects of Rho-Associated Protein Kinase Inhibitor Y-27632 on Intraocular Pressure and Outflow Facility," Investigative Ophthalmology and Visual Science (2001), vol. 42, pp. 137-144.

Inoue, Makoto et al., "Initiation of neuropathic pain requires lysophosphatidic acid receptor signaling," Nature Medicine (2004), vol. 10, pp. 712-718.

Itoh, Kazuyuki et al., "An essential part for Rho-associated kinase in the transcellular invasion of tumor cells," Nature Medicine (1999), vol. 5, pp. 221-225.

Kawaguchi, Atsuhiro et al., "The effect of a Rho kinase inhibitor Y-27632 on superoxide production, aggregation and adhesion in human polymorphonuclear leukocytes," European Journal of Pharmacology (2000), vol. 403, pp. 203-208.

Kim, Inkyeom et al., "Thin and Thick Filament Regulation of Contractility in Experimental Cerebral Vasospasm," Neurosurgery (2000), vol. 46, pp. 440-447.

Amano, Mutsuki et al., "Formation of Actin Stress Fibers and Focal Adhesions Enhanced by Rho-Kinase," Science (1997), vol. 275, pp. 1308-1311.

Kishi, Takuya et al., "Rho-Kinase Inhibitor Improves Increased Vascular Resistance and Impaired Vasodilation of the Forearm in Patients with Heart Failure," Circulation (2005), vol. 111, pp. 2741-2747.

Klages, Birgit et al., "Activation of $G_{12}/G_{13}$ Results in Shape Change and Rho/Rho-Kinase-mediated Myosin Light Chain Phosphorylation in Mouse Platelets," The Journal of Cell Biology (1999), vol. 144, pp. 745-754.

Noma, Kensuke et al., "Physiological role of ROCKs in the cardiovascular system," American Journal of Physiology—Cell Physiology (2006), vol. 290, pp. C661-C668.

Lin, Tong et al., "Rho-ROCK-LIMK-Cofilin Pathway Regulates Shear Stress Activation of Sterol Regulatory Element Binding Proteins," Circulation Research (2003), vol. 92, pp. 1296-1304.

Furukawa, Noboru et al., "Role of Rho-kinase in regulation of insulin action and glucose homeostasis," Cell Metabolism (2005), vol. 2, pp. 119-129.

Masumoto, Akihiro et al., "Suppression of Coronary Artery Spasm by the Rho-Kinase Inhibitor Fasudil in Patients With Vasospastic Angina," Circulation (2002), vol. 105, pp. 1545-1547.

Nakahara, Tsutomu et al., "Y-27632 potentiates relaxant effects of $β_2$-adrenoceptor agonists in bovine tracheal smooth muscle," European Journal of Pharmacology (2000), vol. 389, pp. 103-106.

Negoro, Nobuyuki et al., "The Kinase Inhibitor Fasudil (HA-1077) Reduces Intimal Hyperplasia through Inhibiting Migration and Enhancing Cell Loss of Vascular Smooth Muscle Cells," Biochemical and Biophysical Research Communications (1999), vol. 262, pp. 211-215.

Uchida, Shigeki et al., "The Suppression of Small GTPase Rho Signal Transduction Pathway Inhibits Angiogenesis in Vitro and in Vivo," Biochemical and Biophysical Research Communications (2000), vol. 269, pp. 633-640.

Pacaud, P. et al., "Rho proteins and vascular diseases," Archives des Maladies du Coeur et des Vaisseaux (2005), vol. 98, pp. 249-254.

Pommereau, Antje et al., "Two Simple and Generic Antibody-Independent Kinase Assays: Comparison of a Bioluminescent and a Microfluidic Assay Format," Journal of Biomolecular Screening (2004), vol. 9, pp. 409-416.

Remington's Pharmaceutical Sciences 17$^{th}$ Edition (1985), p. 1418.

Retzer, Michaela et al., "Lysophosphatidic acid-induced platelet shape change proceeds via Rho/Rho kinase-mediated myosin light-chain and moesin phosphorylation," Cell Signalling (2000), vol. 12, pp. 645-648.

Vicente-Manzanares, Miguel et al., "A Role for the Rho-p160 Rho Coiled-Coil Kinase Axis in the Chemokine Stromal Cell-Derived Factor-1α-Induced Lymphocyte Actomyosin and Microtubular Organization and Chemotaxis," The Journal of Immunology (2002), vol. 168, pp. 400-410.

Vicente-Manzanares, Miguel et al., "The RhoA Effector mDia is Induced During T Cell Activation and Regulates Actin Polymerization and Cell Migration in T Lymphocytes," The Journal of Immunology (2003), vol. 171, pp. 1023-1034.

Sandu, Oana A. et al., "Diabetes in the Goto-Kakizaki Rat is Accompanied by Impaired Insulin-Mediated Myosin-Bound Phosphatase Activation and Vascular Smooth Muscle Cell Relaxation," Diabetes (2000), vol. 49, pp. 2178-2189.

Sato, Motohiko et al., "Involvement of Rho-Kinase-Mediated Phosphorylation of Myosin Light Chain in Enhancement of Cerebral Vasospasm," Circulation Research (2000), vol. 87, pp. 195-200.

Satoh, Shin-Ichi et al., "Pharmacological profile of hydroxy fasudil as a selective rho kinase inhibitor on ischemic brain damage," Life Sciences (2001), vol. 69, pp. 1441-1453.

Setoguchi, Hidekazu et al., "Leukotriene $C_4$ enhances the contraction of porcine tracheal smooth muscle through the activation of Y-27632, a rho kinase inhibitor, sensitive pathway," British Journal of Pharmacology (2001), vol. 132, pp. 111-118.

Shimokawa, Hiroaki et al., "Anti-anginal Effect of Fasudil, a Rho-Kinase Inhibitor, in Patients With Stable Effort Angina: A Multicenter Study," Journal of Cardiovascular Pharmacology (2002), vol. 40, pp. 751-761.

Somlyo, Avril V. et al., "Rho-Kinase Inhibitor Retards Migration and in Vivo Dissemination of Human Prostate Cancer Cells," Biochemical and Biophysical Research Communications (2000), vol. 269, pp. 652-659.

Steioff, Kerstin et al., "Long term Rho-kinase inhibition ameliorates endothelial dysfunction in LDL-Receptor deficient mice," European Journal of Pharmacology (2005), vol. 512, pp. 247-249.

Seasholtz, Tammy M. et al., "Rho and Rho Kinase Mediate Thrombin-Stimulated Vascular Smooth Muscle Cell DNA Synthesis and Migration," Circulation Research (1999), vol. 84, pp. 1186-1193.

Tatsumi, S. et al., "Involvement of Rho-Kinase in Inflammatory and Neuropathic Pain Through Phosphorylation of Myristoylated Alanine-Rich C-Kinase Substrate (Marcks)," Neuroscience (2005), vol. 131, pp. 491-498.

Uehata, Masayoshi et al., "Calcium sensitization of smooth muscle mediated by a Rho-associated protein kinase in hypertension," Nature (1997), vol. 389, pp. 990-994.

Waiuno, Shu et al., "Therapeutic strategies targeting the Rho/Rho kinase pathway are a promising choice for the treatment of renal disease," Drug News and Perspectives (2005), vol. 18, pp. 639-643.

Yamakawa, Tadashi et al., "Involvement of Rho-Kinase in Angiotensin Ii-Induced Hypertrophy of Rat Vascular Smooth Muscle Cells," Hypertension (2000), vol. 35, pp. 313-318.

Yamamoto, Yasuhiro et al., "The Protein Kinase Inhibitor Fasudil Protects Against Ischemic Myocardial Injury Induced by Endothelin-1 in the Rabbit," Journal of Cardiovascular Pharmacology (2000), vol. 35, pp. 203-211.

Totsukawa, Go et al., "Distinct Roles of ROCK (Rho-kinase) and MLCK in Spatial Regulation of MLC Phosphorylation for Assembly of Stress Fibers and Focal Adhesions in 3T3 Fibroblasts," The Journal of Cell Biology (2000), vol. 150, pp. 797-806.

Yoshii, Akihiro et al., "Relaxation of Contracted Rabbit Tracheal and Human Bronchial Smooth Muscle by Y-27632 through Inhibition of $Ca^{2+}$ Sensitization," American Journal of Respiratory Cell and Molecular Biology (1999), vol. 20, pp. 1190-1200.

Zhou, Yan et al., "Nonsteroidal Anti-Inflammatory Drugs Can Lower Amyloidogenic $Aβ_{+2}$ by Inhibiting Rho," Science (2003), vol. 302, pp. 1215-1217.

Curran, T.T. et al., "The Preparation of Optically Active 2-Cyclopenten-1,4-Biol Derivatives from Furfuryl Alcohol" Tetrahedron, pp. 1983-2004, vol. 53(6), Feb. 2007.

6-SUBSTITUTED ISOQUINOLINES AND ISOQUINOLINONES

CROSS-REFERENCE TO RELATED APPLICATIONS

This application is a continuation application of International Patent Application No. PCT/EP2009/004420 filed on Jun. 19, 2009, claiming priority of European Application No. 08290605.8 filed Jun. 24, 2008 and claiming the benefit of U.S. Provisional Application No. 61/153,145 filed on Feb. 17, 2009.

The present invention relates to novel isoquinoline and isoquinolinone derivatives, their preparation and their use in the treatment and/or prevention of diseases related to the inhibition of Rho-kinase and/or of Rho-kinase mediated phosphorylation of myosin light chain phosphatase.

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al. Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-1948), bronchial smooth muscle contraction (Yoshii et al. Am. J. Resp. Cell Mol. Biol. 1999, 20, 1190-1200), asthma (Setoguchi et al. Br. J. Pharmacol. 2001, 132, 111-118; Nakahara et al. Eur. J. Pharmac, 2000, 389, 103-106) and chronic obstructive pulmonary disease (COPD, Maruoka et al. Nippon Rinsho, 1999, 57, 1982-1987), hypertension, pulmonary hypertension (Fukumoto et al. Heart 2005, 91, 391-392, Mukai et al. Nature 1997, 389, 990-994) and ocular hypertension and regulation of intraoccular pressure (Honjo et al. Invest. Ophthalmol. Visual Sci. 2001, 42, 137-144), endothelial dysfunction (Steioff et al. Eur. J. Pharmacol. 2005, 512, 247-249), angina (Masumoto et al. Circulation 2002, 105, 1545-47, Shimokawa et al. J. Cardiovasc. Pharmacol. 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-643), myocardial infarction (Demiryurek et al. Eur. J. Pharmacol. 2005, 527, 129-140, Hattori et al. Circulation 2004, 109, 2234-2239), cardiac hypertrophy and failure (Yamakawa et al. Hypertension 2000, 35, 313-318; Liao et al. Am. J. Physiol. Cell Physiol, 2006, 290, C661-668; Kishi et al. Circulation 2005, 111, 2741-2747), coronary heart disease, artherosclerosis, restenosis (Pacaud et al. Arch. Mal. Coeur 2005, 98, 249-254; Retzer et al. FEBS Lett. 2000, 466, 70-74; Negoro et al. Biochem. Biophys. Res. Commun. 1999, 262, 211-215), diabetes, diabetic complications, glucose utilization and metabolic syndrome (Sandu et al. Diabetes 2000, 49, 2178-2189; Maeda et al. Cell Metab. 2005, 2, 119-129), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Hara et al. J. Neurosurg. 2000, 93, 94-101), cerebral ischemia (Uehara et al. Nature 1997, 389, 990-994; Satoh et al. Life Sci. 2001, 69, 1441-1453; Hitomi et al. Life Sci. 2000, 67, 1929-1939; Yamamoto et al. J. Cardiovasc. Pharmacol. 2000, 35, 203-211), cerebral vasospasm (Sato et al. Circ. Res. 2000, 87, 195-200; Kim et al. Neurosurgery 2000, 46, 440-447), pain, e.g. neuropathic pain (Tatsumi et al. Neuroscience 2005, 131, 491-498; Inoue et al. Nature medicine 2004, 10, 712-718), infection of digestive tracts with bacteria (WO 98/06433), cancer development and progression, neoplasia where inhibition of Rho kinase has been shown to inhibit tumor cell growth and metastasis (Itoh et al. Nature Medicine 1999, 5, 221-225; Somlyo et al. Biochem. Biophys. Res. Commun. 2000, 269, 652-659), angiogenesis (Uchida et al. Biochem. Biophys. Res. Commun. 2000, 269, 633-640; Gingras et al. Biochem. J. 2000, 348, 273-280), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa et al. FEBS Lett. 2000, 466, 70-74; Bauer et al. Blood 1999, 94, 1665-1672; Klages et al. J. Cell Biol. 1999, 144, 745-754; Retzer et al. Cell Signal 2000, 12, 645-648) and leukocyte aggregation (Kawaguchi et al. Eur. J. Pharmacol. 2000, 403, 203-208; Sanchez-Madrid et al. J. Immunol. 2003, 171, 1023-1034; Sanchez-Madrid, et al. J. Immunol. 2002, 168, 400-410), stem cell and induced pluripotent stem cell related biology, e.g. cell-cell interaction, proliferation, cell cycle progression, gene regulation, migration, actin cytoskeleton modulation, and related application, e.g. as viability, survival, recovery, growth, susceptibility toward apoptosis, differentiation, development, gene modulation, modulation of morphogenesis, hosting and invasion (Krawetz et al. BioEssay 2009, 31, 336-343; Claassen et al. Mol. Reprod. Dev. 2009, PMID: 19235204; Heng Tissue Cell 2009, PMID: 19261317; Arnsdorf et al. J. Cell. Sci. 2009, 122, 546-553, Kim et al. Stem Cells 2009, 27, 191-199), modulation of epithelial-mesenchymal transition (Royal et al. Mol. Biol. Cell 2000, 11, 1709-1725; Zondag et al. J. Cell Biol. 2000, 149, 775-782; Masszi et al. Am. J. Physiol. Renal. Physiol. 2003, 284, 911-924; Smallhorn et al. Development 2004, 131, 2641-2651; Wells et al. Cell Motil. Cytoskeleton 2005, 62, 180-194; Wu et al. Cancer Res. 2006, 66, 9527-9534; Fan et al. Mol Biol Cell. 2007, 18, 1083-1097; Cho et al. Cell Biol. Int. 2007, 31, 1225-1230; Giehl et al. Cells Tissues Organs. 2007, 185, 123-130; Rodrigues-Diez et al. Pharm. Res. 2008, 25, 2447-2461), and bone resorption (Chellaiah et al. J. Biol. Chem. 2003, 278, 29086-29097), Na/H exchange transport system activation (Kawaguchi et al. Eur. J. Pharmacol, 2000, 403, 203-208), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res. 2003, 92, 1296-304).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

Moreover, a compound having inhibitory effect on Rho-kinase may be also be useful in curative approaches associated with stem cell or induced pluripotent stem cell treatment, improvement of recognition or for the treatment or prevention of fibroid heart, depression, epilepsy, renal papillary necrosis, tubulo-interstitial dysfunction, multiple sclerosis, vessel stenosis for example carotid stenosis or lipid disorders.

WO 2001/64238 describes isoquinoline-5-sulfonamide derivatives optionally substituted by a —$(CH_2)_{1-6}$—O—$(CH_2)_{0-6}$—, a —$(CH_2)_{0-6}$—S—$(CH_2)_{0-6}$— or a —$(CH_2)_{0-6}$— linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes —O—$(C_0-C_{10})$ alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—$[(C_1-C_6)$alkylene)$]_{0-1}$-Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I—X—Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$ alkyl etc.; or $R^{43}$ is a group $R^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxy in the 1-position and are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$alkyl etc.; or $R^{43}$ is a group $R^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO2003/053330 (Ube) generically describes isoquinolone derivatives of the formula

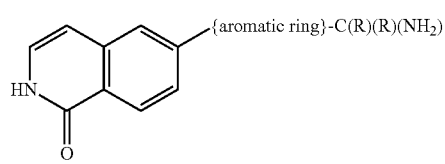

as Rho-kinase inhibitors.

WO 2007/012422 (Sanofi-Aventis) generically describes isoquinoline and isoquinolone derivatives of the formula

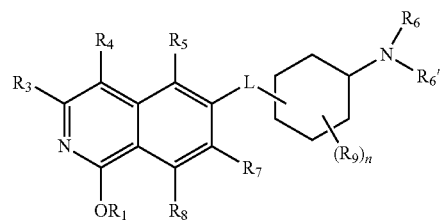

as Rho-Kinase inhibitors.

WO 2008/020081 (Organon) describes 6-substituted isoquinoline derivatives as Rho-kinase inhibitors.

In particular selectivity against other kinases has been identified as prerequisite for usage of kinase inhibitors as therapeutic agents. Fasudil for instance, a broadly profiled inhibitor of Rho kinase displays only modest selectivity against several other kinases, for example Protein Kinase A and Protein Kinase G (see for example Tamura et al., Biochimica et Biophysica Acta, Proteins and Proteomics (2005), 1754(1-2), 245-252. Also another Rho kinase inhibitor, Y-27632 only displays a 20-fold selectivity against Protein Kinase G.

Therefore, although several Rho-kinase inhibitors have been described there still remains the need for additional compounds useful in the treatment of Rho-kinase mediated diseases, in particular with improved selectivity.

An embodiment of the present invention is a compound of the formula (I)

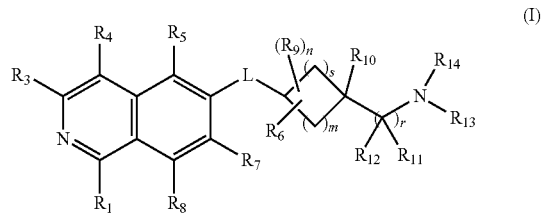

wherein $R_1$ is H, OH or $NH_2$;

$R_3$ is H, halogen, CN, $(C_1-C_6)$alkyl, OH, $NH_2$, or NHR';

$R_4$ is H, halogen, hydroxy, CN, $(C_1-C_6)$alkyl, R', or $(C_1-C_6)$alkylene-R';

$R_5$ is H, halogen, CN, $(C_1-C_6)$alkyl, or R';

$R_7$ is H, halogen, CN, $(C_1-C_6)$alkyl, O—$(C_1-C_6)$alkyl, R', or $SO_2$—$NH_2$;

$R_8$ is H, halogen or $(C_1-C_6)$alkyl;

$R_9$ is

R',

OH, halogen, $(C_1-C_6)$alkyl,

O—$(C_1-C_6)$alkyl, $(C_1-C_6)$alkylene-R', $(C_2-C_6)$alkenyl, $(C_2-C_6)$alkynyl, $(C_1-C_6)$alkylene-O—R', $(C_1-C_6)$alkylene-CH[R']$_2$, $(C_1-C_6)$alkylene-C(O)—R', $(C_1-C_6)$alkylene-C(O)$NH_2$, $(C_1-C_6)$alkylene-C(O)NH—R', $(C_1-C_6)$alkylene-C(O)NH—$(C_1-C_6)$alkyl, $(C_1-C_6)$alkylene-C(O)N[$(C_1-C_6)$alkyl]$_2$, $(C_1-C_6)$alkylene-C(O)N[R']$_2$;

$(C_1-C_6)$alkylene-C(O)O—$(C_1-C_6)$alkyl,

COOH,

C(O)O—$(C_1-C_6)$alkyl,

C(O)OR'

C(O)$(C_1-C_6)$alkyl,

C(O)R',

C(O)$NH_2$,

C(O)—NH—$(C_7-C_6)$alkenyl,

C(O)—NH—$(C_2-C_6)$alkynyl,

C(O)NH—$(C_1-C_6)$alkyl,

C(O)NHR',

C(O)—NH$(C_1-C_6)$alkylene-R',

C(O)N[$(C_1-C_6)$alkyl]R'

C(O)N[$(C_1-C_6)$alkyl]$_2$,

C(O)—$(C_1-C_6)$alkylene-R', or

C(O)O$(C_1-C_6)$alkylene-R';

$R_6$ is absent;

or is one $(C_1-C_4)$alkylene bound to the cycloalkyl ring, in which the $(C_1-C_4)$alkylene forms a second bond to a different carbon atom of the cycloalkyl ring to form a bicyclic ring system, wherein in the bicyclic ring system optionally one or two carbon atomes are replaced by a group independently selected from O, S, SO or $SO_2$;

or, if m and s are 2, m is 3 and s is 1, or m is 4 and s is 0, $R_6$ is $CH_2$—CH—$(CH_2)_2$ which is bound with one $CH_2$ to the cycloalkyl ring and the two other $CH_2$ are bound to different carbon atoms of the cycloalkyl ring; and, if m is 3 and s is 3, $R_6$ are two methylene groups bound to different carbon atoms of the cycloalkyl ring, wherein the methylene groups or the $CH_2$—CH—$(CH_2)_2$ group are bound to carbon atoms of the cycloalkyl ring such that they form an adamantane system of the formula

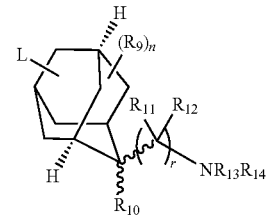

wherein L can be bound to any secondary or tertiary carbon atom and wherein the bicyclic ring system or adamantane system is unsubstituted or optionally substituted by $R_9$;

$R_{10}$ is $(C_1-C_6)$alkyl, $(C_1-C_8)$heteroalkyl, $(C_3-C_8)$cycloalkyl, $(C_3-C_8)$heterocycloalkyl, $(C_1-C_6)$alkylene-$(C_3-C_8)$cycloalkyl, $(C_1-C_6)$alkylene-$(C_6-C_{10})$aryl, $(C_1-C_6)$alkylene-$(C_5-C_{10})$heteroaryl, $(C_1-C_6)$alkylene-$(C_3-C_8)$heterocycloalkyl, C(O)NH—$(C_1-C_6)$alkyl, C(O)N[$C_1-C_6)$alkyl]$_2$,

C(O)NH—R',

C(O)N—(($C_1-C_6)$alkyl)-R', or

C(O)NH—$(C_1-C_6)$alkylene-R';

$R_{11}$ is

H, $(C_1-C_6)$alkyl, $(C_1-C_6)$alkylene-R'

R', or $R_{11}$ and $R_{12}$ together with carbon atom to which they are attached form a $(C_3-C_8)$cycloalkyl or a $(C_3-C_8)$-heterocycloalkyl ring;

$R_{12}$ is $(C_1-C_6)$alkyl, $(C_3-C_5)$cycloalkyl, $(C_5-C_{10})$heteroaryl, $(C_3-C_8)$heterocycloalkyl, or $(C_6-C_{10})$aryl;

or $R_{12}$ is H, provided that r=2 and the other $R_{12}$ is not H;

or $R_{11}$ and $R_{12}$ together with carbon atom to which they are attached form a $(C_3-C_8)$cycloalkyl or a $(C_3-C_8)$-heterocycloalkyl ring;

$R_{13}$ and $R_{14}$ are independently of each other

H,

R', $(C_1-C_6)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)—R', $(C_1-C_6)$alkylene-C(O)$NH_2$, $(C_1-C_6)$alkylene-C(O)NH—R', $(C_1-C_6)$alkylene-C(O)NH—$(C_1-C_6)$alkyl, $(C_1-C_6)$alkylene-C(O)N[$C_1-C_6)$alkyl]$_2$, $(C_1-C_6)$alkylene-C(O)N[R]$_2$, $(C_1-C_6)$alkylene-C(O)O—$(C_1-C_6)$alkyl, C(O)O—$(C_1-C_6)$alkyl,

C(O)OR',

C(O)$(C_1-C_6)$alkyl,

C(O)R',

C(O)NH—$(C_1-C_6)$alkyl,

C(O)NHR',

C(O)N[(C$_1$-C$_6$)alkyl]R',
C(O)N[(C$_1$-C$_6$)alkyl]$_2$,
C(O)—(C$_1$-C$_6$)alkylene-R',
R$_{13}$O(C$_1$-C$_6$)alkylene-R', or
R$_{13}$ and R$_{14}$, together with the N-atom to which they are attached, form a (C$_3$-C$_8$) heterocycloalkyl;
R$_{15}$ is H or (C$_1$-C$_6$)alkyl;
n is 0, 1, 2, 3 or 4;
m is 1, 2, 3 or 4;
s is 0, 1, 2, or 3;
r is 1 or 2;
L is O(CH$_2$)p, S(CH$_2$)p, S(O)(CH$_2$)p, SO$_2$(CH$_2$)p, NH(CH$_2$)p, N(C$_1$-C$_6$)alkyl-(CH$_2$)p, N(C$_3$-C$_6$)cycloalkyl-(CH$_2$)p; or N[(C$_1$-C$_3$)alkylene-R']—(CH$_2$)p;
p is 0, 1, 2, 3 or 4;
R' is
(C$_3$-C$_8$)cycloalkyl,
(C$_5$-C$_{10}$)heteroaryl,
(C$_3$-C$_8$)heterocycloalkyl,
(C$_6$-C$_{10}$)aryl;
wherein in residues R$_3$ to R$_{15}$ alkyl or alkylene is unsubstituted or optionally substituted one or more times by OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues R$_3$ to R$_{15}$ cycloalkyl or heterocycloalkyl is unsubstituted or optionally substituted one or more times by (C$_1$-C$_6$)alkyl, halogen, OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues R$_3$ to R$_{15}$ alkyl or alkylene is unsubstituted or optionally substituted one or more times by halogen;
wherein in residues R$_3$ to R$_{15}$ (C$_6$-C$_{10}$)aryl and (C$_5$-C$_{10}$)heteroaryl are unsubstituted or optionally substituted one or more times by a group independently selected from halogen, OH, NO$_2$, N$_3$, CN, C(O)—(C$_1$-C$_6$)alkyl, C(O)—(C$_6$-C$_{10}$)aryl, C(O)OH, C(O)O(C$_1$-C$_6$)alkyl, C(O)NH$_2$, C(O)NH(C$_1$-C$_6$)alkyl, C(O)N[(C$_1$-C$_6$)alkyl]$_2$, (C$_3$-C$_8$)cycloalkyl, (C$_1$-C$_6$)alkyl, (C$_1$-C$_6$)alkylene-NH(C$_1$-C$_6$)alkyl, (C$_1$-C$_6$)alkylene-N[(C$_1$-C$_6$)alkyl]$_2$, (C$_2$-C$_6$)alkenyl, (C$_2$-C$_6$)alkynyl, O—(C$_1$-C$_6$)alkyl, O—C(O)—(C$_1$-C$_6$)alkyl, PO$_3$H$_2$, SO$_3$H, SO$_2$—NH$_2$, SO$_2$NH(C$_1$-C$_6$)alkyl, SO$_2$N[(C$_1$-C$_6$)alkyl]$_2$, S—(C$_1$-C$_6$)alkyl; SO—(C$_1$-C$_6$)alkyl, SO$_2$—(C$_1$-C$_6$)alkyl, SO$_2$—N=CH—N[(C$_1$-C$_6$)alkyl]$_2$, SF$_5$,
C(NH)(NH$_2$), NH$_2$, NH—(C$_1$-C$_6$)alkyl, N[(C$_1$-C$_6$)alkyl]$_2$, NH—C(O)—(C$_1$-C$_6$)alkyl, NH—C(O)O—(C$_1$-C$_6$)alkyl, NH—SO$_2$—(C$_1$-C$_6$)alkyl, NH—SO$_2$—(C$_6$-C$_{10}$)aryl, NH—SO$_2$—(C$_5$-C$_{10}$)heteroaryl, NH—SO$_2$—(C$_3$-C$_8$)heterocycloalkyl, N(C$_1$-C$_6$)alkyl-C(O)—(C$_1$-C$_6$)alkyl, N(C$_1$-C$_6$)alkyl-C(O)O—(C$_1$-C$_6$)alkyl, N(C$_1$-C$_6$)alkyl-C(O)—NH—(C$_1$-C$_6$)alkyl], (C$_6$-C$_{10}$)aryl, (C$_1$-C$_6$)alkylene-(C$_6$-C$_{10}$)aryl, O—(C$_6$-C$_{10}$)aryl, O—(C$_1$-C$_6$)alkylene-(C$_6$-C$_{10}$)aryl, (C$_5$-C$_{10}$)heteroaryl, (C$_3$-C$_8$)heterocycloalkyl, (C$_1$-C$_6$)alkylene-(C$_5$-C$_{10}$)heteroaryl, (C$_1$-C$_6$)alkylene-(C$_3$-C$_8$)heterocycloalkyl, O—(C$_1$-C$_6$)alkylene-(C$_5$-C$_{10}$)heteroaryl, O—(C$_1$-C$_6$)alkylene-(C$_3$-C$_8$)heterocycloalkyl, wherein said (C$_6$-C$_{10}$)aryl or (C$_5$-C$_{10}$)heteroaryl or (C$_3$-C$_8$)heterocycloalkyl or (C$_3$-C$_8$)cycloalkyl may be substituted one to three times by a group independently selected from halogen, OH, NO$_2$, CN, O—(C$_1$-C$_6$)alkyl, (C$_1$-C$_6$)alkyl, NH$_2$, NH(C$_1$-C$_6$)alkyl, N[(C$_1$-C$_6$)alkyl]$_2$, SO$_2$CH$_3$, C(O)OH, C(O)O—(C$_1$-C$_6$)alkyl, C(O)NH$_2$, (C$_1$-C$_6$)alkylene-O—(C$_1$-C$_6$)alkyl, (C$_1$-C$_6$)alkylene-O—(C$_6$-C$_{10}$)aryl, or O—(C$_1$-C$_6$)alkylene-(C$_6$-C$_{10}$)aryl;
or wherein (C$_6$-C$_{10}$)aryl is vicinally substituted by a O—(C$_1$-C$_4$)alkylene-O group whereby a 5-8-membered ring is formed together with the carbon atoms the oxygen atoms are attached to; and
wherein aryl substituents of (C$_6$-C$_{10}$)aryl, (C$_5$-C$_{10}$)heteroaryl, cycloalkyl or (C$_3$-C$_8$)heterocycloalkyl groups may not be further substituted by an aryl, heteroaryl, cycloalkyl or heterocycloalkyl containing group;
their stereoisomeric and/or tautomeric forms and/or their pharmaceutically acceptable salts.

In another embodiment the present invention also relates to a compound of formula (I) and/or its pharmaceutically acceptable salt for use as a medicament. It also relates to the use of at least one compound of formula (I) and/or a pharmaceutically acceptable salt thereof for the treatment and/or prevention of Rho-Kinase mediated diseases such as hypertension, pulmonary hypertension, ocular hypertension, retinopathy, glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy, infection of digestive tracts with bacteria, sepsis or cancer development and progression. The invention further relates to a medicament comprising an effective amount of at least one compound of formula (I) and/or a pharmacologically acceptable salt thereof. Another object of the present invention is a method of producing a compound of formula (I).

The term alkyl as used in (C$_1$-C$_2$)alkyl, (C$_1$-C$_4$)alkyl, or (C$_1$-C$_6$)alkyl and the corresponding alkylene substituents are understood as a hydrocarbon residue which can be linear, i.e. straight-chain, or branched and has 1, 2, 3, 4, 5, or 6 carbon atoms, respectively. This also applies if an alkyl group occurs as a substituent on another group, for example in an alkoxy group (O-alkyl), S-alkyl or a —O(C$_1$-C$_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may optionally be halogenated once or more, e.g. alkyl groups may be fluorinated, e.g. perfluorinated. Examples of halogenated alkyl groups are CH$_2$F, CHF$_2$, CF$_3$ and CH$_2$CF$_3$, OCF$_3$, SCF$_3$, or —O—(CF$_2$)$_2$—O—.

The term (C$_2$-C$_6$)-alkenyl means a hydrocarbon residue whose carbon chain is straight-chain or branched and comprises 2 to 6 carbon atoms and has, depending on the chain length, 1, 2 or 3 double bonds, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. The double bond may where possible have the E or Z orientation. The double bonds may be both internal and terminal.

(C$_2$-C$_6$)-alkynyl groups are hydrocarbon residues whose carbon chain is straight-chain or branched and comprises 2 to 6 carbon atoms and have, depending on the chain length, 1 or 2 triple bonds, for example, ethynyl, 1-propynyl, 2-propynyl (=propargyl) or 2-butynyl. The triple bonds may be both internal and terminal.

Halogen means fluoro (F), chloro (Cl), bromo (Br) or iodo (I).

The term $(C_1-C_8)$heteroalkyl or the corresponding $(C_1-C_8)$ heteroalkylene substituents are understood as $(C_1-C_8)$alkyl or $(C_1-C_8)$alkylene groups wherein at least one carbon atom, preferably one or two carbon atoms, more preferred one carbon atom, is replaced by a group selected from O, NH, or S and wherein the nitrogen and sulfur atoms may optionally be oxidized. The heteroatom may be placed at any position of the alkyl or alkylene group. Examples of $(C_1-C_8)$heteroalkyl groups include —$CH_2$—O—$CH_3$, —$CH_2$—$CH_2$—O—$CH_2$—$CH_3$, —$CH_2$—NH—$CH_2$—$CH_3$, —$CH_2$—N($CH_2$—$CH_3$)$_2$—$CH_2$—$CH_2$—$CH_2$—O—$CH_3$, —$CH_2$—$CH_2$—$CH_2$—S—$CH_3$, —$CH_2$—O—CH($CH_3$)$_2$, —$CH_2$—O—$CH_2$—$CH_2$—O—$CH_3$ or O—$CH_2$—$CH_3$.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl, which can be bonded via any carbon atom.

A $(C_6-C_{10})$aryl group means an aromatic ring or a ring system which comprises two aromatic rings which are fused or otherwise linked or which comprises two fused aromatic rings wherein one ring is saturated or partly saturated, i.e contains at least one C—C single bond, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

$(C_3-C_8)$heterocycloalkyl group means a saturated (contains no double bonds) monocyclic carbon ring system containing 3, 4, 5, 6, 7 or 8 ring atoms in which one or more carbon atoms can be replaced by one or more heteroatoms such as, for example 1, 2 or 3 nitrogen atoms, 1 or 2 oxygen atoms, 1 or 2 sulfur atoms or combinations of different hetero atoms. The heterocycloalkyl residues can be bound at any positions, for example on the 1-position, 2-position, 3-position, 4-position, 5-position, 6-position, 7-position or 8-position. Also included are the corresponding N-oxides, sulfoxides or sulfones of these compounds.

Examples of $(C_3-C_8)$heterocycloalkyl groups—are oxiranyl, oxetanyl, aziridinyl, tetrahydrofuranyl, tetrahydropyranyl, dioxolanyl, for example 1,3-dioxolanyl, dioxanyl, for example 1,4-dioxanyl, piperidinyl, pyrrolidinyl, imidazolidinyl, triazolidinyl, hexahydropyrimidinyl, piperazinyl, triazinanyl, for example, 1,3,5-triazinanyl, 1,2,3-triazinanyl or 1,2,4-triazinanyl, tetrahydrothiophenyl, tetrahydro-thiopyranyl, dithiolanyl, for example 1,3-dithiolanyl, dithianyl, thiazolidinyl, oxazolidinyl, oxathiolanyl, for example 1,3-oxathiolanyl, morpholinyl or thiomorpholinyl, diazepanyl, for example 1,4-diazepanyl.

A preferred $(C_3-C_8)$heterocycloalkyl group is morpholinyl, pyrrolidinyl, piperazinyl, piperidinyl, oxetanyl or tetrahydropyranyl.

$(C_5-C_{10})$heteroaryl means a mono- or bicyclic ring system in which one or more carbon atoms can be replaced by one or more heteroatoms such as, for example 1, 2 or 4 nitrogen atoms, 1 or 2 oxygen atoms, 1 or 2 sulfur atoms or combinations of different hetero atoms. The heteroaryl residues can be bound at any position, for example on the 1-position, 2-position, 3-position, 4-position, 5-position, 6-position, 7-position or 8-position. $(C_5-C_{10})$heteroaryl groups may be an (1) aromatic monocyclic or bicyclic ring system or (2) a bicyclic ring system wherein one ring is aromatic and the second ring is at least partially saturated.

Also included are the corresponding N-oxides, sulfoxides or sulfones of these compounds.

Suitable $(C_5-C_{10})$heteroaryl groups are benzimidazolyl, benzofuryl, benzothienyl, azaindolyl, benzothiophenyl, benzoxazolyl, benzthiazolyl, benztriazolyl, benzisoxazolyl, benzisothiazolyl, carbolinyl, cinnolinyl, chromanyl, chromenyl, naphthyridinyl, phthalazinyl, pyridoimidazolyl, pteridinyl, purynyl, quinazolinyl, quinoxalinyl, quinolinyl, isoquinolinyl, tetrahydroisoquinolinyl, tetrahydroquinolinyl, indolinyl, indolizinyl, indolyl, furyl, furazanyl, thienyl, imidazolyl, imidazolinyl, 1H-indazolyl, pyrazolyl, oxazolyl, 1,2,3-oxadiazolyl, 1,2,4-oxadiazolyl, 1,2,5-oxadiazolyl, 1,3,4-oxadiazolyl, isoxazolyl, thiazolyl, isothiazolyl, pyridyl, triazolyl, pyrazinyl, pyrimidinyl, pyridazinyl, pyrazolinyl, pyrrolyl, 1,2,3-thiadiazolyl, 1,2,4-thiadiazolyl, 1,2,5-thiadiazolyl, 1,3,4-thiadiazolyl, tetrazolyl.

Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_5-C_{10})$heteroaryl residues can occur on free carbon atoms or on nitrogen atoms.

Preferred examples of $(C_5-C_{10})$heteroaryl residues are benzofuryl, quinolinyl, furyl, thienyl, imidazolyl, pyrazolyl, oxazolyl, isoxazolyl, thiazolyl, isothiazolyl, pyridyl, triazolyl, oxadiazolyl, pyrazinyl, pyrimidinyl, pyridazinyl and tetrazolyl.

A preferred $(C_5-C_{10})$heteroaryl is a $(C_5-C_6)$heteroaryl group. Preferred $(C_5-C_6)$heteroaryl residues are furyl, thienyl, imidazolyl, pyrazolyl, oxazolyl, isoxazolyl, thiazolyl, isothiazolyl, pyridyl, triazolyl, oxadiazolyl, pyrazinyl, pyrimidinyl, and pyridazinyl. Preferred examples of $(C_5-C_6)$heteroaryl residues are 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2- or -5-yl, 2-, 4- or 5-thiazolyl, 3-, 4- or 5-isothiazolyl, 2-, 3- or 4-pyridyl, 2-, 4-, 5- or 6-pyrimidinyl, 3- or 4-pyridazinyl, or pyrazinyl.

In residues $R_3$ to $R_{15}$ $(C_6-C_{10})$aryl and $(C_5-C_{10})$heteroaryl residues are unsubstituted or, if not specified otherwise, optionally substituted one or more times, preferably one to three times, by a group independently selected from halogen, OH, $NO_2$, $N_3$, CN, C(O)—$(C_1-C_6)$alkyl, C(O)—$(C_6-C_{10})$aryl, C(O)OH, C(O)O$(C_1-C_6)$alkyl, C(O)$NH_2$, C(O)NH$(C_1-C_6)$alkyl, C(O)N[$(C_1-C_6)$alkyl]$_2$, $(C_3-C_8)$cycloalkyl, $(C_1-C_6)$alkyl, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2$NH$(C_1-C_6)$alkyl, $SO_2$N[$(C_1-C_6)$alkyl]$_2$, S—$(C_1-C_6)$alkyl, SO—$(C_1-C_6)$alkyl, $SO_2$—$(C_1-C_6)$alkyl, $SO_2$—N=CH—N[$(C_1-C_6)$alkyl]$_2$, $SF_5$, C(NH)($NH_2$), $NH_2$, NH—$(C_1-C_6)$alkyl, N[$(C_1-C_6)$alkyl]$_2$, NH—C(O)—$(C_1-C_6)$alkyl, NH—C(O)O—$(C_1-C_6)$alkyl, NH—$SO_2$—$(C_1-C_6)$alkyl, NH—$SO_2$—$(C_6-C_{10})$aryl, NH—$SO_2$—$(C_5-C_{10})$heteroaryl, NH—$SO_2$—$(C_3-C_8)$heterocycloalkyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heteroaryl, $(C_3-C_8)$heterocycloalkyl, $(C_1-C_6)$alkylene-$(C_5-C_{10})$heteroaryl, $(C_1-C_6)$alkylene-$(C_3-C_8)$heterocycloalkyl, O—$(C_1-C_6)$alkylene-$(C_5-C_{10})$heteroaryl, O—$(C_1-C_6)$alkylene-$(C_3-C_8)$heterocycloalkyl, wherein said $(C_6-C_{10})$aryl or $(C_6-C_{10})$heteroaryl or $(C_3-C_8)$heterocycloalkyl or $(C_3-C_8)$cycloalkyl may be substituted one to three times by a group independently selected from halogen, OH, $NO_2$, CN, O—$(C_1-C_6)$alkyl, $(C_1-C_6)$alkyl, $NH_2$, NH$(C_1-C_6)$ alkyl, N[($C_1$-$C_6$)alkyl]$_2$, SO$_2$CH$_3$, C(O)OH, C(O)O—($C_1$-$C_6$)alkyl, C(O)NH$_2$, ($C_1$-$C_6$)alkylene-O—($C_1$-$C_6$)alkyl, ($C_1$-$C_6$)alkylene-O—($C_6$-$C_{10}$)aryl, or O—($C_1$-$C_6$)alkylene-($C_6$-$C_{10}$)aryl;

or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to;

and wherein aryl substituents of ($C_6$-$C_{10}$)aryl, ($C_5$-$C_{10}$)heteroaryl, cycloalkyl or ($C_3$-$C_8$)heterocycloalkyl groups may not be further substituted by an aryl, heteroaryl, cycloalkyl or heterocycloalkyl containing group.

Preferred substituents for ($C_6$-$C_{10}$)aryl and ($C_6$-$C_{10}$)heteroaryl groups are OH, ($C_1$-$C_4$)alkyl, O—($C_1$-$C_4$)alkyl, O-phenyl, phenyl, C(O)O—($C_1$-$C_6$)alkyl, C(O)OH, C(O)—($C_1$-$C_4$)alkyl, halogen, NO$_2$, SO$_2$NH$_2$, CN, SO$_2$—($C_1$-$C_4$)alkyl, SO$_2$—N=CH—N[($C_1$-$C_6$)alkyl]$_2$, NH—SO$_2$—($C_1$-$C_4$)alkyl, NH$_2$, NH—C(O)—($C_1$-$C_4$)alkyl, ($C_3$-$C_8$)cycloalkyl, ($C_1$-$C_4$)alkyl-OH, C(O)N[($C_1$-$C_4$)alkyl]$_2$, C(O)NH($C_1$-$C_6$)alkyl, C(O)NH$_2$, N[($C_1$-$C_4$)alkyl]$_2$, ($C_1$-$C_4$)alkylene-N[($C_1$-$C_4$)alkyl]$_2$, ($C_1$-$C_4$)alkylene-O—($C_1$-$C_4$)alkyl, ($C_5$-$C_6$)heteroaryl, ($C_3$-$C_8$)heterocycloalkyl, ($C_1$-$C_4$)alkylene-($C_6$-$C_{10}$)aryl, wherein the ($C_6$-$C_{10}$)aryl may be further substituted one to three times, preferably once, by halogen, ($C_1$-$C_4$)alkyl, O—($C_1$-$C_4$)alkyl, ($C_1$-$C_4$)alkylene-O—($C_1$-$C_6$)alkyl, ($C_6$-$C_{10}$)aryl, O—($C_1$-$C_6$)alkylene-($C_6$-$C_{10}$)aryl, or may be vicinally substituted by a O—($C_1$-$C_4$)alkylene-O group whereby a 5-8-membered ring is formed together with the carbon atoms the oxygen atoms are attached to.

More preferred substituents for ($C_6$-$C_{10}$)aryl and ($C_5$-$C_{10}$)heteroaryl are OH, halogen, CN, phenyl, O-phenyl, NH—C(O)—($C_1$-$C_4$)alkyl, C(O)—($C_1$-$C_4$)alkyl, C(O)—O($C_1$-$C_4$)alkyl, ($C_1$-$C_4$)alkyl, O—($C_1$-$C_4$)alkyl, CONH$_2$, SO$_2$—NH$_2$, SO$_2$—($C_1$-$C_4$)alkyl or SO$_2$—N=CH—N[($C_1$-$C_4$)alkyl]$_2$, ($C_1$-$C_4$)alkylene-phenyl, ($C_1$-$C_4$)alkylene-O—($C_1$-$C_4$)alkyl or ($C_5$-$C_6$)heteroaryl, wherein the phenyl is unsubstituted or optionally substituted one to three times, preferably once, by OH, halogen, ($C_1$-$C_4$)alkyl or O—($C_1$-$C_4$)alkyl.

Even more preferred substituents for ($C_6$-$C_{10}$)aryl and ($C_5$-$C_{10}$)heteroaryl are OH, halogen, CN, phenyl, O-phenyl, NH—C(O)—($C_1$-$C_4$)alkyl especially NH—C(O)—CH$_3$, C(O)—($C_1$-$C_4$)alkyl especially C(O)—CH$_3$, C(O)—O($C_1$-$C_4$)alkyl especially C(O)—OCH$_3$, ($C_1$-$C_4$)alkyl especially CH$_3$ or CF$_3$, O—($C_1$-$C_4$)alkyl especially O—CH$_3$, CONH$_2$, SO$_2^-$ NH$_2$, SO$_2$—($C_1$-$C_4$)alkyl especially SO$_2$—CH$_3$ or SO$_2$—CF$_3$; or SO$_2$—N=CH—N[($C_1$-$C_4$)alkyl]$_2$ especially SO$_2$—N=CH—N[(CH$_3$)$_2$,
wherein the phenyl is unsubstituted or optionally substituted one to three times, preferably once, by OH, halogen, ($C_1$-$C_4$)alkyl or O—($C_1$-$C_4$)alkyl.

More especially preferred substituents for ($C_6$-$C_{10}$)aryl and ($C_5$-$C_{10}$)heteroaryl groups are OH, CN, ($C_1$-$C_4$)alkyl especially CH$_3$ or CF$_3$, O($C_1$-$C_4$)alkyl especially O—CH$_3$, halogen or phenyl, wherein the phenyl may be further substituted one to three times, preferably once, by OH, halogen, ($C_1$-$C_4$)alkyl especially CH$_3$ or CF$_3$, or O—($C_1$-$C_4$)alkyl especially O—CH$_3$.

Most preferred substituents for ($C_6$-$C_{10}$)aryl and ($C_5$-$C_{10}$)heteroaryl groups are OH, CN, halogen, ($C_1$-$C_4$)alkyl especially CH$_3$ or CF$_3$, O($C_1$-$C_4$)alkyl especially O—CH$_3$, or halogen.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

In residues $R_3$ to $R_{15}$ an alkyl or alkylene is unsubstituted or, if not specified otherwise, optionally substituted one or more times by halogen. If substituted, alkyl or alkylene is preferably substituted one to three times by halogen selected from chloro or bromo but may be substituted by fluoro once or more, e.g. being perfluorinated. Preferably halogen is fluoro. Preferably alkylene is not halogenated. More preferred an alkyl or alkylene is not halogenated.

In residues $R_3$ to $R_{15}$ alkyl or alkylene is unsubstituted or, if not specified otherwise, optionally substituted one or more times by a group selected independently from OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$. If substituted, the number of substituents is preferably between 1, 2, 3 or 4, more preferably 1 or 2 with 1 being even more preferred. Preferably an alkylene is not substituted by one of these groups. More preferably an alkyl or alkylene is not substituted by one of these groups. Preferably alkyl or alkylene in $R_3$, $R_4$, $R_5$, $R_7$ and $R_8$ are not substituted. In a further embodiment alkyl or alkylene in $R_4$ to $R_{15}$ is not substituted by one of these groups.

In residues $R_3$ to $R_{15}$ cycloalkyl or heterocycloalkyl is unsubstituted or, if not specified otherwise, optionally substituted one or more times by ($C_1$-$C_6$)alkyl, halogen, OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$. If substituted, the number of substituents is preferably between 1, 2, 3 or 4, more preferably 1 or 2 with 1 being even more preferred. Preferably cycloalkyl or heterocycloalkyl in $R_3$ to $R_9$ are not substituted. In a further embodiment cycloalkyl or heterocycloalkyl in $R_3$ to $R_{15}$ are not substituted. In a preferred embodiment a heterocycloalkyl is not substituted. In another embodiment cycloalkyl is not substituted.

The general and preferred substituents of ($C_6$-$C_{10}$)aryl, ($C_5$-$C_{10}$)heteroaryl, ($C_3$-$C_8$)heterocycloalkyl and ($C_3$-$C_8$)cycloalkyl groups as defined before may be combined with the general and preferred definitions of $R_1$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, n, s, m, r, p and L as described in the following embodiments of a compound of formula (I).

The following embodiments of a compound of formula (I) do further characterize and are part of the present invention.

In one embodiment of a compound of formula (I) $R_1$ is H and the compound is characterized by the formula (II)

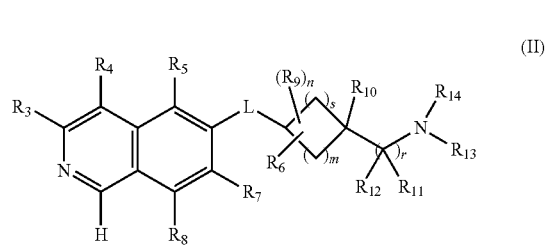

(II)

In another embodiment of the present invention $R_1$ is OH and the compound is characterized by the formula (IIIa)

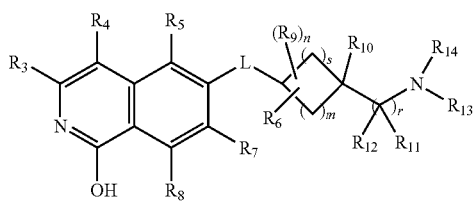
(IIIa)

The isoquinoline derivative of formula (I), wherein $R_1$ is OH, includes the corresponding tautomeric 1-isoquinolone derivative which is characterized by the formula (IIIb)

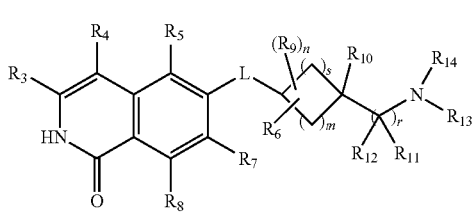
(IIIb)

This tautomeric form is also an embodiment of the present invention.

In a further embodiment $R_1$ is $NH_2$ and the compound is characterized by the formula (IV)

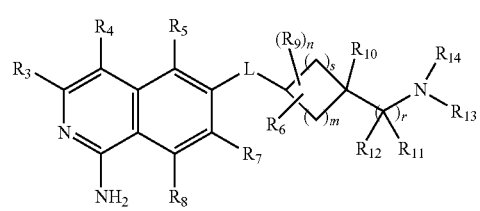
(IV)

The following further embodiments equally refer to the compounds of formula (I), (II), (IIIa), (IIIb) and (IV).

In a preferred embodiment $R_1$ is H or OH; more preferably $R_1$ is OH.

In one embodiment $R_3$ is preferably H, halogen, $(C_1\text{-}C_6)$alkyl, or NH—R'. In another more preferred embodiment $R_3$ is H, halogen, unsubstituted or substituted NH—$(C_5\text{-}C_6)$heteroaryl, unsubstituted or substituted NH—$(C_3\text{-}C_8)$heterocycloalkyl or unsubstituted or substituted NH-phenyl. In a even more preferred embodiment $R_3$ is unsubstituted or substituted NH—$(C_5\text{-}C_6)$heteroaryl containing one or more N atoms, or unsubstituted or substituted NH-phenyl. In a most preferred embodiment $R_3$ is H. Examples of NHR' substituents in $R_3$ are

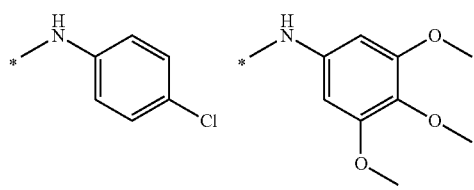

-continued

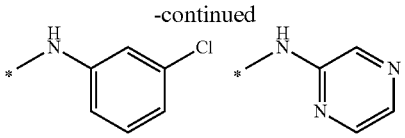

The asterisk (*) denotes where the bond is connected to the C-atom of the ring.

In a preferred embodiment $R_4$ is H, halogen, $(C_1\text{-}C_6)$alkyl, or $(C_1\text{-}C_2)$alkenyl-phenyl. In a more preferred embodiment $R_4$ is H, halogen or unsubstituted or substituted $(C_1\text{-}C_4)$alkyl or $(C_1\text{-}C_2)$alkenyl-phenyl, preferably unsubstituted $(C_1\text{-}C_4)$ alkyl or $(C_1\text{-}C_2)$alkenyl-phenyl. Most preferred $R_4$ is H.

In a preferred embodiment $R_5$ is H, CN, halogen, unsubstituted or substituted $(C_1\text{-}C_6)$alkyl, unsubstituted or substituted $(C_6\text{-}C_{10})$aryl, or unsubstituted or substituted $(C_5\text{-}C_{10})$ heteroaryl. Examples of $R_5$ are hydrogen, fluoro, chloro, bromo, iodo, methyl, ethyl, phenyl, thienyl or pyridyl, nitrile, (p-methoxy)-phenyl, N-aniline, cyclopropyl, tetrazol, 4-methoxy-aniline. In a more preferred embodiment $(C_1\text{-}C_6)$ alkyl, $(C_6\text{-}C_{10})$aryl or $(C_5\text{-}C_{10})$heteroaryl are unsubstituted. In an even more preferred embodiment $R_5$ is H, halogen, methyl, ethyl, phenyl, thienyl, or pyridyl, more specifically H, halogen, methyl, or ethyl. Most preferred $R_5$ is H.

In a preferred embodiment $R_7$ is H, halogen, nitrile, unsubstituted or substituted $(C_1\text{-}C_6)$alkyl, unsubstituted or substituted O—$(C_1\text{-}C_6)$alkyl, or unsubstituted or substituted R'. In a more preferred embodiment $R_7$ is H, halogen, nitrile, unsubstituted or substituted $(C_1\text{-}C_4)$alkyl, unsubstituted or substituted O—$(C_1\text{-}C_4)$alkyl, unsubstituted or substituted phenyl, unsubstituted or substituted $(C_5\text{-}C_6)$heteroaryl, or unsubstituted or substituted $(C_3\text{-}C_6)$cycloalkyl. Preferably, $(C_1\text{-}C_6)$ alkyl, phenyl or $(C_5\text{-}C_6)$heteroaryl are unsubstituted.

In an even more preferred embodiment $R_7$ is H, fluoro, chloro, bromo, methyl, ethyl, methoxy, phenyl, nitrile, cyclopropyl, or thienyl. More preferably $R_7$ is H, fluoro, chloro, bromo, methyl or methoxy, in particular H or chloro. Most preferred $R_7$ is chloro.

In a preferred embodiment $R_8$ is H, Cl, F, methyl or ethyl. In a more preferred embodiment $R_8$ is H.

In a preferred embodiment $R_9$ is R', OH, halogen, $(C_1\text{-}C_6)$ alkyl, $(C_1\text{-}C_6)$alkylene-R', $(C_2\text{-}C_6)$alkenyl, $(C_1\text{-}C_6)$alkylene-C(O)NH—R', $(C_1\text{-}C_6)$alkylene-C(O)NH—$(C_1\text{-}C_6)$alkyl, C(O)OH, C(O)$NH_2$, C(O)NH—$(C_1\text{-}C_6)$alkyl, C(O)NHR', C(O)—NH—$(C_1\text{-}C_8)$alkynyl, C(O)—NH($C_1\text{-}C_8$)alkylene-R', or C(O)N[$(C_1\text{-}C_8)$alkyl]$_2$; wherein alkyl, alkylene and R' are unsubstituted or substituted. In a more preferred embodiment $R_9$ is OH, halogen, $(C_1\text{-}C_6)$alkyl, $(C_1\text{-}C_6)$alkylene-R', $(C_2\text{-}C_6)$alkenyl, C(O)OH, C(O)$NH_2$, C(O)NH—$(C_1\text{-}C_8)$ alkyl, C(O)NHR', or C(O)N[$(C_1\text{-}C_6)$alkyl]$_2$, wherein alkyl, alkylene and R' are unsubstituted or substituted. More preferably $R_9$ is OH, halogen, $(C_1\text{-}C_6)$alkyl, C(O)OH, C(O)$NH_2$, or O—$CH_3$, wherein alkyl is unsubstituted or substituted. In an even more preferred embodiment $R_9$ is unsubstituted or substituted $(C_1\text{-}C_6)$alkyl, preferably $R_9$ is unsubstituted $(C_1\text{-}C_6)$alkyl.

$R_9$ may be bound to any carbon atom of the ring including the position where the linker group L is bound.

As examples for these embodiments, $R_9$ is methyl, ethyl, propyl, isopropyl,

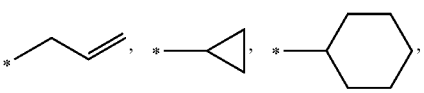

-continued

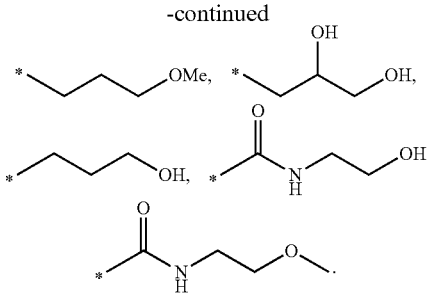

The asterisk (*) denotes where the bond is connected to the C-atom of the ring.

In a preferred embodiment $R_{10}$ is
$(C_1-C_6)$alkyl,
$(C_1-C_8)$heteroalkyl,
$(C_3-C_8)$cycloalkyl,
$(C_3-C_8)$heterocycloalkyl,
$(C_1-C_6)$alkylene-$(C_3-C_8)$cycloalkyl,
$(C_1-C_6)$alkylene-$(C_6-C_{10})$aryl,
$(C_1-C_6)$alkylene-$(C_5-C_{10})$heteroaryl,
$(C_1-C_6)$alkylene-$(C_3-C_8)$heterocycloalkyl,
C(O)NH—$(C_1-C_6)$alkyl,
C(O)NH—$(C_6-C_{10})$aryl, or
C(O)NH—$(C_1-C_6)$alkylene-$(C_6-C_{10})$aryl,
wherein $(C_1-C_6)$alkyl, $(C_1-C_8)$heteroalkyl, $(C_3-C_8)$cycloalkyl, $(C_3-C_8)$heterocycloalkyl, $(C_1-C_6)$alkylene, $(C_6-C_{10})$aryl, or $(C_5-C_{10})$heteroaryl are unsubstituted or substituted.

In a more preferred embodiment $R_{10}$ is
$(C_1-C_6)$alkyl,
$(C_1-C_8)$heteroalkyl,
$(C_3-C_8)$cycloalkyl,
$(C_3-C_8)$heterocycloalkyl,
$(C_1-C_6)$alkylene-$(C_3-C_8)$cycloalkyl,
$(C_1-C_6)$alkylene-$(C_6-C_{10})$aryl,
$(C_1-C_6)$alkylene-$(C_5-C_{10})$heteroaryl, or
$(C_1-C_6)$alkylene-$(C_3-C_8)$heterocycloalkyl,
wherein $(C_1-C_6)$alkyl, $(C_1-C_8)$heteroalkyl, $(C_3-C_8)$cycloalkyl, $(C_3-C_8)$heterocycloalkyl, $(C_1-C_6)$alkylene, $(C_6-C_{10})$aryl, or $(C_5-C_{10})$heteroaryl are unsubstituted or substituted.

In a particularly preferred embodiment $R_{10}$ is
$(C_1-C_6)$alkyl,
$(C_1-C_8)$heteroalkyl,
$(C_3-C_8)$cycloalkyl,
$(C_3-C_8)$heterocycloalkyl,
$(C_1-C_6)$alkylene-$(C_3-C_8)$cycloalkyl,
$(C_1-C_6)$alkylene-phenyl, or
$(C_1-C_6)$alkylene-$(C_5-C_6)$heteroaryl,
$(C_1-C_6)$alkylene-$(C_5-C_6)$heterocycloalkyl,
wherein $(C_1-C_6)$alkyl, $(C_1-C_8)$heteroalkyl, $(C_3-C_5)$cycloalkyl, $(C_3-C_8)$heterocycloalkyl, $(C_1-C_6)$alkylene, phenyl, or $(C_5-C_{10})$heteroaryl are unsubstituted or substituted.

In an even more preferred embodiment $R_{10}$ is
$(C_1-C_6)$alkyl,
$(C_1-C_8)$heteroalkyl,
$(C_3-C_8)$cycloalkyl,
$(C_3-C_8)$heterocycloalkyl,
$(C_1-C_6)$alkylene-$(C_3-C_8)$cycloalkyl,
$(C_1-C_2)$alkylene-phenyl,
$(C_1-C_6)$alkylene-$(C_5-C_6)$heterocycloalkyl, or
wherein $(C_1-C_6)$alkyl, $(C_1-C_8)$heteroalkyl, $(C_3-C_8)$cycloalkyl, $(C_3-C_8)$heterocycloalkyl, phenyl and $(C_8-C_{10})$heteroaryl are unsubstituted or substituted, preferably phenyl is unsubstituted or optionally substituted once or twice by a group selected independently of each other from halogen, $(C_1-C_4)$alkyl or O—$(C_1-C_4)$alkyl, wherein $(C_1-C_4)$alkyl may optionally be substituted by fluoro. In a particular embodiment $(C_1-C_6)$alkyl, $(C_1-C_8)$heteroalkyl, $(C_3-C_8)$cycloalkyl, $(C_3-C_8)$heterocycloalkyl, phenyl and $(C_5-C_{10})$heteroaryl are unsubstituted.

In an even more preferred embodiment $R_{10}$ is methyl, ethyl, propyl, isopropyl, butyl, isobutyl, cyclopropyl, cyclobutyl, cyclopentyl, cyclopropylmethylene, isopropyloxymethylene, tetrahydrofuranyl, tetrahydropyranyl or benzyl, cyclohexyl, trifluoromethyl, 3,3,3-trifluoropropyl, methoxy, ethoxy, ethoxymethyl, tetrahydropyranylmethylene, dioxo-tetrahydrothiopyranyl.

In a most preferred embodiment $R_{10}$ is methyl, ethyl, propyl, isopropyl, butyl, isobutyl, cyclopropyl, cyclobutyl, cyclopentyl, cyclopropylmethylene, isopropyloxymethylene, tetrahydrofuranyl, tetrahydropyranyl or benzyl.

In a preferred embodiment $R_{11}$ is
H,
$(C_1-C_6)$alkyl,
$(C_3-C_8)$cycloalkyl, or
$(C_5-C_6)$heteroaryl, preferably H or $(C_1-C_6)$alkyl, wherein $(C_1-C_6)$alkyl, $(C_3-C_8)$cycloalkyl, or $(C_5-C_{10})$heteroaryl are unsubstituted or substituted, preferably unsubstituted.

In a more preferred embodiment $R_{11}$ is H or $(C_1-C_6)$alkyl, wherein $(C_1-C_6)$alkyl is unsubstituted or substituted, preferably unsubstituted. Most preferably $R_{11}$ is H.

In a preferred embodiment $R_{12}$ is
$(C_1-C_6)$alkyl, wherein optionally one or more hydrogen are substituted by fluoro;
$(C_3-C_8)$cycloalkyl,
$(C_6-C_6)$heteroaryl, or
$(C_6-C_{10})$aryl, wherein $(C_3-C_8)$cycloalkyl, $(C_6-C_{10})$heteroaryl and $(C_6-C_{10})$aryl are unsubstituted or substituted, preferably $(C_3-C_5)$cycloalkyl, and $(C_5-C_6)$heteroaryl are unsubstituted. Preferably $(C_6-C_{10})$aryl is phenyl which is unsubstituted or optionally substituted once or twice by a group selected independently of each other from halogen, $(C_1-C_4)$alkyl or O—$(C_1-C_4)$alkyl, wherein $(C_1-C_4)$alkyl may optionally be substituted by fluoro.

In a preferred embodiment $R_{12}$ is methyl, ethyl, propyl, isopropyl, isobutyl, cyclopropyl, trifluoromethyl, pentafluoroethyl, thiazolyl or phenyl.

In a further embodiment $R_{11}$ and $R_{12}$, together with the carbon atom to which they are attached, form a $(C_3-C_8)$cycloalkyl ring, which is unsubstituted or substituted, preferably unsubstituted.

In a further embodiment $R_{11}$ and $R_{12}$, together with the carbon atom to which they are attached, form a $(C_3-C_8)$heterocycloalkyl ring, which is unsubstituted or substituted. Preferably the formed heterocyclyl group is oxetanyl, morpholinyl, piperidinyl, pyrrolidinyl or piperazinyl. More preferably the heterocyclyl group is morpholinyl or piperazinyl. The formed heterocycloalkyl group is preferably unsubstituted.

In one embodiment of a compound of formula (I) $R_{13}$ and $R_{14}$ are independently of each other
H,
R'
$(C_1-C_6)$alkyl,
$(C_1-C_6)$alkylene-R',
$(C_1-C_6)$alkylene-O—$(C_1-C_6)$alkyl,
$(C_1-C_6)$alkylene-O—R',
C(O)NH—$(C_1-C_6)$alkyl,
C(O)NHR',
$C(O)N[(C_1-C_6)alkyl]_2$, wherein R', ($C_1$-$C_6$)alkyl and ($C_1$-$C_6$)alkylene are unsubstituted or substituted.

In a further embodiment $R_{13}$ and $R_{14}$, together with the N-atom to which they are attached, form a ($C_3$-$C_8$)-heterocycloalkyl ring, which is unsubstituted or substituted. Preferably, a ($C_3$-$C_8$)-heterocycloalkyl is unsubstituted.

In a preferred embodiment of a compound of formula (I) $R_{13}$ and $R_{14}$ are independently of each other
H,
($C_1$-$C_6$)alkyl,
($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
($C_1$-$C_4$)alkylene-($C_6$-$C_{10}$)aryl,
($C_1$-$C_4$)alkylene-O—($C_1$-$C_6$)alkyl,
C(O)NH—($C_1$-$C_6$)alkyl, or
$R_{13}$ and $R_{14}$, together with the N-atom to which they are attached, form a ($C_3$-$C_8$) heterocycloalkyl group,
wherein ($C_1$-$C_6$)alkyl, ($C_3$-$C_8$)cycloalkyl, ($C_1$-$C_4$)alkylene, ($C_5$-$C_{10}$)heteroaryl, ($C_3$-$C_8$)heterocycloalkyl, ($C_6$-$C_{10}$)aryl are unsubstituted or substituted.

Preferably the formed heterocyclyl group in $R_{13}$ and $R_{14}$ is morpholinyl, piperidinyl, pyrrolidinyl or piperazinyl. More preferably the heterocyclyl group is morpholinyl or piperazinyl.

In a more preferred embodiment of a compound of formula (I) $R_{13}$ is H, ($C_1$-$C_6$)alkyl, ($C_3$-$C_8$)cycloalkyl, or ($C_1$-$C_4$)alkylene-($C_3$-$C_8$)cycloalkyl; and
$R_{14}$ is
H,
($C_1$-$C_6$)alkyl,
($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
$C_1$-$C_4$)alkylene-($C_6$-$C_{10}$)aryl,
($C_1$-$C_4$)alkylene-O—($C_1$-$C_6$)alkyl, or
C(O)NH—($C_1$-$C_6$)alkyl.
wherein ($C_1$-$C_6$)alkyl, ($C_3$-$C_8$)cycloalkyl, ($C_1$-$C_4$)alkylene, ($C_3$-$C_8$)heterocycloalkyl, ($C_6$-$C_{10}$)aryl are unsubstituted or substituted.

In an even more preferred embodiment of a compound of formula (I)
$R_{13}$ is H or ($C_1$-$C_6$)alkyl; and
$R_{14}$ is
H,
($C_1$-$C_6$)alkyl,
($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
($C_1$-$C_4$)alkylene-($C_6$-$C_{10}$)aryl, or
($C_1$-$C_4$)alkylene-O—($C_1$-$C_6$)alkyl.
wherein ($C_1$-$C_6$)alkyl, ($C_3$-$C_8$)cycloalkyl, ($C_1$-$C_4$)alkylene, ($C_3$-$C_8$)heterocycloalkyl, ($C_6$-$C_{10}$)aryl are unsubstituted or substituted.

More preferrably $R_{13}$ is H, ($C_1$-$C_6$)alkyl and
$R_{14}$ is H, ($C_1$-$C_6$)alkyl or ($C_3$-$C_8$)cycloalkyl, wherein ($C_1$-$C_6$) alkyl or ($C_3$-$C_8$)cycloalkyl are unsubstituted or substituted, preferably unsubstituted.

In a further embodiment $R_{13}$ is H and $R_{14}$ is H, ($C_1$-$C_6$) alkyl or ($C_3$-$C_3$)cycloalkyl wherein ($C_1$-$C_6$)alkyl or ($C_3$-$C_8$) cycloalkyl are unsubstituted.

Most preferred $R_{13}$ and $R_{14}$ are H.

As examples for the before mentioned embodiments, $R_{13}$ or $R_{14}$ are, independently from each other, hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of The asterisk (*) denotes where the bond is connected to the N-atom of the amine.

In one embodiment $R_{15}$ is H or ($C_1$-$C_6$)alkyl, which is unsubstituted or optionally substituted, more preferably $R_{15}$ is H or ($C_1$-$C_4$)alkyl, most preferably H. Preferably, the alkyl is unsubstituted.

In one embodiment of a compound of formula (I) $R_6$ is absent or the bicyclus or the adamantane formed with $R_6$ is selected from the group of -continued

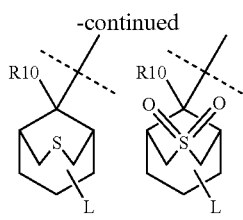

(the bond with the dotted line indicates the position of the —(CR$_{11}$R$_{12}$), NR$_{13}$R$_{14}$ residue)
or

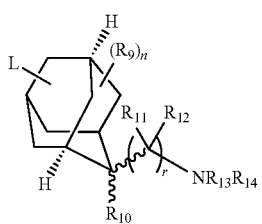

which is unsubstituted or optionally substituted by R$_9$. Preferably, the bicyclus or adamantane is unsubstituted (n is 0) or substituted once (n is 1)

Preferably the adamantane has the following structure

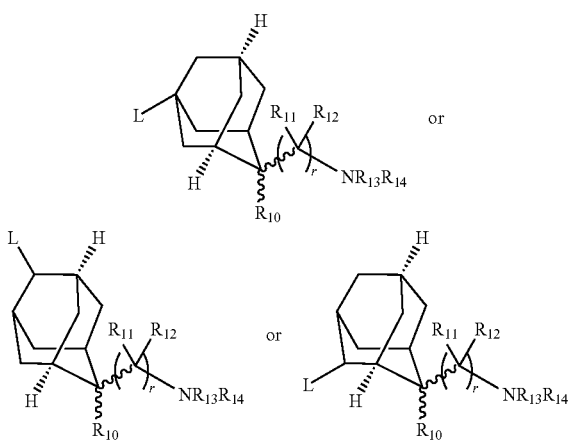

The cis and trans isomers in these adamantane residues such as for example in the structures

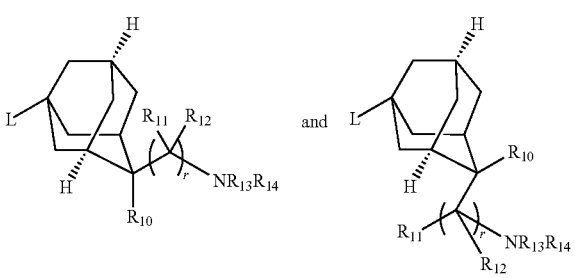

are included.

In one embodiment of a compound of formula (I) R$_6$ is absent, i.e. no bicyclus or adamantane is formed.

In one embodiment m is 2 and s is 2 resulting in a residue within a compound of formula (I) of the formula

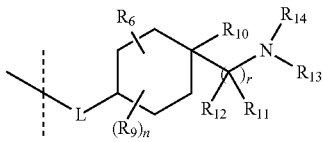

in all their stereochemical forms.

In another embodiment m is 3 and s is 1 resulting in a residue within a compound of formula (I) of the formula

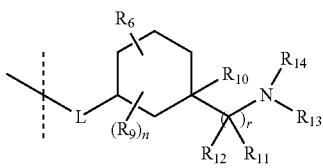

In a further embodiment m is 2 and s is 1. In still another embodiment m is 3 and a is 0. In yet another embodiment m is 4 and s is 0.

In one embodiment of a compound of formula (I) n is 0, 1, or 2. More preferred, n is 0 or 1. Most preferred n is 0.

In a preferred embodiment r is 1,

In another embodiment L is O(CH$_2$)p. In a further embodiment L is S(CH$_2$)p, S(O)(CH$_2$)p or SO$_2$(CH$_2$)p. In another embodiment L is NH(CH$_2$)p, N[(C$_1$-C$_6$)alkyl](CH$_2$)p, N[(C$_3$-C$_6$)cycloalkyl](CH$_2$)p, N[(C$_1$-C$_3$)alkylene-aryl](CH$_2$)p or N[(C$_1$-C$_3$)alkylene-(C$_5$-C$_6$)heteroaryl](CH$_2$)p with NH(CH$_2$)p, N(C$_1$-C$_6$)alkyl-(CH$_2$)p being more preferred. A preferred N(C$_1$-C$_6$)alkyl is N(C$_1$-C$_4$)alkyl, more preferably NCH$_3$ or NCH$_2$CH$_3$ with NCH$_3$ being more preferred. In a preferred embodiment L is O(CH$_2$)p. In another preferred embodiment L is S(CH$_2$)p. In a further embodiment L is NH(CH$_2$)p. Most preferred L is O, S or NH with O being especially preferred.

Preferably p is 0, 1, 2, or 3, more preferred 0 or 1, with 0 being most preferred;

More preferably, m is 2 and s is 2 and L is O, S or NH, preferably O.

In a further embodiment the present invention relates to a compound of formula (I) selected from the group consisting of 6-[4-(1-Amino-propyl)-4-(tetrahydro-pyran-4-yl)-cyclohexyloxy]-7-chloro-2H-isoquinolin-1-one,
6-[4-(1-Amino-ethyl)-4-ethyl-cyclohexyloxy]-7-chloro-2H-isoquinolin-1-one,
6-[4-(1-Amino-propyl)-4-propyl-cyclohexyloxy]-7-chloro-2H-isoquinolin-1-one,
6-[4-(Amino-cyclopropyl-methyl)-4-propyl-cyclohexyloxy]-7-chloro-2H-isoquinolin-1-one,
6-[4-(1-Amino-propyl)-4-isopropyl-cyclohexyloxy]-7-chloro-2H-isoquinolin-1-one,
6-[4-(1-Amino-ethyl)-4-cyclopropylmethyl-cyclohexyloxy]-7-chloro-2H-isoquinolin-1-one,
6-[4-(1-Amino-propyl)-4-cyclopropylmethyl-cyclohexyloxy]-7-chloro-2H-isoquinolin-1-one,
6-[4-(1-Amino-butyl)-4-cyclopropylmethyl-cyclohexyloxy]-7-chloro-2H-isoquinolin-1-one,
6-[4-(Amino-cyclopropyl-methyl)-4-cyclopropylmethyl-cyclohexyloxy]-7-chloro-2H-isoquinolin-1-one, 6-[4-(1-Amino-2-methyl-propyl)-4-cyclopropylmethyl-cyclohexyloxy]-7-chloro-2H-isoquinolin-1-one,
6-[4-(1-Amino-propyl)-4-isopropoxymethyl-cyclohexyloxy]-7-chloro-2H-isoquinolin-1-one,
6-[4-(1-Amino-ethyl)-4-cyclobutyl-cyclohexyloxy]-7-chloro-2H-isoquinolin-1-one,
6-[4-(1-Amino-propyl)-4-cyclobutyl-cyclohexyloxy]-7-chloro-2H-isoquinolin-1-one,
6-[4-(1-Amino-propyl)-4-cyclopentyl-cyclohexyloxy]-7-chloro-2H-isoquinolin-1-one,
6-[4-(Amino-phenyl-methyl)-4-cyclopentyl-cyclohexyloxy]-7-chloro-2H-isoquinolin-1-one,
6-[4-(1-Amino-propyl)-4-methyl-cyclohexyloxy]-7-chloro-2H-isoquinolin-1-one,
6-[4-(1-Amino-propyl)-4-isobutyl-cyclohexyloxy]-7-chloro-2H-isoquinolin-1-one,
6-[4-(1-Amino-propyl)-4-benzyl-cyclohexyloxy]-7-chloro-2H-isoquinolin-1-one
6-[4-(1-Amino-propyl)-4-ethyl-cyclohexyloxy]-7-chloro-2H-isoquinolin-1-one,
6-[4-(1-Amino-butyl)-4-isopropyl-cyclohexyloxy]-7-chloro-2H-isoquinolin-1-one,
6-[4-(1-Amino-butyl)-4-ethyl-cyclohexyloxy]-7-methyl-2H-isoquinolin-1-one,
6-[4-(1-Amino-ethyl)-4-ethyl-cyclohexyloxy]-7-methyl-2H-isoquinolin-1-one,
6-[4-(1-Amino-propyl)-4-butyl-cyclohexyloxy]-7-chloro-2H-isoquinolin-1-one,
6-[4-(1-Amino-propyl)-4-butyl-cyclohexyloxy]-4-benzyl-7-chloro-2H-isoquinolin-1-one,
6-[4-(1-Amino-2,2,2-trifluoro-ethyl)-4-cyclo-propylmethyl-cyclohexyloxy]-7-chloro-2H-isoquinolin-1-one,
6-[4-(1-Amino-2,2,2-trifluoro-ethyl)-4-isopropyl-cyclohexyloxy]-7-chloro-2H-isoquinolin-1-one,
6-[4-(1-Amino-2,2,3,3,3-pentafluoro-propyl)-4-isopropyl-cyclohexyloxy]-7-chloro-2H-isoquinolin-1-one,
6-[4-(Amino-thiazol-2-yl-methyl)-4-isopropyl-cyclohexyloxy]-7-chloro-2H-isoquinolin-1-one, and
6-[4-(Amino-thiazol-5-yl-methyl)-4-isopropyl-cyclohexyloxy]-7-chloro-2H-isoquinolin-1-one,
their stereoisomeric and/or tautomeric forms and/or their pharmaceutically acceptable salts thereof.

In a further embodiment a compound is selected from the group consisting of
cis-6-[4-(1-amino-propyl)-4-(tetrahydropyran-4-yl)-cyclohexyloxy]-7-chloro-2H-isoquinolin-1-one,
cis-6-[4-(1-Amino-propyl)-4-ethyl-cyclohexyloxy]-7-chloro-2H-isoquinolin-1-one,
cis-6-[4-(1-Amino-butyl)-4-isopropyl-cyclohexyloxy]-7-chloro-2H-isoquinolin-1-one,
cis-6-[4-(1-Amino-butyl)-4-ethyl-cyclohexyloxy]-7-methyl-2H-isoquinolin-1-one,
cis-6-[4-(1-Amino-ethyl)-4-ethyl-cyclohexyloxy]-7-methyl-2H-isoquinolin-1-one,
cis-6-[4-(1-Amino-propyl)-4-butyl-cyclohexyloxy]-7-chloro-2H-isoquinolin-1-one, and
cis-6-[4-(1-Amino-propyl)-4-butyl-cyclohexyloxy]-4-benzyl-7-chloro-2H-isoquinolin-1-one,
their stereoisomeric and/or tautomeric forms and/or pharmaceutically acceptable salts thereof.

In a further embodiment a compound is selected from the group consisting of
cis-6-[4-((S)-1-Amino-propyl)-4-methyl-cyclohexyloxy]-7-chloro-2H-isoquinolin-1-one,
cis-6-[4-((R)-1-Amino-propyl)-4-methyl-cyclohexyloxy]-7-chloro-2H-isoquinolin-1-one,
cis-6-[4-((S)-1-Amino-propyl)-4-(tetrahydro-pyran-4-yl)-cyclohexyloxy]-7-chloro-2H-isoquinolin-1-one,
cis-6-[4-((R)-1-Amino-propyl)-4-(tetrahydro-pyran-4-yl)-cyclohexyloxy]-7-chloro-2H-isoquinolin-1-one,
cis-6-[4-((R)-1-Amino-propyl)-4-ethyl-cyclohexyloxy]-7-chloro-2H-isoquinolin-1-one,
cis-6-[4-((S)-1-Amino-propyl)-4-ethyl-cyclohexyloxy]-7-chloro-2H-isoquinolin-1-one,
cis-6-[4-((S)-Amino-cyclopropyl-methyl)-4-cyclopropylmethyl-cyclohexyloxy]-7-chloro-2H-isoquinolin-1-one, and
cis-6-[4-((R)-Amino-cyclopropyl-methyl)-4-cyclopropylmethyl-cyclohexyloxy]-7-chloro-2H-isoquinolin-1-one,
their tautomeric forms and/or pharmaceutically acceptable salts thereof.

In a further embodiment a compound is selected from the group consisting of
cis-6-[4-(1-Amino-ethyl)-4-ethyl-cyclohexyloxy]-7-methyl-2H-isoquinolin-1-one,
cis-6-[4-(1-Amino-propyl)-4-ethyl-cyclohexyloxy]-7-fluoro-2H-isoquinolin-1-one,
cis-6-[4-(1-Amino-propyl)-4-ethyl-cyclohexyloxy]-7-fluoro-5-methyl-2H-isoquinolin-1-one,
cis-6-[4-(1-Amino-propyl)-4-ethyl-cyclohexyloxy]-7-methyl-2H-isoquinolin-1-one,
cis-6-[4-(1-Amino-propyl)-4-ethyl-cyclohexyloxy]-5,7-dimethyl-2H-isoquinolin-1-one,
cis-6-[4-(1-Amino-propyl)-4-methoxy-cyclohexyloxy]-7-chloro-2H-isoquinolin-1-one,
trans-6-[4-(1-Amino-propyl)-4-methoxy-cyclohexyloxy]-7-chloro-2H-isoquinolin-1-one,
6-[4-(1-Amino-propyl)-4-ethoxy-cyclohexyloxy]-7-chloro-2H-isoquinolin-1-one,
cis-6-[4-(Amino-phenyl-methyl)-4-methyl-cyclohexyloxy]-7-chloro-2H-isoquinolin-1-one,
cis-6-[4-(1-Amino-butyl)-4-methyl-cyclohexyloxy]-7-chloro-2H-isoquinolin-1-one,
cis-6-[4-(Amino-phenyl-methyl)-4-cyclopropylmethyl-cyclohexyloxy]-7-chloro-2H-isoquinolin-1-one,
cis-6-[4-(1-Amino-3-methyl-butyl)-4-cyclopropylmethyl-cyclohexyloxy]-7-chloro-2H-isoquinolin-1-one,
cis-6-[4-(1-Amino-2-methyl-propyl)-4-cyclohexyl-cyclohexyloxy]-7-chloro-2H-isoquinolin-1-one,
cis-6-[4-(1-Amino-propyl)-4-(4,4,4-trifluoro-butyl)-cyclohexyloxy]-7-chloro-2H-isoquinolin-1-one,
cis-6-[4-(1-Amino-propyl)-4-(tetrahydro-pyran-4-ylmethyl)-cyclohexyloxy]-7-chloro-2H-isoquinolin-1-one,
cis-6-[4-(Amino-cyclopropyl-methyl)-4-(tetrahydro-pyran-4-ylmethyl)-cyclohexyloxy]-7-chloro-2H-isoquinolin-1-one,
cis-6-[4-(Amino-cyclopropyl-methyl)-4-methyl-cyclohexyloxy]-7-chloro-2H-isoquinolin-1-one,
cis-6-[4-(Amino-cyclopropyl-methyl)-4-ethyl-cyclohexyloxy]-7-chloro-2H-isoquinolin-1-one,
cis-6-[4-(1-Amino-propyl)-4-ethoxymethyl-cyclohexyloxy]-7-chloro-2H-isoquinolin-1-one,
cis-6-[4-(1-Amino-ethyl)-4-cyclopropyl-cyclohexyloxy]-7-chloro-2H-isoquinolin-1-one,
cis-6-[4-(Amino-cyclopropyl-methyl)-4-(4,4,4-trifluoro-butyl)-cyclohexyloxy]-7-chloro-2H-isoquinolin-1-one,
cis-6-[4-(1-Amino-propyl)-4-cyclopropyl-cyclohexyloxy]-7-chloro-2H-isoquinolin-1-one,
cis-6-[4-(Amino-cyclopropyl-methyl)-4-cyclopropyl-cyclohexyloxy]-7-chloro-2H-isoquinolin-1-one
cis-6-[4-(1-Amino-propyl)-4-(tetrahydro-thiopyran-4-yl)-cyclohexyloxy]-7-chloro-2H-isoquinolin-1-one, cis-6-[4-(1-Amino-ethyl)-4-propyl-cyclohexyloxy]-7-chloro-2H-isoquinolin-1-one,
cis-6-[4-(1-Amino-ethyl)-4-ethyl-cyclohexyloxy]-7-fluoro-2H-isoquinolin-1-one,
cis-6-[4-(1-Amino-ethyl)-4-ethyl-cyclohexyloxy]-7-fluoro-5-methyl-2H-isoquinolin-1-one,
cis-6-[4-(1-Amino-ethyl)-4-ethyl-cyclohexyloxy]-4-benzyl-7-chloro-2H-isoquinolin-1-one,
cis-7-Chloro-6-{4-[1-(cyclopropylmethyl-amino)-propyl]-4-ethyl-cyclohexyloxy}-2H-isoquinolin-1-one,
cis-6-[4-(1-Benzylamino-propyl)-4-ethyl-cyclohexyloxy]-7-chloro-2H-isoquinolin-1-one,
cis-7-Chloro-6-[4-ethyl-4-(1-isobutylamino-propyl)-cyclohexyloxy]-2H-isoquinolin-1-one,
cis-6-[4-(1-Butylamino-propyl)-4-ethyl-cyclohexyloxy]-7-chloro-2H-isoquinolin-1-one,
6-[4-(1-Amino-2-methyl-propyl)-4-isopropyl-cyclohexyloxy]-7-chloro-2H-isoquinolin-1-one,
cis-6-[4-(1-Amino-propyl)-4-isopropyl-cyclohexyloxy]-7-chloro-4-fluoro-2H-isoquinolin-1-one (90),
cis-6-[4-(1-Amino-propyl)-4-ethyl-cyclohexyloxy]-7-chloro-4-fluoro-2H-isoquinolin-1-one,
cis-6-[4-(1-Amino-propyl)-4-ethyl-cyclohexyloxy]-4-bromo-7-chloro-2H-isoquinolin-1-one,
cis-6-[4-(1-Amino-propyl)-4-ethyl-cyclohexyloxy]-7-chloro-1-oxo-1,2-dihydro-isoquinoline-4-carbonitrile,
cis-6-[4-(1-Amino-propyl)-4-isopropyl-cyclohexyloxy]-4-bromo-7-chloro-2H-isoquinolin-1-one,
cis-6-[4-(1-amino-2-fluoro-ethyl)-4-ethyl-cyclohexyloxy]-7-chloro-2H-isoquinolin-1-one,
trans-6-[4-(1-amino-2-fluoro-ethyl)-4-ethyl-cyclohexyloxy]-7-chloro-2H-isoquinolin-1-one,
6-[4-(1-amino-3-methoxy-propyl)-4-ethyl-cyclohexyloxy]-7-chloro-2H-isoquinolin-1-one,
cis-6-[4-(1-amino-propyl)-4-(1,1-dioxo-tetrahydrothiopyran-4-yl)-cyclohexyloxy]-7-chloro-2H-isoquinolin-1-one,
6-[34'-Amino-propyl)-3-propyl-cyclopentoxy]-7-chloro-2H-isoquinolin-1-one, and
6-[4-(1-Amino-propyl)-4-trifluoromethyl-cyclohexyloxy]-7-chloro-2H-isoquinolin-1-one,
their stereoisomeric and/or tautomeric forms and/or pharmaceutically acceptable salts thereof.

In a further embodiment a compound is selected from the group consisting of
cis 1-[4-(5,7-Dimethyl-isoquinolin-6-yloxy)-1-ethyl-cyclohexyl]-propylamine,
cis-1-[1-Ethyl-4-(7-fluoro-soquinolin-6-yloxy)-cyclohexyl]-propylamine,
cis-1-[1-Ethyl-4-(7-methyl-isoquinolin-6-yloxy)-cyclohexyl]-propylamine,
cis-1-[1-Ethyl-4-(7-fluoro-5-methyl-isoquinolin-6-yloxy)-cyclohexyl]-propylamine,
cis-1-[1-Ethyl-4-(7-fluoro-5-methyl-isoquinolin-6-yloxy)-cyclohexyl]-ethylamine,
cis-1-[4-(7-Bromo-isoquinolin-6-yloxy)-1-ethyl-cyclohexyl]-ethylamine,
cis-1-[4-(7-Methyl-isoquinolin-6-yloxy)-1-ethyl-cyclohexyl]-ethylamine,
cis-1-[4-(5-Chloro-isoquinolin-6-yloxy)-1-ethyl-cyclohexyl]ethylamine,
cis-6-[4-(1-Amino-ethyl)-4-propyl-cyclohexyloxy]-7-chloro-isoquinolin-1-ylamine, and
[4-(1-Amino-propyl)-4-methyl-cyclohexyl]-isoquinolin-6-yl-amine,
and their stereoisomeric and/or tautomeric forms and/or pharmaceutically acceptable salts thereof.

In any embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

Isoquinoline substitution pattern is numbered according to IUPAC rules:

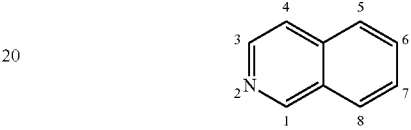

The terms isoquinolone and isoquinolinone are used synonymously. All references to "compound(s) of formula (I)" herein refer to compound(s) of the formula (I), (II) (IIIa), (IIIb) and (IV) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. The hydrochloride salt is a preferred salt.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The present invention also includes physiologically functional derivatives of a compound of formula (I). A physiologically functional derivative as used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention.

These prodrugs may themselves be active or not.

The invention relates to compounds of the formula (I) in the form of their stereoisomeric forms, which include racemates, enantiomerically enriched mixtures, pure enantiomers and diastereomers and mixtures in any ratio thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The present invention also relates to the compounds of the formula (I) and/or their pharmaceutically acceptable salts for use as pharmaceuticals (or medicaments), to the use of the compounds of the formula (I) and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

In a further embodiment the invention also relates to the use of a compound of formula (I) and/or a pharmaceutically acceptable salt thereof for the treatment and/or prevention of hypertension, pulmonary hypertension, fibroid liver, liver failure, nephropathy, renal failure, chronic obstructive pulmonary disease (COPD), cerebral vasospasm, pain, spinal cord injury, erectile dysfunction, blood vessel restenosis, or cancer development and progression.

In a further embodiment the invention relates to the use of a compound of formula (I) and/or a pharmaceutically acceptable salt thereof for curative approaches associated with stem cell or induced pluripotent stem cell treatment, improvement of recognition or for the treatment or prevention of fibroid heart, depression, epilepsy, renal papillary necrosis, tubulointerstitial dysfunction, multiple sclerosis, vessel stenosis for example carotid stenosis or lipid disorders.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

Compounds of formula (I) may be made in the following manner:

Compounds of the general formula (I) can be assembled from a suitably substituted isoquinoline moiety and a suitably substituted cycloalkyl amine moiety. Isoquinolines and isoquinolones like (i) or (ii), bearing a useful residue for coupling in 6-position, can be obtained by a wide variety of methods, for example reviewed in Alvarez et al. Science of Synthesis 2005, 15, 661-838 and 839-906 and references cited therein. Isoquinolines can also be converted to isoquinolones by methods described in the literature e.g. WO 2007/012421 or WO 2007/012422, like conversion of a suitable isoquinoline into the corresponding N-oxide with an oxidating agent like hydrogen peroxide or metachloro perbenzoic acid and subsequent conversion into the corresponding 1-chloro derivative by a chlorinating agent like phosphorous oxy chloride, followed by displacement of the chlorine by an alcohol under basic condition like sodium methoxide in methanol or conversion into the corresponding 2H-isoquinolone by for example treatment with ammonium acetate in acetic acid at elevated temperature. Also the N-oxide can be directly converted into the corresponding 1-alkoxy derivative by reacting it with a suitable chloroformiate in an alcoholic solvent like methanol in presence of a base like triethylamine. It is understood, that the hydroxyl-group in 6-position of (ii) can be liberated at a suitable stage of the synthesis e.g. from treatment of a corresponding 6-methoxy derivative with lewis acids like aluminium chloride or boron tribromide. It is furthermore understood, that 2H-isoquinolones can be converted into suitably protected 1-alkoxy isoquinolones by a variety of methods e.g. treatment of the corresponding 2H-isoquinolones with alkylating agents like benzyl bromide or methyl iodide in the presence of a suitable base like silver carbonate or triethyl amine in a suitable solvent like toluene or THF, or conversion of the said 2H-isoquinolones into their 1-chloro derivatives by treatment with a chlorinating agent like phosphorous oxychloride, followed by displacement of the chlorine by an alcohol e.g. under basic conditions like sodium methoxide in methanol. It is understood, that residues $R_3$, $R_4$, $R_5$, $R_7$, and/or $R_8$ can either be incorporated in the starting materials for the synthesis of the respective isoquinoline or isoquinolone or can be introduced at a suitable later stage e.g. by halogenation like bromination or chlorination and subsequent replacement of said halogen by methods well precedented in the literature like for example Suzuki or Hartwig Buchwald couplings using appropriate catalysts and coupling partners like boronic acids, amines or anilines.

One possible synthesis for a cycloalkyl amine substituted isoquinolinone with L=O (v) is described below in an exemplary fashion, but does not limit the present invention. The cycloalkyl amine substituted isoquinolinones (for example compound v) can be synthesized via a variety of methods. The following general scheme 1 illustrates some of the possible ways to access the isoquinolinones, but does not limit the present invention.

Scheme 1

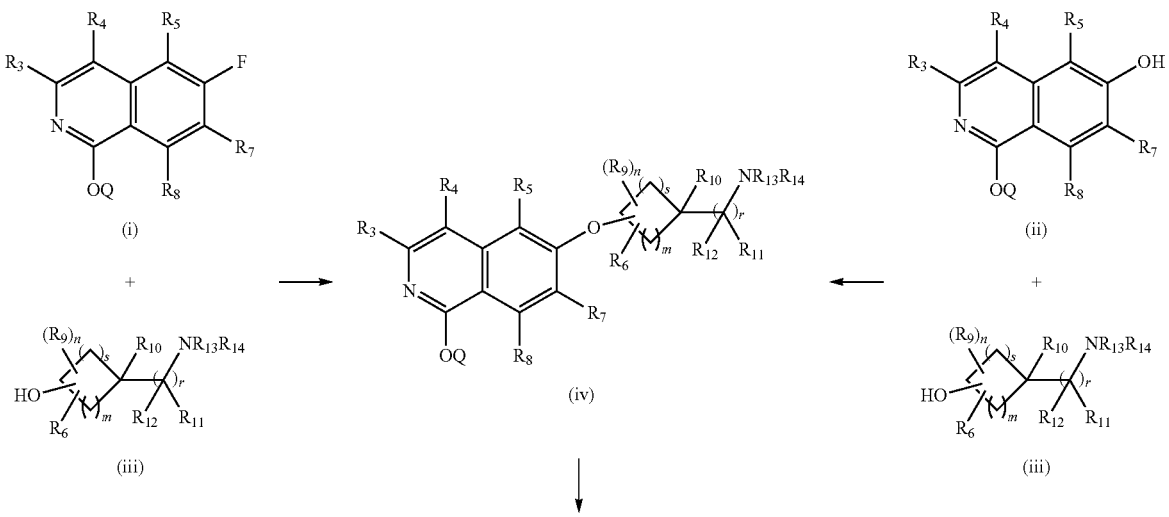

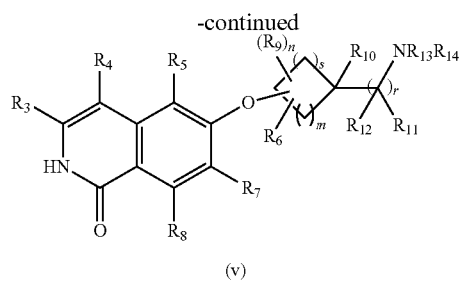

(v)

6-Fluoro-isoquinolones (i), for example substituted by $R_3$, $R_4$, $R_5$, $R_7$, and/or $R_8$ being for instance independently from each other substituents like hydrogen, alkyl, alkoxy or halide, can be reacted with suitable $R_{13}/R_{14}$ substituted amino alcohols wherein $R_{13}/R_{14}$ are independently from each other for example hydrogen, alkyl or a protecting group like for example Bac or Cbz in the presence of base such as DBU, cesium carbonate, or sodium hydride at temperatures ranging from ambient to 100° C. to give the corresponding derivatives (iv). Optionally, this conversion can already be performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base.

Alternatively, the amino alcohols can be coupled to 6-hydroxy-isoquinolones, such as (ii), under inversion of the hydroxyl bearing carbon center of compounds like (iii), either protected with a suitable protecting group Q or unprotected, via a Mitsunobu reaction using triphenylphosphine and dialkylazodicarboxylates such as diethylazodicarboxylate or diisopropylazodicarboxylate in a suitable solvent like tetrahydrofuran, or toluene.

The products like (iv) obtained via these methods can then either be liberated to give compounds of type (v) or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step, like for example acidic removal of Boc-groups. Furthermore an amino group can be acylated by reacting it with a suitable acid chloride in the presence of a base like triethyl amine or Hünig's base or by reacting it with a suitable carboxylic acid in the presence of a base like triethylamine or Hünig's base and a coupling reagent like EDC, PyBOP or TOTU.

In case of use of protected isoquinolones, cleavage of the used protection groups is required to liberate the desired isoquinolone (v). This liberation, however, can be performed before or after the reductive amination step, depending on the nature of the used aldehyde/ketone and the protection group used.

Isoquinolone derivatives like (v) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The cycloalkyl amine moieties like for example (iii) can by synthesized via a variety of methods. The following general schemes illustrate some of the possible ways to access the amines, but do not limit the present invention. It is within the abilities of a person skilled in the art to replace the exemplary compounds shown in the schemes and exemplary reagent given in the text by appropriate alternative compounds or reagents or to omit or add synthetic steps when appropriate.

The synthesis of an cycloalkyl aminoalcohol (iii) is described exemplary in schemes 2 and 3 but does not limit the scope of substituents in the present invention. A cycloalkyl amine moiety (iii) with a secondary or tertiary amine subunit can for example be accessed starting from a suitably substituted cycloalkylnitrile (vi), which can be substituted with functionalities as alkyl, alkoxy, or acetals. The nitrile can get functionalized in alpha-position by reaction with suitable electrophiles (for example alkyl halides, cycloalkyl p-toluenesulfonates, alkoxy halides or aldehydes) using an appropriate base like lithium hexamethyldisilazide, lithium diisopropylamide or metal hydrides in inert solvents like tetrahydrofuran, toluene or heptane.

Scheme 2

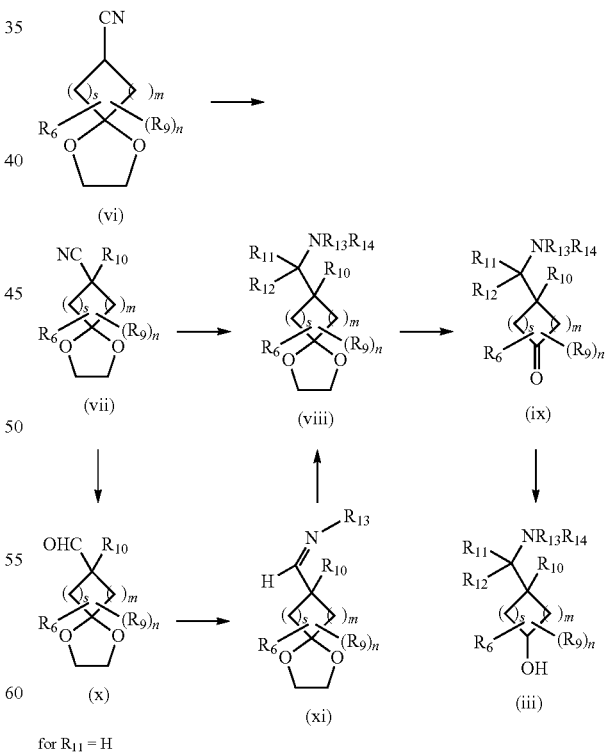

for $R_{11}$ = H

The functionalized nitrile (vii) can then be directly reacted with suitable nucleophiles for the introduction of functional groups $R_{11}$ and $R_{12}$, for example lithium organyls or Grignard reagents to give compounds like (viii). A suitable protecting group like t-butyloxycarbonyl or benzyloxycarbonyl may or may not be attached after this step depending on the nature of the starting nitrite and the complexity of the reactions to follow. For $R_{11}=R_{12}$, lithium organyls can be used as nucleophiles activated by addition of lewis acids like titanium isopropoxylate and cerium chloride.

For $R_{11}$ is H, the intermediate imine formed on addition of the nucleophiles can be isolated and reduced by suitable reductive agents like cyanoborohydrides or borohydrides in solvents such as tetrahydrofuran or alcohols. Alternatively, the nitrile (vii) can be reduced to the aldehyde (x) by suitable hydride donor reagents like diisobutylaluminiumhydride in cold organic solvents such as diethylether or toluene and converted to appropriate imines (xi) like benzylimines or N-tert-butanesulfinyl imines via a lewis acid catalysed reaction with suitably functionalized amines. These imines (xi) can then be reacted with suitable nucleophilic reagents like lithium organyls, Grignard reagents or trimethylsilanes in combination with tetraalkyl fluorides to introduce a variety of substituents like alkyl, cycloalkyl or heterocyclyl groups. The keto functionality can then be liberated by methods known to the person skilled in art, for example by treatment with aqueous acids like acetic acid or hydrochloric acid in acetone mixtures, and subsequently reduced to the corresponding alcohols (iii), generally as cis/trans mixtures, by suitable reducing agents like borohydrides in alcohols, tetrahydrofuran or toluene at deep temperatures.

This liberation, however, can also be performed after the nitrile functionalization step (Scheme 3), depending on the nature of the used nitrile and the substitution pattern. If the ketone is reduced before the nitrile gets functionalized, generally only one isomer (cis or trans) is obtained in high selectivity. For the conversion of nitriles from type (xiii) to the amines (iii) the use of a suitable protecting group on the alcohol functionality may prove beneficial. Suitable protecting groups are known to the person skilled in art and may be ethers, like tetrahydropyrane, methoxymethyl or silyl ethers.

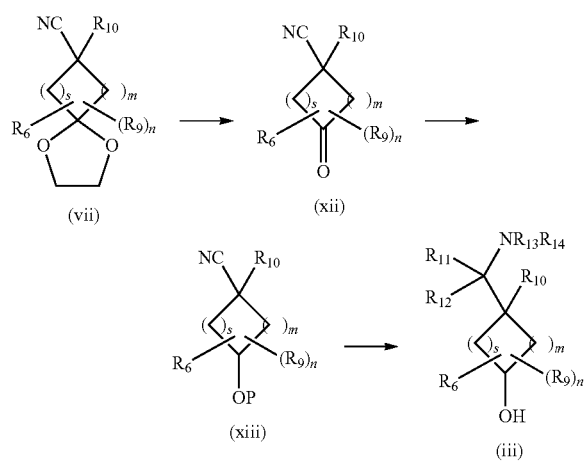

To obtain cycloalkyl amino moieties other than cycloalkyl aminoalcohols, various methods can be applied. The following general scheme (scheme 4) illustrates some of the possible ways to access these amines, but do not limit the present invention.

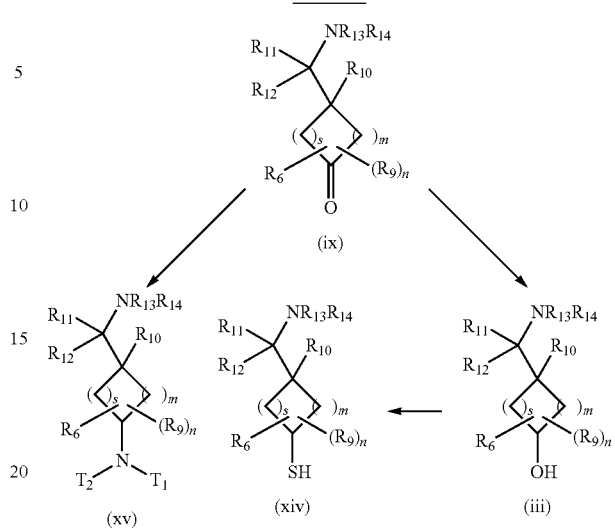

For instance, the hydroxy functionality of a compound (iii) can be converted to a thiol via a Mitsunobu reaction using thioacetate and subsequent basic cleavage with a suitable base, leading to amino moieties of type (xiv). These thiols can—after coupling to suitable isoquinolinones under useful reaction conditions like for example in a similar fashion as described above in scheme 1 for the coupling of (iii)—then be used to obtain compounds of formula (I) with the linker unit L=S—or optionally be oxidized via methods known to the person skilled in the art to the corresponding sulfoxides and sulfones (for obtaining compounds of formula (I) with the linker unit L=SO and $SO_2$). The corresponding amines can be accessed via a reductive amination step starting from ketones such as compound (ix or xii) using suitable amines in the presence of a reducing agent like sodium triacetoxy borohydride, sodium borohydride or sodium cyanoborohydride in the presence of a water withdrawing agent like molecular sieves or a suitable ortho ester.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formula (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as NMR, IR and mass spectrometry (MS) can be used for characterizing a compound of the invention.

EXAMPLES

The following examples illustrate the various embodiments of the present invention and are part of the present invention. Cis and trans nomenclature in the title of the respective compounds refer to the relative configuration of the —[CR$_{11}$R$_{12}$]$_r$NR$_{13}$R$_{14}$ residue and the L-residue at the cycloalkyl ring. This convention is maintained for the respective precursors.

6,7-difluoro-5-methyl-isoquinoline (25)

a) [1-(3,4-Difluoro-2-methylphenyl)-methylidene]-2,2-dimethoxyamine (22)

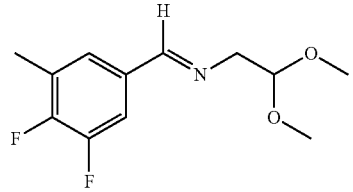

3,4-difluoro-2-methylbenzaldehyde (26.0 g, 166 mmol) was dissolved in toluene (182 mL) and reacted with 2-aminoacetaldehyde dimethylacetal (19.3 g, 183.2 mmol) and toluene sulphonic acid (3.2 g) for 2 hours in a Dean-Stark apparatus. The solution was allowed to cool down, extracted with saturated sodium bicarbonate solution, water and brine, dried over sodium sulphate and evaporated to dryness to give 40.4 g of a dark yellow oil which was used without further purification.

b) 3,4-Difluoro-2-methylbenzyl-2,2-dimethoxyethylamine (23)

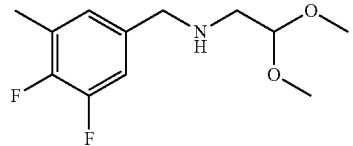

[1-(3,4-Difluoro-2-methylphenyl)-methylidene]-2,2-dimethoxyamine (22, 40.4 g) was dissolved in ethanol (225 mL). Sodium borohydride (4.8 g, 124 mmol) was added portionwise. Stirring was continued overnight. For workup, acetic acid was added until no gas evolution could be observed. Then the solution was evaporated to dryness, taken up in dichloromethane and washed with saturated sodium bicarbonate solution and twice with water. The organic layer was washed with brine, dried over magnesium sulphate and evaporated to dryness. The crude product obtained (37.8 g) was used without purification.

c) N-(3,4-Difluoro-2-methylbenzyl)-N-(2,2-dimethoxyethyl)-4-methylphenyl-sulphonylamine (24)

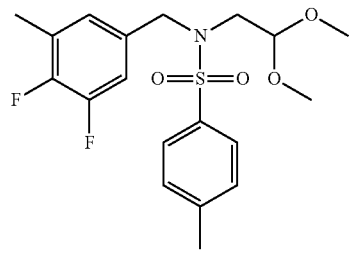

3,4-Difluoro-2-methylbenzyl-2,2-dimethoxyethylamine (23, 37.8 g) was dissolved in dichloromethane (100 mL). Pyridine (42 mL) was added. At 0° C. a solution of p-toluenesulphonyl chloride (36.8 g, 193 mmol) in dichloromethane was added dropwise. The reaction was allowed to warm to room temperature and stirring continued until the conversion was complete. For workup, the reaction mixture was diluted with dichloromethane (100 mL) and extracted twice with 1.5M hydrochloric acid, twice with sodium bicarbonate solution and once with brine. The organic layer was dried over magnesium sulphate, evaporated to dryness to give crude product as an orange oil (68.3 g). This was used without further purification.

d) 6,7-difluoro-5-methyl-isoquinoline (25)

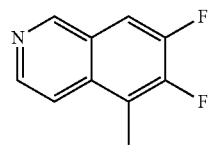

Aluminium trichloride (111.7 g, 838 mmol) was suspended in dichloromethane (250 mL) at 0° C. A solution of N-(3,4-difluoro-2-methylbenzyl)-N-(2,2-dimethoxyethyl)-4-methylphenyl-sulphonylamine (24, 68.3 g) in dichloromethane (250 mL) was added. The reaction mixture was heated at 50° C. for 2 hours, before being cooled to 0° C. and poured on ice. The organic layer was separated, and the aqueous layer extracted twice more with dichloromethane/isopropanol (3:1). The combined organic phase was extracted twice with saturated sodium bicarbonate solution and dried over magnesium sulphate, before filtration and evaporation gave 63.5 g of crude dark brown semi-solid product. This was purified by chromatography on silica gel. Elution with ethyl acetate/heptane (5%:95% to 35%:65%) gave 11.3 g of the title compound 25 as a tan-coloured solid. R$_f$=0.86 min (Method G). Detected mass: 180.1 (M+H$^+$).

The following isoquinolines were synthesized from the respective benzaldehydes in a similar fashion as described for 25.

| Compound | Starting compound | Product | Chemical Name | [M + H$^+$] | R$_f$/ [min] | Method |
|---|---|---|---|---|---|---|
| 26 | 3,5-dimethyl-4-fluoro-benzaldehyde | | 5,7-dimethyl-6-fluoro-isoquinoline | 176.1 | 1.06 | G |

| Com- pound | Starting compound | Product | Chemical Name | [M + H⁺] | $R_t$/ [min] | Method |
|---|---|---|---|---|---|---|
| 27 | 3,4-difluoro-benzaldehyde | | 6,7-difluoro-isoquinoline | 166.1 | 1.07 | C |
| 28 | 3-bromo-4-fluoro-benzaldehyde | | 7-bromo-6-fluoro-isoquinoline | 226.0 228.3 | 0.91 | J |
| 29 | 4-fluoro-3-methoxy-benzaldehyde | | 6-fluoro-7-methoxy-isoquinoline | 178.1 | 0.90 | G |
| 30 | 4-fluoro-3-methyl-benzaldehyde | | 6-fluoro-7-methyl isoquinoline | 161.9 | 0.90 | G |

1-Benzyloxy-7-chloro-6-fluoro-isoquinoline (1)

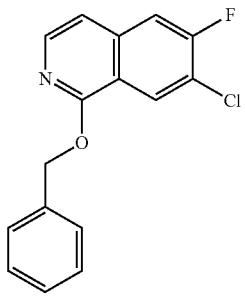 [SMILES: Fc1cc2ccnc(OCc3ccccc3)c2cc1Cl]

7-Chloro-6-fluoro-2H-isoquinolin-1-one (prepared according to WO 2007/012422; 52.2 g) was dissolved in THF (1 L). After addition of silver carbonate (145.5 g) and benzyl bromide (40.6 mL), the mixture was stirred at room temperature overnight. Another 6.2 mL of benzyl bromide were added and the mixture was stirred at 70° C. for 2 h. After cooling down to room temperature, the reaction mixture was diluted by addition of 1 L of ethyl acetate and filtered over celite. The filter cake was washed thoroughly, the organic layer was evaporated and subjected to silica gel chromatography (n-heptanes: methyl tert. butyl ether) to give 27.8 g of the title compound 1. $R_t$=3.73 min (Method A). Detected mass: 288.1 (M+H⁺).

1-Benzyloxy-4-benzyl-7-chloro-6-fluoro-isoquinoline (2)

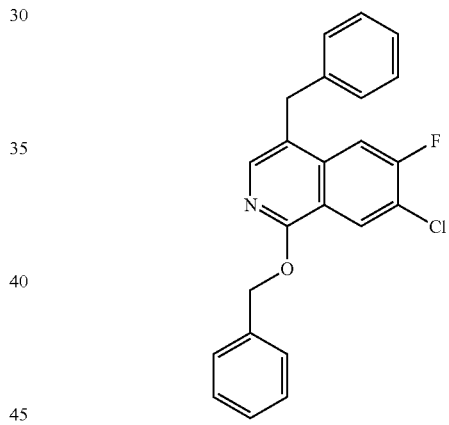

As a side product of the preparation of 1-benzyloxy-7-chloro-6-fluoro-isoquinoline (1), 8.45 g of 1-benzyloxy-4-benzyl-7-chloro-6-fluoro-isoquinoline could be isolated by silica gel chromatography. $R_t$=4.04 min (Method A). Detected mass: 378.1 (M+H⁺).

1-Benzyloxy-7-methyl-6-fluoro-isoquinoline (3)

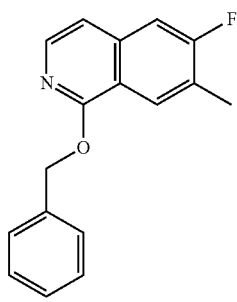 [SMILES: Cc1cc2c(OCc3ccccc3)nccc2cc1F]

1-Benzyloxy-7-methyl-6-fluoro-isoquinoline (3) has been prepared according to the procedure described for the synthesis of 1 starting from 7-methyl-6-fluoro-2H-isoquinolin-1-one (prepared according to the protocol described in WO 2007/012421 or WO 2007/012422). $R_t$=4.00 min (Method A). Detected mass: 268.1 (M+H$^+$).

7-Chloro-6-fluoro-isoquinoline 2-oxide (31)

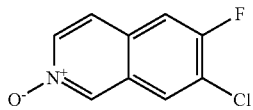 [SMILES: [O-][n+]1ccc2cc(F)c(Cl)cc2c1]

50 g of 7-chloro-6-fluoro-isoquinoline (prepared according to WO 2007/012422) were dissolved in dichloromethane and cooled to 5° C. 69.6 g of m-chloro-perbenzoic acid (70%) were added portionwise. The mixture was stirred at room temperature. When conversion was complete, the mixture was diluted with 1.5 L of dichloromethane and extracted three times with saturated sodium bicarbonate solution. The organic layer was dried over sodium sulphate and evaporated to dryness to give 47.6 g of the desired product 31. $R_t$=0.98 min (Method D). Detected mass: 198.1 (M+H$^+$).

7-Chloro-6-fluoro-1-methoxy-isoquinoline (4)

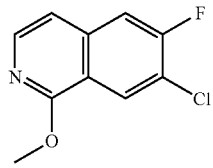

10 g of 7-Chloro-6-fluoro-isoquinoline-2-oxide (31) were dissolved in 100 mL of dry methanol. 12 mL of ethyl chloroformate were added dropwise at −10° C. The mixture was allowed to stir for 15 minutes and then 28 mL of triethylamine, dissolved in 55 mL of methanol, were added dropwise at −20° C. over 1 h.

100 mL of 2N sodium hydroxide solution were added and the formed precipitate was isolated by filtration. Additional product was precipitated by addition of 2N sodium hydroxide solution and water to the mother liquor. The combined solids were dried to give 7.8 g of the desired product. $R_t$=3.75 min (Method A). Detected mass: 212.0 (M+H$^+$).

The following compounds were obtained in a similar fashion as described for the synthesis of 4, starting from the respective isoquinolines.

| Comp. No. | Starting compound | Product | Chemical Name | [M + H$^+$] | $R_t$/ [min] | Method |
|---|---|---|---|---|---|---|
| 32 | 5-Chloro-6-fluoro-isoquinoline | | 5-Chloro-6-fluoro-1-methoxy-isoquinoline | 212.0 | 1.78 | G |
| 33 | 27 | | 6,7-difluoro-1-methoxy-isoquinoline | 196.1 | 3.53 | A |
| 34 | 25 | | 6,7-Difluoro-1-methoxy-5-methyl-isoquinoline | 210.1 | 3.85 | C |
| 35 | 30 | | 6-fluoro-1-methoxy-7-methyl-isoquinoline | 192.1 | 3.44 | C |

| Comp. No. | Starting compound | Product | Chemical Name | [M + H⁺] | $R_t$ [min] | Method |
|---|---|---|---|---|---|---|
| 36 | 26 | | 6-Fluoro-1-methoxy-5,7-dimethyl-isoquinoline | 206.1 | 3.74 | C |
| 37 | 29 | | 6-Fluoro-1,7-dimethoxy-isoquinoline | 208.1 | 3.1 | C |

Example 1 and 2

6-[4-(1-Amino-propyl)-4-(tetrahydropyran-4-yl)-cyclohexyloxy]-7-chloro-2H-isoquinolin-1-one a) 8-(Tetrahydropyran-4-yl)-1,4-dioxa-spiro[4.5]decane-8-carbonitrile (5)

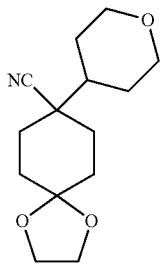

To a 2M solution of lithium diisopropylamide in heptane/tetrahydrofuran/ethylbenzene (18 mL, 35.9 mmol, 1.5 eq.) at −78° C. was added dropwise a solution of 1,4-dioxa-spiro[4.5]decane-8-carbonitrile (commercially available or via literature procedure described for example in Becker et al. Synthesis 1992, 11, 1080-1082; 4.0 g, 23.9 mmol) in tetrahydrofuran (40 mL). After stirring for 30 min at −78° C., 4-iodotetrahydro-2H-pyran (5.1 g, 23.9 mmol, 1 eq.) was added carefully. The reaction mixture was allowed to warm to room temperature over night before being quenched by slow addition of ethanol (10 mL) and water (20 mL) subsequently. The resulting suspension was filtered through celite and extracted three times with dichloromethane. The combined organic phases were concentrated in vacuo and purified by flash chromatography (SiO₂, 0%→30% methanol in dichloromethane) to give 2.80 g of 8-(tetrahydropyran-4-yl)-1,4-dioxa-spiro[4.5]decane-8-carbonitrile (5). $R_t$=1.03 min (Method B). Detected mass: 252.3 (M+H⁺).

b) {1-[8-(Tetrahydropyran-4-yl)-1,4-dioxa-spiro[4.5]dec-8-yl]propyl}-carbamic acid benzyl ester (6)

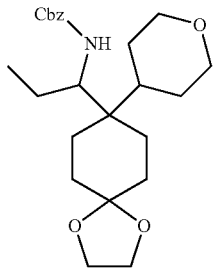 [SMILES: CCC(NC(=O)OCc1ccccc1)C1(C2CCOCC2)CCC2(CC1)OCCO2]

To 8-(tetrahydropyran-4-yl)-1,4-dioxa-spiro[4.5]decane-8-carbonitrile (5, 1.4 g, 5.57 mmol) was added a 2M solution of ethylmagnesium chloride in THF (5.6 mL, 11.1 mmol, 2.0 eq.) and the reaction mixture was refluxed for 72 h. The resulting suspension was cooled to −20° C. and treated with methanol (8 mL). After stirring for 10 min at 0° C., sodium borohydride (376 mg, 9.95 mmol, 2 eq.) was added portionwise and the reaction mixture was stirred at room temperature for 1 h. The solution was diluted with 1N aqueous sodium hydroxide solution (20 mL) and extracted twice with diethylether. The combined organic phases were washed with brine, dried over magnesium sulphate and concentrated in vacuo to give 1.46 g of the crude amine.

The crude product was dissolved in dichloromethane (15 mL), cooled to −78° C. and treated subsequently with triethylamine (0.79 mL, 5.67 mmol, 1.1 eq.) and benzyl chloroformate (0.87 mL, 5.15 mmol, 1 eq.). After stirring for 1 h at room temperature the reaction was quenched by addition of water (20 mL) and extracted three times with dichloromethane. The organic phases were dried over magnesium sulphate, concentrated in vacuo and purified by flash chromatography (SiO₂, 0%→100% ethylacetate in heptane) to give 717 mg of the title compound. $R_t$=1.48 min (Method B). Detected mass: 418.4 (M+H⁺).

c) 4-(1-Aminopropyl)-4-(tetrahydropyran-4-yl)-cyclohexanol (7)

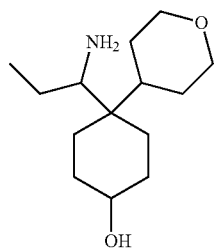 [SMILES: CCC(N)C1(C2CCOCC2)CCC(O)CC1]

The {1-[8-(tetrahydropyran-4-yl)-1,4-dioxa-spiro[4.5]dec-8-yl]propyl}-carbamic acid benzyl ester (6, 717 mg, 1.72 mmol) was dissolved in acetone (5 mL) and 6N aqueous hydrochloric acid (2.5 mL) was added. The solution was stirred for 16 h at room temperature, then dropped carefully into a saturated aqueous sodium bicarbonate solution (100 mL). The mixture was extracted three times with dichloromethane, the organic phases were dried over magnesium sulphate and concentrated in vacuo to give 577 mg of the crude ketone.

The crude product was dissolved in tetrahydrofuran (10 mL), cooled to −30° C. and sodium borohydride (64.3 mg, 1.7 mmol, 1.1 eq.) was added. The reaction mixture was slowly warmed to room temperature and stirred for 2 h before being quenched with water (15 mL). The solution was acidified to pH 2 by addition of 2N aqueous hydrochloric acid and extracted three times with ethylacetate. The combined organic phases were dried over magnesium sulphate and concentrated in vacuo to give 517 mg of the desired alcohol.

The N-protected alcohol was dissolved in methanol (2 mL) and 14.6 mg of palladium on charcoal (10%) were added. The mixture was stirred under a hydrogen atmosphere until conversion was complete. The catalyst was filtered off and the reaction mixture was evaporated to dryness to give 370 mg of the title compound as mixture of diastereomers. $R_t$=0.36 min, 0.60 min (Method B). Detected mass: 242.3 (M+H$^+$).

d) 1-[4-(1-Benzyloxy-7-chloro-isoquinolin-6-yloxy)-1-(tetrahydro-pyran-4-yl)-cyclohexyl]propylamine (8 and 9)

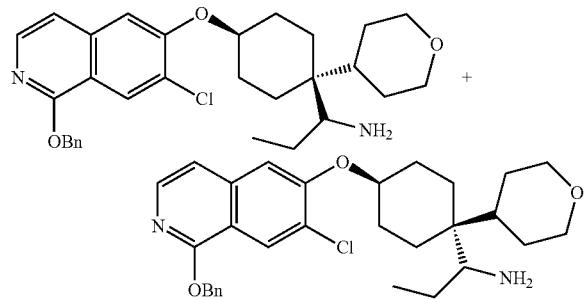

To a suspension of sodium hydride (60%, 167 mg, 4.17 mmol, 3 eq.) in dimethyl acetamide (8 mL) was added a solution of 4-(1-aminopropyl)-4-(tetrahydropyran-4-yl)-cyclohexanol (7,369 mg, 1.53 mmol, 1.1 eq.) in dimethyl acetamide (8 mL). After stirring for 60 min at room temperature a solution of 1-benzyloxy-7-chloro-6-fluoro-isoquinoline (1,400 mg, 1.39 mmol) in dimethyl acetamide (8 mL) was added and stirring was continued first at room temperature, then at 50° C. until the reaction went to completion. The reaction was quenched by addition of water (30 mL) and the reaction mixture was extracted three times with a mixture of dichloromethane and 2-propanol (3:1). The combined organic layers were evaporated, and the obtained crude product was purified by flash chromatography (SiO$_2$, 0%→30% methanol in dichloromethane) to yield 83 mg (earlier eluting isomer 1, 8) and 48 mg (later eluting isomer 2, 9) of the pure diastereoisomers as racemates respectively. The relative stereochemistry was not assigned. Additionally, 166 mg of the product as a diastereomeric mixture could be isolated. $R_t$=0.92 min (8), 0.93 min (9) (Method B). Detected mass: 419.4 (M+H$^+$).

e) 6-[4-(1-Aminopropyl)-4-(tetrahydropyran-4-yl)-cyclohexyloxy]-7-chloro-2H-isoquinolin-1-one (Example 1 and 2)

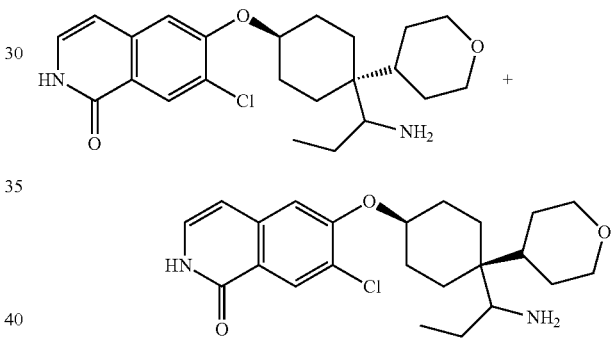

A solution of 1-[4-(1-benzyloxy-7-chloro-isoquinolin-6-yloxy)-1-(tetrahydropyran-4-yl)-cyclohexyl]propylamine (8, 83 mg, 0.16 mmol) in 2-propanol (1 mL) was treated with 2N aqueous hydrochloric acid (0.5 mL) and stirred at room temperature until complete conversion was observed. The reaction mixture was evaporated and lyophilized from water twice to give 68 mg of the title compound (Example 1) as its hydrochloride. $R_t$ 2.40 min (Method A). Detected mass: 419.4 (M+H$^+$).

45 mg of the second diastereomer (Example 2) could be synthesized from 48 mg of 9 following the same procedure. $R_t$=2.40 min (Method A). Detected mass: 419.4 (M+H$^+$). The relative stereochemistry was not assigned.

The following products were synthesized as racemic hydrochlorides in a similar fashion as described for the synthesis of Example 1 starting from the respective aminoalcohols (prepared following the procedure described for the synthesis of 7) and 1-benzyloxy-7-chloro-6-fluoro-isoquinoline (1). If the diastereoisomers could not be separated on an earlier stage of the synthesis, the deprotected products were purified by preparative HPLC and lyophilized from 1N HCl and water, subsequently.

| Ex. No. | Product | Isomer | Chemical Name | [M + H⁺] | $R_t$ [min] | Method |
|---|---|---|---|---|---|---|
| 3 | | 1 | 6-[4-(1-Amino-ethyl)-4-ethyl-cyclohexyloxy]-7-chloro-2H-isoquinolin-1-one | 349.2 | 2.39 | C |
| 4 | | 2 | 6-[4-(1-Amino-ethyl)-4-ethyl-cyclohexyloxy]-7-chloro-2H-isoquinolin-1-one | 349.2 | 2.47 | C |
| 5 | | 1 | 6-[4-(1-Amino-propyl)-4-propyl-cyclohexyloxy]-7-chloro-2H-isoquinolin-1-one | 377.1 | 2.58 | A |
| 6 | | 1 | 6-[4-(Amino-cyclopropyl-methyl)-4-propyl-cyclohexyloxy]-7-chloro-2H-isoquinolin-1-one | 389.2 | 2.60 | A |
| 7 | | 2 | 6-[4-(Amino-cyclopropyl-methyl)-4-propyl-cyclohexyloxy]-7-chloro-2H-isoquinolin-1-one | 389.3, 372.3 [M − NH₃ + H⁺] | 3.04 | D |
| 8 | | 1 | 6-[4-(1-Amino-propyl)-4-isopropyl-cyclohexyloxy]-7-chloro-2H-isoquinolin-1-one | 377.2 | 2.50 | A |
| 9 | | 2 | 6-[4-(1-Amino-propyl)-4-isopropyl-cyclohexyloxy]-7-chloro-2H-isoquinolin-1-one | 377.2 | 2.64 | A |
| 10 | | 1 | 6-[4-(1-Amino-ethyl)-4-cyclopropylmethyl-cyclohexyloxy]-7-chloro-2H-isoquinolin-1-one | 375.2 | 2.55 | C |

| Ex. No. | Product | Isomer | Chemical Name | [M + H⁺] | R_f/[min] | Method |
|---|---|---|---|---|---|---|
| 11 | | 2 | 6-[4-(1-Amino-ethyl)-4-cyclopropylmethyl-cyclohexyloxy]-7-chloro-2H-isoquinolin-1-one | 375.2 | 2.64 | C |
| 12 | | 1 | 6-[4-(1-Amino-propyl)-4-cyclopropyl-methyl-cyclohexyl-oxy]-7-chloro-2H-isoquinolin-1-one | 389.2 | 2.58 | A |
| 13 | | 2 | 6-[4-(1-Amino-propyl)-4-cyclopropyl-methyl-cyclohexyl-oxy]-7-chloro-2H-isoquinolin-1-one | 389.2 | 2.61 | A |
| 14 | | 1 | 6-[4-(1-Amino-butyl)-4-cyclopropylmethyl-cyclohexyloxy]-7-chloro-2H-isoquinolin-1-one | 403.3 | 2.68 | A |
| 15 | | 2 | 6-[4-(1-Amino-butyl)-4-cyclopropylmethyl-cyclohexyloxy]-7-chloro-2H-isoquinolin-1-one | 403.3 | 2.64 | A |
| 16 | | 1 | 6-[4-(Amino-cyclopropyl-methyl)-4-cyclopropylmethyl-cyclohexyloxy]-7-chloro-2H-isoquinolin-1-one | 401.2 | 2.62 | A |
| 17 | | 2 | 6-[4-(Amino-cyclopropyl-methyl)-4-cyclopropylmethyl-cyclohexyloxy]-7-chloro-2H-isoquinolin-1-one | 401.2 | 2.66 | C |

-continued

| Ex. No. | Product | Isomer | Chemical Name | [M + H⁺] | R$_t$/ [min] | Method |
|---|---|---|---|---|---|---|
| 18 | | 1 + 2 | 6-[4-(1-Amino-2-methyl-propyl)-4-cyclopropylmethyl-cyclohexyloxy]-7-chloro-2H-isoquinolin-1-one | 403.2 | 2.50, 2.55 | A |
| 19 | | 1 | 6-[4-(1-Amino-propyl)-4-isopropoxymethyl-cyclohexyloxy]-7-chloro-2H-isoquinolin-1-one | 407.2 | 2.56 | A |
| 20 | | 2 | 6-[4-(1-Amino-propyl)-4-isopropoxymethyl-cyclohexyloxy]-7-chloro-2H-isoquinolin-1-one | 407.2 | 2.70 | A |
| 21 | | 1 | 6-[4-(1-Amino-ethyl)-4-cyclobutyl-cyclohexyloxy]-7-chloro-2H-isoquinolin-1-one | 375.2 | 2.46 | A |
| 22 | | 1 | 6-[4-(1-Amino-propyl)-4-cyclobutyl-cyclohexyloxy]-7-chloro-2H-isoquinolin-1-one | 389.2 | 2.57 | A |
| 23 | | 2 | 6-[4-(1-Amino-propyl)-4-cyclobutyl-cyclohexyloxy]-7-chloro-2H-isoquinolin-1-one | 389.2 | 2.88 | A |
| 24 | | 1 | 6-[4-(1-Amino-propyl)-4-cyclopentyl-cyclohexyloxy]-7-chloro-2H-isoquinolin-1-one | 403.2 | 2.88 | A |
| 25 | | 1 | 6-[4-(Amino-phenyl-methyl)-4-cyclopentyl-cyclohexyloxy]-7-chloro-2H-isoquinolin-1-one | 451.2, 434.2 [M − NH$_3$ + H⁺] | 2.87 | A |

Preparation of 4-(1-Amino-propyl)-4-benzyl-cyclohexanol (13 and 14)

a) [1-(1-Benzyl-4-oxo-cyclohexyl)-propyl]-carbamic acid tert-butyl ester (10)

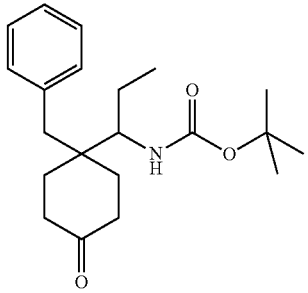 [SMILES: CCC(NC(=O)OC(C)(C)C)C1(Cc2ccccc2)CCC(=O)CC1]

1 g of 8-Benzyl-1,4-dioxa-spiro[4.5]decane-8-carbonitrile, prepared from 1,4-dioxa-spiro[4.5]decane-8-carbonitrile and benzyl bromide in a similar fashion as described for 5, was dissolved in 6 mL of a 1M solution of ethyl magnesium chloride in diethylether. The mixture was heated to reflux for two days. The mixture was cooled to room temperature, diluted by addition of 100 mL of methyl tert. butyl ether and 2 mL of saturated sodium sulphate solution was added. The mixture was filtered over celite and the precipitate was washed with methyl tert. butyl ether. The mixture was evaporated and the residue taken up in 30 mL of ethanol.

189 mg of sodium borohydride was added and the mixture was allowed to stir until conversion was complete. The mixture was evaporated and taken up in 100 mL of ethyl acetate. The organic layer was extracted with dilute hydrochloric acid. When deketalization was complete, the aqueous layer was adjusted to alkaline pH by addition of 2M sodium hydroxide solution and extracted twice with dichloromethane. The combined dichloromethane layer was washed with brine and dried over sodium sulphate.

2.05 g of di tert. butyl dicarbonate and 1.2 g of triethylamine were added and the mixture was allowed to stir for two days. The mixture was washed with 1N sodium hydroxide, 1N hydrochloric acid, water and brine, dried over sodium sulphate and evaporated to dryness. The remaining oil was chromatographed to give 286 mg of the desired product. $R_t$=3.57 min (Method A). Detected mass: 290.2 (M-tert.butyl+H$^+$).

b) [1-(1-Benzyl-4-hydroxy-cyclohexyl)-propyl]-carbamic acid tert-butyl ester (11 and 12)

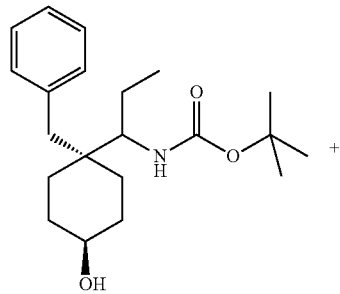
+
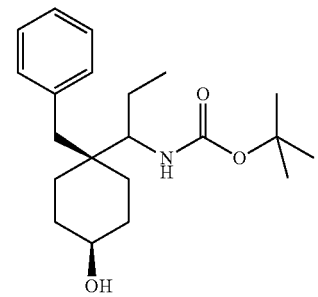

280 mg of 10 were dissolved in 10 mL of ethanol and 34 mg of sodium borohydride were added at −20° C. The mixture was allowed to warm to room temperature and stirred for 3.5 h. The mixture was evaporated, the residue was dissolved in ethyl acetate and washed twice with 2N hydrochloric acid and once with brine. The organic layer was dried over sodium sulphate and evaporated to dryness to give the crude product, that was purified by silica gel chromatography (heptanes:ethyl acetate) to give 86 mg of isomer 1 (11) and 105 mg of isomer 2 (12). The relative stereochemistry was not assigned. $R_t$=1.61 min (11), 1.57 min (12) (Method B). Detected mass: 274.2 (M+H$^+$).

c) 4-(1-Amino-propyl)-4-benzyl-cyclohexanol (13 and 14)

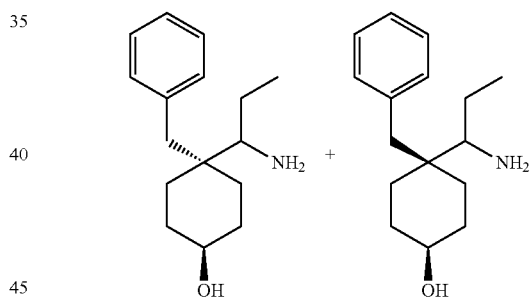

86 mg of 11 were dissolved in 2 mL of isopropanol and 1 mL of 6M hydrochloric acid in isopropanol was added. The mixture was allowed to stir overnight, then water was added and isopropanol was removed in vacuo. The mixture was lyophilized from water three times to give 66 mg of 13 as the hydrochloride. The relative stereochemistry was not assigned. $R_t$=2.34 min (Method A). Detected mass: 248.2 (M+H$^+$). The other isomer (14) was prepared accordingly, starting from 12. $R_t$=2.34 min (Method A). Detected mass: 248.2 (M+H$^+$).

The following products were synthesized as hydrochlorides in a similar fashion as described for the synthesis of Example 1 (Step d and e) starting from the respective aminoalcohols (prepared following the procedure described for the synthesis of 13 and 14) and a suitably protected 7-chloro-6-fluoro-isoquinoline. If the diastereoisomers could not be separated at an earlier stage of the synthesis, the deprotected products were purified by preparative HPLC and lyophilized from 1N HCl and water, subsequently.

| Ex.-No. | Product | Isomer | Chemical Name | [M + H⁺] | R_f [min] | Method |
|---|---|---|---|---|---|---|
| 26 | | 1 | 6-[4-(1-Amino-propyl)-4-methyl-cyclohexyloxy]-7-chloro-2H-isoquinolin-1-one | 349.2 | 2.76 | D |
| 27 | | 2 | 6-[4-(1-Amino-propyl)-4-methyl-cyclohexyloxy]-7-chloro-2H-isoquinolin-1-one | 349.3 | 2.77 | D |
| 28 | | 1 | 6-[4-(1-Amino-propyl)-4-isobutyl-cyclohexyloxy]-7-chloro-2H-isoquinolin-1-one | 391.3 | 2.73 | C |
| 29 | | 2 | 6-[4-(1-Amino-propyl)-4-isobutyl-cyclohexyloxy]-7-chloro-2H-isoquinolin-1-one | 391.2 | 2.67 | A |
| 30 | | 1 | 6-[4-(1-Amino-propyl)-4-benzyl-cyclohexyloxy]-7-chloro-2H-isoquinolin-1-one | 425.2 | 3.20 | D |
| 31 | | 2 | 6-[4-(1-Amino-propyl)-4-benzyl-cyclohexyloxy]-7-chloro-2H-isoquinolin-1-one | 425.1 | 2.76 | A |

Alternative Preparation of Example 26

6-[4-(1-Amino-propyl)-4-methyl-cyclohexyloxy]-7-chloro-2H-isoquinolin-1-one a) 1-Methyl-4-oxo-cyclohexanecarbonitrile (15)

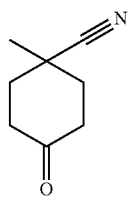

5 g of 8-Methyl-1,4-dioxa-spiro[4.5]decane-8-carbonitrile, prepared from 1,4-dioxa-spiro[4.5]decane-8-carbonitrile and methyl iodide in a similar fashion as described for 5, were dissolved in 100 mL of acetone. 25 mL of 1N HCl were added and the mixture was allowed to stir until conversion was complete. Additional conc. HCl was added over the course of the reaction. The mixture was neutralized by addition of saturated sodium bicarbonate solution and extracted three times with ethyl acetate.

The combined organic layer was washed with brine, dried over sodium sulphate and evaporated to dryness. The crude material was purified by silica gel filtration to give 3.75 g of the desired product.

Alternatively the compound could be obtained by heating 14.2 g of 8-methyl-1,4-dioxa-spiro[4.5]decane-8-carbonitrile in 190 mL of 80% acetic acid under reflux until conversion was complete. The mixture was cooled and poured onto 1.2 L of cold, saturated sodium bicarbonate solution. 600 mL of brine were added and the mixture was extracted several times with ethyl acetate. The combined ethyl acetate layers were washed with brine, dried over magnesium sulphate and evaporated. The residue was taken up in water and acetonitrile and lyophilized to give 6.75 g of the desired product, that could be directly used in further conversions.

$R_t$=0.63 min (Method B). Detected mass: 138.2 (M+H$^+$).

b) cis-4-Hydroxy-1-methyl-cyclohexanecarbonitrile (16)

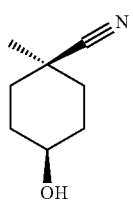

1 g of 15 were dissolved in 50 mL of ethanol and 303 mg of sodium borohydride were added portionswise at −65° C. The mixture was allowed to stir until conversion was complete, 150 mL of water were added and pH was adjusted to 2 by addition of 2N hydrochloric acid. The aqueous layer was extracted three times with ethyl acetate, the combined organic layers were washed with brine, dried over sodium sulphate and evaporated. The residue was purified by silica gel chromatography to give 840 mg of 16 as a single isomer. $R_t$=0.70 min (Method B). Detected mass: 140.1 (M+H$^+$).

c) cis-4-(1-Amino-propyl)-4-methyl-cyclohexanol (17)

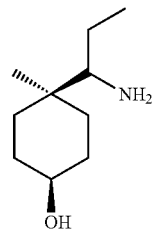

400 mg of 16 was dissolved in 6 mL of a 3M solution of ethyl magnesium chloride in diethylether and heated under reflux for 4 h. The mixture was cooled to room temperature, diluted by addition of 200 mL of THF and filtered over celite. The filter cake was washed with THF. The mixture was evaporated and the residue taken up in 50 mL of ethanol. 217 mg of sodium borohydride was added and the mixture was allowed to stir until conversion was complete. The mixture was evaporated and taken up in 50 mL of 1N HCl. The aqueous layer was extracted with ethyl acetate and the ethyl acetate layer extracted with 30 mL of 1N HCl. The combined aqueous layer was adjusted to alkaline pH by addition of 5M sodium hydroxide solution and extracted twice with methyl tert. butyl ether. The combined ether layers were washed with brine, dried over sodium sulphate and evaporated to dryness to give 225 mg of 17. $R_t$=0.47 min (Method B). Detected mass: 172.2 (M+H$^+$).

d) cis-1-[4-(1-Benzyloxy-7-chloro-isoquinolin-6-yloxy)-1-methyl-cyclohexyl]-propylamine (18)

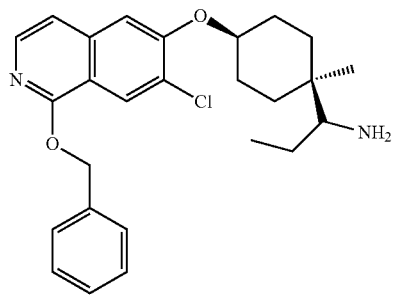 [SMILES: CCC(N)[C@]1(C)CC[C@H](Oc2cc3ccnc(OCc4ccccc4)c3cc2Cl)CC1]

224 mg of 17 were codistilled twice with toluene, dissolved in 13 mL of dry dimethyl acetamide and 132 mg of 95% sodium hydride were added. The mixture was allowed to stir for ten minutes. 414 mg of 1-benzyloxy-7-chloro-6-fluoro-isoquinoline (1) were added and the mixture was stirred under argon for 3 h at 50° C. Stirring was continued overnight at room temperature. Water was cautiously added (ca. 20 mL). The mixture was extracted several times with a mixture of dichloromethane and isopropanol (3:1). The combined organic layer was washed three times with water and with brine, dried over sodium sulphate and evaporated. Water was added to the remainder and the mixture was lyophilized. The crude product was subjected to silica gel chromatography (dichloromethane:methanol) to yield 395 mg of the desired product. $R_t$ 1.40 min (Method B). Detected mass: 439.2 (M+H$^+$).

e) cis-6-[4-(1-Amino-propyl)-4-methyl-cyclohexyloxy]-7-chloro-2H-isoquinolin-1-one (Example 26)

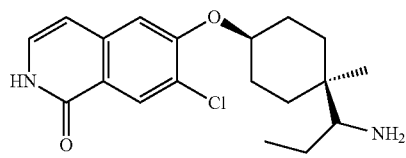 [SMILES: CCC(N)[C@]1(C)CC[C@H](Oc2cc3cc[nH]c(=O)c3cc2Cl)CC1]

400 mg of 18 were dissolved in 10 mL of isopropanol/1N HCl (1:1). The mixture was stirred at room temperature until complete conversion was observed. The reaction mixture was evaporated and lyophilized from water twice to give 300 mg of the title compound Example 26 as its hydrochloride. $R_t$=2.37 min (Method A). Detected mass: 349.2 (M+H$^+$).

The obtained product was assigned by NMR spectroscopy to be the cis product. Therefore, it was concluded, that compounds 16 to 18 also exist in their cis-form.

The following products were synthesized as hydrochlorides in a similar fashion as described for the alternative synthesis of Example 26 starting from the respective aminoalcohols (prepared following the procedure described for the synthesis of 17) and a suitably protected 6-fluoro-isoquinoline. In case of Example 38, liberation of the final product was achieved by heating the protected isoquinoline derivative, obtained as described above, in a mixture of isopropanol/1N hydrochloric acid for 1 h at 100° C. in a microwave oven, workup was performed in an analogous fashion as described in the procedure above (e.g. for Example 26, step e).

| Ex.-No. | Product | Building block | Chemical Name | [M + H$^+$] | $R_t$/[min] | Method |
|---|---|---|---|---|---|---|
| 34 | | 1 | cis-6-[4-(1-Amino-propyl)-4-ethyl-cyclohexyloxy]-7-chloro-2H-isoquinolin-1-one | 363.2 | 2.42 | A |
| 35 | | 1 | cis-6-[4-(1-Amino-butyl)-4-isopropyl-cyclohexyloxy]-7-chloro-2H-isoquinolin-1-one | 391.1 | 1.12 | B |
| 36 | | 3 | cis-6-[4-(1-Amino-butyl)-4-ethyl-cyclohexyloxy]-7-methyl-2H-isoquinolin-1-one | 357.2 | 1.08 | B |
| 37 | | 3 | cis-6-[4-(1-Amino-ethyl)-4-ethyl-cyclohexyloxy]-7-methyl-2H-isoquinolin-1-one | 329.2 | 0.98 | B |
| 38 | | 4 | cis-6-[4-(1-Amino-propyl)-4-butyl-cyclohexyloxy]-7-chloro-2H-isoquinolin-1-one | 391.2 | 1.10 | B |

| Ex.-No. | Product | Building block | Chemical Name | [M + H⁺] | R$_f$/ [min] | Method |
|---|---|---|---|---|---|---|
| 39 | | 2 | cis-6-[4-(1-Amino-propyl)-4-butyl-cyclohexyloxy]-4-benzyl-7-chloro-2H-isoquinolin-1-one | 481.3 | 1.25 | B |
| 49 | | 37 | cis-6-[4-(1-Amino-propyl)-4-ethyl-cyclohexyloxy]-7-methoxy-2H-isoquinolin-1-one | 359.2 | 1.25 | G |
| 50 | | 33 | cis-6-[4-(1-Amino-propyl)-4-ethyl-cyclohexyloxy]-7-fluoro-2H-isoquinolin-1-one | 347.2 | 1.25 | G |
| 51 | | 34 | cis-6-[4-(1-Amino-propyl)-4-ethyl-cyclohexyloxy]-7-fluoro-5-methyl-2H-isoquinolin-1-one | 361.2 | 1.29 | G |
| 52 | | 35 | cis-6-[4-(1-Amino-propyl)-4-ethyl-cyclohexyloxy]-7-methyl-2H-isoquinolin-1-one | 343.2 | 1.29 | G |

| Ex.-No. | Product | Building block | Chemical Name | [M + H⁺] | $R_t$ [min] | Method |
|---|---|---|---|---|---|---|
| 53 | | 26 | cis-1-[4-(5,7-Dimethyl-isoquinolin-6-yloxy)-1-ethyl-cyclohexyl]-propylamine | 341.2 | 1.21 | G |
| 54 | | 36 | cis-6-[4-(1-Amino-propyl)-4-ethyl-cyclohexyloxy]-5,7-dimethyl-2H-isoquinolin-1-one | 357.3 | 1.29 | G |
| 55 | | 27 | cis-1-[1-Ethyl-4-(7-fluoro-isoquinolin-6-yloxy)-cyclohexyl]-propylamine | 331.2 | 1.17 | G |
| 56 | | 3 | cis-1-[1-Ethyl-4-(7-methyl-isoquinolin-6-yloxy)-cyclohexyl]-propylamine | 327.2 | 1.19 | G |
| 57 | | 25 | cis-1-[1-Ethyl-4-(7-fluoro-5-methyl-isoquinolin-6-yloxy)-cyclohexyl]-propylamine | 345.2 | 1.13 | G |

Example 58 cis-6-[4-(1-Amino-propyl)-4-methoxy-cyclohexyloxy]-7-chloro-2H-isoquinolin-1-one a) (4,4-Dimethoxy-cyclohexyloxymethyl)-benzene (38)

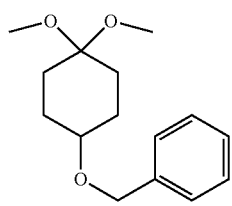 [SMILES: COC1(OC)CCC(OCc2ccccc2)CC1]

529 mL of trimethyl orthoformate and 32 mg of p-toluene sulfonic acid were added to a solution of 4-benzyloxy cyclohexanone in 20 mL of dry methanol and the mixture was stirred overnight. 20 mL of saturated aqueous sodium bicarbonate solution and 20 mL of dichloromethane were added, the aqueous layer was extracted several times with dichloromethane and the combined organic layers were dried and evaporated to dryness to yield 1.50 g of the desired product, which was used without further purification.

b) 4-Benzyloxy-1-methoxy-cyclohexanecarbonitrile (39)

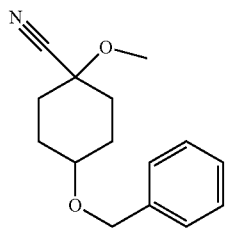 [SMILES: COC1(C#N)CCC(OCc2ccccc2)CC1]

1.5 g of (4,4-Dimethoxy-cyclohexyloxymethyl)-benzene (38) were dissolved in 20 mL of dry dichloromethane and cooled to 0° C. 3.05 mL of trimethylsilyl cyanide were added dropwise and after stirring for 2 minutes, 1.31 mL of trimethylsilyl trifluoromethansulfonate were added dropwise. The mixture was stirred at 0° C. for 2 h, then 20 mL of saturated aqueous sodium bicarbonate solution were added dropwise. Phases were separated and the aqueous layer was extracted several times with dichloromethane. The combined organic layer was dried and evaporated to dryness to give 1.5 g of crude product, that was purified by silica gel chromatography to give 1.3 g of the desired compound as a cis-trans-mixture. $R_t$=4.68 min (Method D). Detected mass: 246.1 (M+H$^+$).

c) 1-(4-Benzyloxy-1-methoxy-cyclohexyl)-propylamine (40)

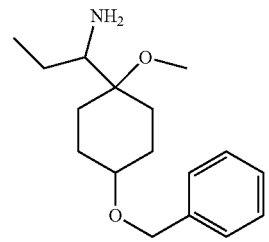 [SMILES: CCC(N)C1(OC)CCC(OCc2ccccc2)CC1]

Under argon, 1.2 g of 39 were dissolved in 60 mL of absolute toluene. Then, 2.9 mL of ethylmagnesium bromide (3M in diethylether) were added dropwise. The mixture was allowed to warm to room temperature. After conversion was complete, the reaction mixture was cooled to 5° C. and 2 mL of dry ethanol were added. The mixture was filtered over celite and the filter cake was washed with tetrahydrofuran. Volatiles were removed in vacuo, the residue was dissolved in 20 mL of dry ethanol, 331 mg of sodium borohydride were added and the mixture was stirred for 2 h at 0° C. The mixture was evaporated, 20 mL of methyl tert.butyl ether and 20 mL of water were added and 1N aqueous hydrochloric acid was added dropwise until gas evolution ceased. The organic layer was separated, washed with brine, dried and evaporated to give 1 g of the desired product as a cis/trans mixture. $R_t$=0.96/0.99 min (Method M). Detected mass: 278.3 (M+H$^+$).

d) 4-(1-Amino-propyl)-4-methoxy-cyclohexanol (41)

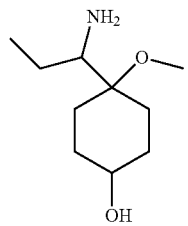

35 mL of ammonia were condensed into a Schlenk flask, cooled in a dryice-isopropanol bath. 170 mg of sodium were dissolved and 1.1 g of 40, dissolved in 3 mL of dry tetrahydrofurane, were added. After complete conversion, the reaction was quenched by addition of methanol and the mixture was warmed to room temperature. The solvents were evaporated and the crude material was taken up in methanol and dilute hydrochloric acid and evaporated several times to give 1.19 g of crude product as a cis/trans mixture, which was used directly in the next step, $R_t$=0.10 min (Method P). Detected mass: 188.1 (M+H$^+$).

e) 1-[4-(7-Chloro-1-methoxy-isoquinolin-6-yloxy)-1-methoxy-cyclohexyl]-propylamine (42 and 43)

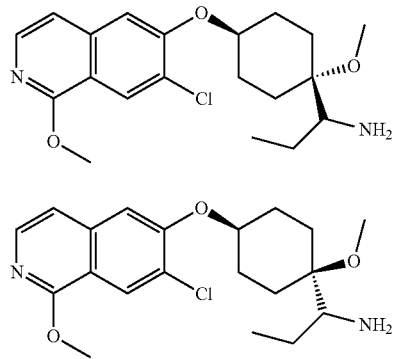

650 mg of 41 were dissolved in 40 mL of dry dimethyl acetamide. The mixture was cooled to 0° C. and 369 mg of sodium hydride (60% in mineral oil) were added. After stirring for 10 minutes, 536 mg of 7-chloro-6-fluoro-1-methoxy-isoquinoline (4) were added and the mixture was heated to 50° C. Stirring was continued first at room temperature until the reaction went to completion, small additional amounts of isoquinoline were added, if necessary. The mixture was cooled to room temperature and 50 mL of water and 50 mL of dichloromethane:isopropanol (3:1) were added. The organic layer was washed twice with water, dried over sodium sulphate and evaporated. The obtained crude product was purified by flash chromatography to yield 100 mg of 42, 330 mg of 43 and 130 mg of a mixture of the two. 42: $R_t$=1.03 min (Method M). Detected mass: 379.2 (M+H$^+$). 43: $R_t$=1.04 min (Method M). Detected mass: 379.2 (M+H$^+$).

f) cis-6-[4-(1-Amino-propyl)-4-methoxy-cyclohexyloxy]-7-chloro-2H-isoquinolin-1-one (Example 58)

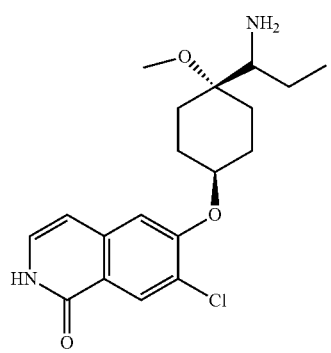 [SMILES: CCC(N)[C@]1(OC)CC[C@H](Oc2cc3cc[nH]c(=O)c3cc2Cl)CC1]

A solution of 100 mg of 42 was dissolved in 8 mL of 2-propanol/1N aqueous hydrochloric acid (1:1) and heated in the microwave oven for 10 min at 120° C. The reaction mixture was evaporated and lyophilized from water twice to give 100 mg of the title compound (Example 58) as its hydrochloride. $R_t$=124 min (Method G). Detected mass: 365.2 (M+H$^+$).

Example 59 trans-6-[4-(1-Amino-propyl)-4-methoxy-cyclohexyloxy]-7-chloro-2H-isoquinolin-1-one

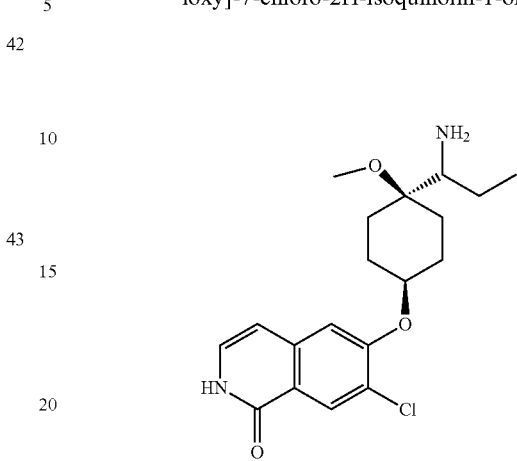

trans-6-[4-(1-Amino-propyl)-4-methoxy-cyclohexyloxy]-7-chloro-2H-isoquinolin-1-one (Example 59) was obtained from 43 by a similar reaction as described for Example 58. $R_t$=1.22 min (Method G). Detected mass: 365.2 (M+H$^+$).

Example 60

6-[4-(1-Amino-propyl)-4-ethoxy-cyclohexyloxy]-7-chloro-2H-isoquinolin-1-one

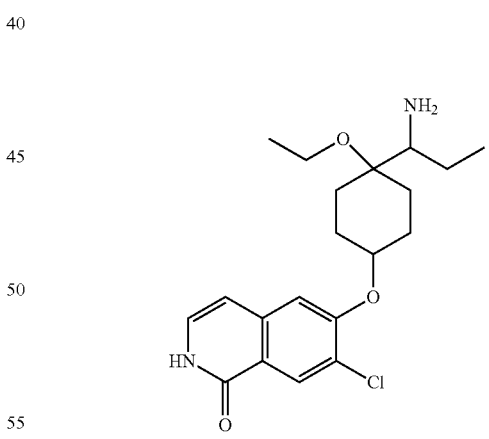

6-[4-(1-Amino-propyl)-4-ethoxy-cyclohexyloxy]-7-chloro-2H-isoquinolin-1-one (Example 60) was obtained following a similar reaction sequence as described for synthesis of Example 58, starting from 4-benzyloxy cyclohexanone and using triethyl orthoformate instead of trimethyl orthoformate in step a. In this case, the isomers could not be separated at the protected stage, the product was obtained as a cis/trans mixture. $R_t$=1.27 min (Method C). Detected mass: 379.2 (M+H$^+$).

Alternative Preparation of Example 1 cis-6-[4-(1-amino-propyl)-4-(tetrahydropyran-4-yl)cyclohexyloxy]-7-chloro-2H-isoquinolin-1-one a) 4-Oxo-1-(tetrahydro-pyran-4-yl)-cyclohexanecarbonitrile (44)

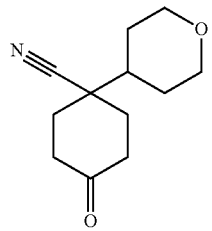

A solution of 10.3 g (40.8 mmol) of 8-(tetrahydropyran-4-yl)-1,4-dioxa-spiro[4.5]decane-8-carbonitrile (5) in a mixture of 90 mL of acetic acid and 18 mL of water was heated at 100° C. for 24 h. The mixture was cooled to room temperature and slowly poured onto 1.2 L of cold saturated aqueous sodium bicarbonate solution. The mixture was diluted with 600 mL of brine and extracted six times with methyl-tert-butyl ether. The combined organic phases were washed with water and brine, dried over magnesium sulphate, filtered and concentrated in vacuo. The residue was lyophilized from acetonitrile and water, taken up in water and lyophilized again to give 5.95 g of the ketone, which was used directly in the next step. $R_t$=0.82 min (Method O). Detected mass: 208.1 (M+H$^+$).

b) cis-4-(tert-Butyl-dimethyl-silanyloxy)-1-(tetrahydro-pyran-4-yl)-cyclohexane-carbonitrile (45)

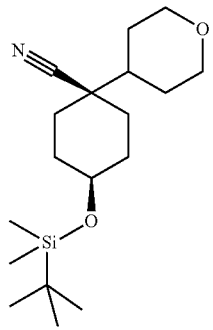 [SMILES: CC(C)(C)[Si](C)(C)O[C@H]1CC[C@](C#N)(C2CCOCC2)CC1]

5.95 g (28.7 mmol) of the ketone 44 were dissolved in 85 mL of absolute ethanol, cooled to −70° C. and 1.20 g (31.6 mmol) of sodium borohydride were added portionwise. The reaction mixture was allowed to slowly warm to room temperature and was stirred to 17 h. After the reaction went to completion, the reaction mixture was diluted with 150 mL of water, the pH was adjusted to pH 2 with 2N aqueous hydrochloric acid and the mixture was extracted three times with ethyl acetate. The combined organic phases were washed with brine, dried over magnesium sulphate, filtered and concentrated in vacuo to give 4.5 g of the alcohol which was used directly in the next step.

3.00 g (14.3 mmol) of the alcohol were dissolved in 15 mL of absolute dichloromethane, cooled to 0° C. and treated with 4.17 mL (3.84 g, 35.8 mmol) of 2,6-lutidine and 3.95 mL (4.55 g, 17.2 mmol) of tert.-butyldimethylsilyl-trifluoromethansulfonate. The mixture was stirred at room temperature overnight. The reaction mixture was diluted with 50 mL of dichloromethane, washed twice with 50 mL of water, twice with 0.1N hydrochloric acid (50 mL each), twice with saturated aq. sodium bicarbonate solution and once with 50 mL of brine, dried over magnesium sulphate, evaporated to dryness and purified by silica gel chromatography (heptanes:ethylacetate) to give 2.12 g of the desired product. R=1.21 min (Method P). Detected mass: 324.4 (M+H$^+$).

c) cis-4-(1-Aminopropyl)-4-(tetrahydropyran-4-yl)-cyclohexanol (46)

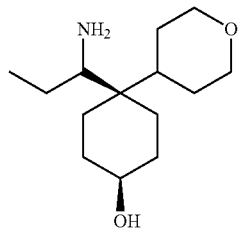 [SMILES: CCC(N)[C@]1(C2CCOCC2)CC[C@H](O)CC1]

Under argon, 400 mg (1.24 mmol) of 4-(tert-butyl-dimethyl-silanyloxy)-1-(tetrahydro-pyran-4-yl)-cyclohexane-carbonitrile (45) were dissolved in 0.5 mL of absolute toluene. Then, 618 µL (1.85 mmol) of ethylmagnesium bromide (3M in diethylether) were added dropwise and the reaction mixture was heated to 90° C. After 16 h, an additional 200 µL of ethylmagnesium bromide (3M in diethylether) were added and stirring was continued until the reaction went to completion. The reaction mixture was cooled to room temperature and 3 mL of dry methanol were added. After a period of 10 min, 93.1 mg (2.46 mmol) of sodium borohydride were added and the mixture was stirred for 16 h at room temperature. The reaction was quenched by addition of 50 mL of 1M aqueous sodium hydroxide solution and extracted twice with diethylether (60 mL each).

The combined organic phases were treated with 120 mL of 2N aqueous hydrochloric acid. The biphasic system was stirred vigourously at room temperature for 18 h. The phases were separated, and the organic phase was extracted with 60 mL of 2N aqueous hydrochloric acid. The combined aqueous layer was washed with 50 mL of ethyl acetate, adjusted to pH 12 by addition of 5N sodium hydroxide solution and extracted twice with a 3:1 mixture of dichloromethane and 2-propanol (80 mL each). The combined organic layers were evaporated to give 115 mg of the desired product, which was used directly in the next step. $R_t$=0.65 min (Method O). Detected mass: 242.2 (M+H$^+$).

d) cis-1-[4-(7-Chloro-1-methoxy-isoquinolin-6-yloxy)-1-(tetrahydro-pyran-4-yl)-cyclohexyl]-propylamine (47)

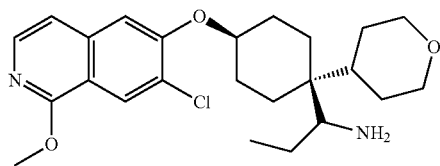 [SMILES: CCC(N)[C@]1(C2CCOCC2)CC[C@H](Oc2cc3ccnc(OC)c3cc2Cl)CC1]

To a suspension of sodium hydride (60%, 369 mg, 9.22 mmol, 3 eq.) in dimethyl acetamide (8 mL) was added a solution of cis-4-(1-aminopropyl)-4-(tetrahydropyran-4-yl)- cyclohexanol (46, 619 mg, 3.38 mmol, 1.1 eq.) in dimethyl acetamide (8 mL). After stirring for 60 min at room temperature a solution of 1-methoxy-7-chloro-6-fluoro-isoquinoline (4, 650 mg, 3.07 mmol) in dimethyl acetamide (8 mL) was added and stirring was continued at room temperature until the reaction went to completion. The reaction was concentrated in vacuo and quenched by addition of water (50 mL). The reaction mixture was extracted three times with 50 mL of a mixture of dichloromethane and 2-propanol (3:1). The combined organic layers were evaporated, and the obtained crude product was purified by flash chromatography (SiO$_2$, 0%→30% methanol in dichloromethane) to yield 701 mg of 47 as racemate. $R_t$=0.74 min (Method P). Detected mass: 433.3 (M+H$^+$).

e) cis-6-[4-(1-Aminopropyl)-4-(tetrahydropyran-4-yl)-cyclohexyloxy]-7-chloro-2H-isoquinolin-1-one (Example 1)

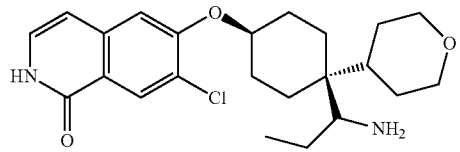 [SMILES: CCC(N)[C@]1(C2CCOCC2)CC[C@H](Oc2cc3cc[nH]c(=O)c3cc2Cl)CC1]

A solution of 1-[(cis-4-(7-chloro-1-methoxy-isoquinolin-6-yloxy)-1-(tetrahydro-pyran-4-yl)-cyclohexyl]propylamine (47, 701 mg, 1.62 mmol) in 2-propanol (2 mL) was treated with 1N aqueous hydrochloric acid (2 mL) and heated in the microwave, first for 20 min at 100° C., then for 5 min at 120° C. when complete conversion was observed. The reaction mixture was evaporated and lyophilized from water twice to give 653 mg of the title compound (Example 1) as its hydrochloride. $R_t$=2.34 min (Method C). Detected mass: 419.2 (M+H$^+$).

Alternative Preparation of Example 34 cis-6-[4-(1-Amino-propyl)-4-ethyl-cyclohexyloxy]-7-chloro-2H-isoquinolin-1-one a) cis-1-[4-(7-Chloro-1-methoxy-isoquinolin-6-yloxy)-1-ethyl-cyclohexyl]propylamine (48)

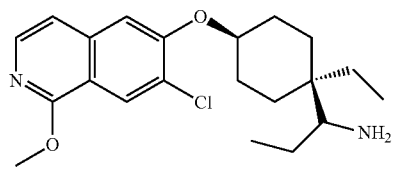 [SMILES: CCC(N)[C@]1(CC)CC[C@H](Oc2cc3ccnc(OC)c3cc2Cl)CC1]

Following the procedure described for the alternative synthesis of Example 1 (Step d), 1.47 g of (48) were synthesized starting from 1.16 g (5.50 mmol) of 7-chloro-6-fluoro-1-methoxy-isoquinoline, 927 mg (5.0 mmol) of cis-4-(1-amino-propyl)-4-ethyl-cyclohexanol (prepared from 8-ethyl-1,4-dioxa-spiro[4.5]decane-8-carbonitrile and ethylmagnesium bromide using a protocol similar to the one described for the synthesis of (46) and 450 mg (15.0 mmol) of sodium hydride (80% in mineral oil). $R_t$=0.76 min (Method P). Detected mass: 377.4 (M+H$^+$).

b) cis-6-[4-(1-Amino-propyl)-4-ethyl-cyclohexyloxy]-7-chloro-2H-isoquinolin-1-one (Example 34)

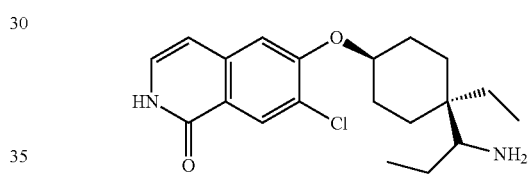

1.25 g of cis-6-[4-(1-Amino-propyl)-4-ethyl-cyclohexyloxy]-7-chloro-2H-isoquinolin-1-one (Example 34) were synthesized as hydrochloride in a similar fashion as described for the alternative synthesis of Example 1 (Step e) starting from 1.47 g of cis-1-[4-(7-chloro-1-methoxy-isoquinolin-6-yloxy)-1-ethyl-cyclohexyl]-propylamine (48). $R_t$=2.43 min (Method C). Detected mass: 363.2 (M+H$^+$).

The following products were synthesized as hydrochlorides in a similar fashion as described for the alternative synthesis of Example 1 (Step d and e) starting from the respective aminoalcohols (prepared following the procedure described for the synthesis of 46) and a suitably protected 6-fluoro-isoquinoline.

| Ex.-No. | Product | Building block | Chemical Name | [M + H$^+$] | $R_t$/[min] | Method |
|---|---|---|---|---|---|---|
| 61 | | 1 | cis-6-[4-(Amino-phenyl-methyl)-4-methyl-cyclohexyloxy]-7-chloro-2H-isoquinolin-1-one | 397.2 | 2.42 | A |

| Ex.-No. | Product | Building block | Chemical Name | [M + H⁺] | $R_t$/[min] | Method |
|---|---|---|---|---|---|---|
| 62 | | 1 | cis-6-[4-(1-Amino-butyl)-4-methyl-cyclohexyloxy]-7-chloro-2H-isoquinolin-1-one | 363.2 | 1.76 | N |
| 63 | | 1 | cis-6-[4-(Amino-phenyl-methyl)-4-cyclopropyl methyl-cyclohexyloxy]-7-chloro-2H-isoquinolin-1-one | 437.2 | 2.14 | H |
| 64 | | 1 | cis-6-[4-(1-Amino-3-methyl-butyl)-4-cyclopropyl-methyl-cyclohexyloxy]-7-chloro-2H-isoquinolin-1-one | 417.2 | 1.92 | J |
| 65 | | 4 | cis-6-[4-(1-Amino-2-methyl-propyl)-4-cyclohexyl-cyclohexyloxy]-7-chloro-2H-isoquinolin-1-one | 417.2 | 1.99 | K |
| 66 | | 4 | cis-6-[4-(1-Amino-propyl)-4-(4,4,4-trifluoro-butyl)-cyclohexyloxy]-7-chloro-2H-isoquinolin-1-one | 445.1 | 1.91 | K |
| 67 | | 4 | cis-6-[4-(1-Amino-propyl)-4-(tetrahydro-pyran-4-ylmethyl)-cyclohexyloxy]-7-chloro-2H-isoquinolin-1-one | 433.2 | 1.74 | K |

-continued

| Ex.-No. | Product | Building block | Chemical Name | [M + H⁺] | $R_t$/[min] | Method |
|---|---|---|---|---|---|---|
| 68 | | 4 | cis-6-[4-(Amino-cyclopropyl-methyl)-4-(tetrahydro-pyran-4-ylmethyl)-cyclohexyloxy]-7-chloro-2H-isoquinolin-1-one | 445.2 | 1.76 | K |
| 69 | | 4 | cis-6-[4-(Amino-cyclopropyl-methyl)-4-methyl-cyclohexyloxy]-7-chloro-2H-isoquinolin-1-one | 361.2 | 1.73 | K |
| 70 | | 4 | cis-6-[4-(Amino-cyclopropyl-methyl)-4-ethyl-cyclohexyloxy]-7-chloro-2H-isoquinolin-1-one | 375.2 | 1.74 | K |
| 71 | | 4 | cis-6-[4-(1-Amino-propyl)-4-ethoxy methyl-cyclohexyloxy]-7-chloro-2H-isoquinolin-1-one | 393.1 | 1.78 | N |
| 72 | | 4 | cis-6-[4-(1-Amino-ethyl)-4-cyclopropyl-cyclohexyloxy]-7-chloro-2H-isoquinolin-1-one | 361.2 | 1.65 | N |
| 73 | | 4 | cis-6-[4-(Amino-cyclopropyl-methyl)-4-(4,4,4-trifluoro-butyl)-cyclohexyloxy]-7-chloro-2H-isoquinolin-1-one | 457.2 | 1.89 | N |
| 74 | | 4 | cis-6-[4-(1-Amino-propyl)-4-cyclopropyl-cyclohexyloxy]-7-chloro-2H-isoquinolin-1-one | 375.2 | 1.73 | N |
| 75 | | 4 | cis-6-[4-(Amino-cyclopropyl-methyl)-4-cyclopropyl-cyclohexyloxy]-7-chloro-2H-isoquinolin-1-one | 387.2 | 1.76 | N |

-continued

| Ex.-No. | Product | Building block | Chemical Name | [M + H+] | R$_t$/[min] | Method |
|---|---|---|---|---|---|---|
| 76 | | 4 | cis-6-[4-(1-Amino-propyl)-4-(tetrahydro-thiopyran-4-yl)-cyclohexyloxy]-7-chloro-2H-isoquinolin-1-one | 434.2 | 1.24 | L |
| 77 | | 4 | cis-6-[4-(1-Amino-ethyl)-4-propyl-cyclohexyloxy]-7-chloro-2H-isoquinolin-1-one | 363.3 | 2.48 | C |
| 78 | | 33 | cis-6-[4-(1-Amino-ethyl)-4-ethyl-cyclohexyloxy]-7-fluoro-2H-isoquinolin-1-one | 333.3 | 1.19 | J |
| 79 | | 34 | cis-6-[4-(1-Amino-ethyl)-4-ethyl-cyclohexyloxy]-7-fluoro-5-methyl-2H-isoquinolin-1-one | 347.3 | 1.24 | G |
| 80 | | 25 | cis-1-[1-Ethyl-4-(7-fluoro-5-methyl-isoquinolin-6-yloxy)-cyclohexyl]-ethylamine | 331.3 | 0.80 | M |
| 81 | | 2 | cis-6-[4-(1-Amino-ethyl)-4-ethyl-cyclohexyloxy]-4-benzyl-7-chloro-2H-isoquinolin-1-one | 439.2 | 1.42 | G |
| 82 | | 28 | cis-1-[4-(7-Bromo-isoquinolin-6-yloxy)-1-ethyl-cyclohexyl]-ethylamine | 377.1 | 1.11 | G |
| 83 | | 30 | cis-1-[4-(7-Methyl-isoquinolin-6-yloxy)-1-ethyl-cyclohexyl]-ethylamine | 313.2 | 1.10 | G |

| Ex.-No. | Product | Building block | Chemical Name | [M + H⁺] | $R_t$/[min] | Method |
|---|---|---|---|---|---|---|
| 84 | 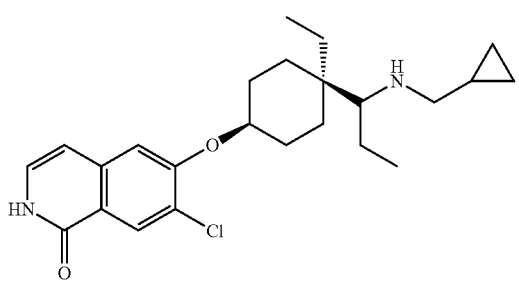 [SMILES: CCC(NCC1CC1)[C@]1(CC)CC[C@H](Oc2cc3cc[nH]c(=O)c3cc2Cl)CC1] | 5-Chloro-6-fluoro-isoquinoline | cis-1-[4-(5-Chloro-isoquinolin-6-yloxy)-1-ethyl-cyclohexyl]-ethylamine | 333.2 | 1.12 | G |

Example 85 cis-7-Chloro-6-{4-[1-(cyclopropylmethyl-amino)-propyl]-4-ethyl-cyclohexyloxy}-2H-isoquinolin-1-one 100 mg of Example 34 were dissolved in 1.5 mL of methanol, 69 µL of triethylamine, 143 µL of acetic acid, 100 mg of powdered molecular sieves and 56 µL of cyclopropane carboxaldehyde were added and the mixture was allowed to stir for 1 h. 47 mg of sodium cyanoborohydride were added and the mixture was stirred at 40° C. until the reaction went to completion. The reaction mixture was diluted with 10 mL of methanol, filtered and the solution was evaporated to dryness. The residue was dissolved in 50 mL of saturated sodium bicarbonate solution and extracted with dichloromethane. The organic layer was dried over magnesium sulphate, evaporated and the crude material was purified by reversed-phase HPLC (water:acetonitril) to yield 95 mg of the desired product as trifluoroacetic acid salt. $R_t$=1.39 min (Method G). Detected mass: 417.2 (M+H⁺).

The following examples were obtained in a similar fashion as described for Example 85, using Example 34 and the respective aldehydes as starting materials:

| Ex.-No. | Product | Aldehyde | Chemical Name | [M + H⁺] | $R_t$/[min] | Method |
|---|---|---|---|---|---|---|
| 86 | | Benzaldehyde | cis-6-[4-(1-Benzylamino-propyl)-4-ethyl-cyclohexyloxy]-7-chloro-2H-isoquinolin-1-one | 453.2 | 1.44 | G |
| 87 | | Isobutyl-aldehyde | cis-7-Chloro-6-[4-ethyl-4-(1-isobutyl amino-propyl)-cyclohexyloxy]-2H-isoquinolin-1-one | 419.2 | 1.41 | G |

| Ex.-No. | Product | Aldehyde | Chemical Name | [M + H⁺] | R$_f$ [min] | Method |
|---|---|---|---|---|---|---|
| 88 | 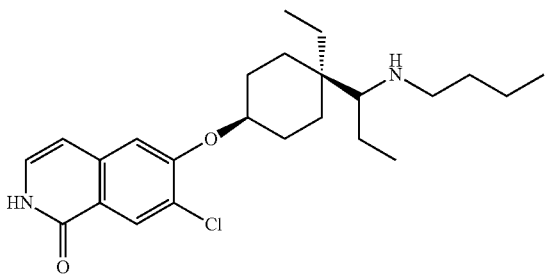 [SMILES: CCCCNC(CC)[C@]1(CC)CC[C@H](Oc2cc3cc[nH]c(=O)c3cc2Cl)CC1] | Butanal | cis-6-[4-(1-Butylamino-propyl)-4-ethyl-cyclohexyloxy]-7-chloro-2H-isoquinolin-1-one | 419.2 | 1.40 | G |

Synthesis of 4-(1-Amino-2,2,2-trifluoro-ethyl)-4-cyclopropylmethyl-cyclohexanol (21)

a) 2-Methyl-propane-2-sulfinic acid 1-(8-cyclopropylmethyl-1,4-dioxa-spiro[4.5]dec-8-yl)-methylideneamide (19)

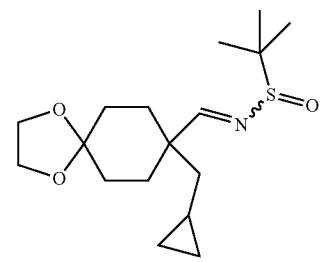 [SMILES: CC(C)(C)S(=O)N=CC1(CC2CC2)CCC2(CC1)OCCO2]

To a solution of 8-cyclopropylmethyl-1,4-dioxa-spiro[4.5]decane-8-carbonitrile, prepared from 1,4-dioxa-spiro[4.5]decane-8-carbonitrile and cyclopropylmethyl bromide in a similar fashion as described for 5, (3.00 g, 13.6 mmol) in tetrahydrofuran (40 mL) at −78° C. was added a 1M solution of diisobutylaluminium hydride in toluene (20.3 mL, 20.3 mmol, 1.5 eq.) and the reaction was allowed to warmed to 0° C. over a period of 3 h. The mixture was recooled to −78° C., neutralized by dropwise addition of a 10% aqueous citric acid solution and warmed to room temperature. The mixture was partitioned between methyl-tert.butyl ether and water, the aqueous phase extracted twice with methyl-tert.butyl ether and the combined organics were dried over magnesium sulphate, filtered and evaporated to give 8-cyclopropylmethyl-1,4-dioxa-spiro[4.5]decane-8-carbaldehyde.

The crude aldehyde was dissolved in tetrahydrofuran (40 mL) and 2-methyl-2-propanesulfinamide (1.81 g, 14.9 mmol, 1.1 eq.) and titanium(IV) ethoxide (4.27 mL, 20.3 mmol, 1.5 eq.) were added. The resulting mixture was stirred for 5 h under reflux and 16 h at room temperature, before being treated with water (10 mL) and filtered through celite. The filter cake was washed with ethyl acetate, the aqueous layer was separated and extracted twice with ethyl acetate. The combined organic layers were dried over magnesium sulphate, filtered, and concentrated in vacuo. The crude product was purified by flash chromatography (SiO₂, 0%→100% ethyl acetate in heptane) to yield 1.90 g of the title compound (19). R$_t$=1.58 min (Method B). Detected mass: 328.3 (M+H⁺).

b) 2-Methyl-propane-2-sulfinic acid [1-(8-cyclopropylmethyl-1,4-dioxa-spiro[4.5]dec-8-yl)-2,2,2-trifluoro-ethyl]-amide (20)

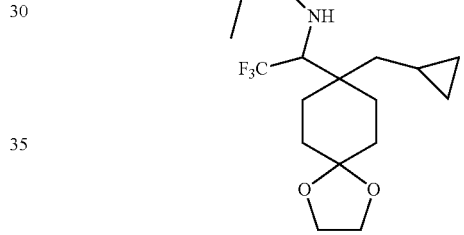

A solution of 2-methyl-propane-2-sulfinic acid 1-(8-cyclopropylmethyl-1,4-dioxa-spiro[4.5]dec-8-yl)-methylideneamide (19, 1.00 g, 3.05 mmol) in tetrahydrofuran was cooled to −40° C. and was treated sequentially with tetramethylammonium fluoride (313 mg, 3.36 mmol, 1.1 eq.) and (trifluoromethyl)trimethylsilane (587 µL, 3.97 mmol, 1.3 eq.). The mixture was stirred for 2 h at 0° C. before being quenched by addition of saturated aqueous ammonium chloride solution and extracted twice with ethyl acetate. The combined organic layers were dried over magnesium sulphate, filtered, and concentrated in vacuo to give 960 mg of the title compound. R$_t$=1.63 min (Method B). Detected mass: 398.3 (M+H⁺).

c) 4-(1-Amino-2,2,2-trifluoro-ethyl)-4-cyclopropylmethyl-cyclohexanol (21)

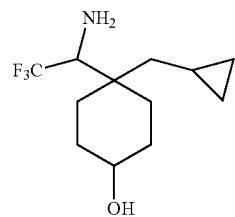 [SMILES: NC(C(F)(F)F)C1(CC2CC2)CCC(O)CC1]

A solution of 2-methyl-propane-2-sulfinic acid [1-(8-cyclopropylmethyl-1,4-dioxa-spiro[4.5]dec-8-yl)-2,2,2-trifluoro-ethyl]-amide (20, 1.00 g, 2.52 mmol) in 80% acetic acid (10 mL) was heated in a microwave oven for 10 min at 130° C. Then, the reaction mixture was slowly dropped into cold saturated sodium bicarbonate solution (150 mL), stirred for 30 min at room temperature and extracted three times with dichloromethane. The combined organic layers were dried over magnesium sulphate, filtered, and concentrated in vacuo to give the crude ketone, which was taken up in ethanol (20 mL), cooled to 0° C. and treated with sodium borohydride (190 mg, 5.03 mmol, 2.0 eq.). After the reaction went to completion, the mixture was poured onto water (20 mL) and extracted three times with dichloromethane. The organic layers were concentrated in vacuo and the residue was dissolved in a mixture of 2-propanol (15 mL) and 6N aqueous hydrochloric acid (5 mL). After stirring overnight at room temperature, another 5 mL of 6N aqueous hydrochloric acid were added and the mixture was warmed to 50° C. for 1 h. The reaction mixture was concentrated in vacuo and lyophilized twice from water to give the title compound (21) as racemic mixture of diastereoisomers as its hydrochloride. $R_t$=0.73 min, 0.82 min (Method B). Detected mass: 252.3 (M+H$^+$).

The following products were synthesized as hydrochlorides following the procedure described for Example 1 (Step d and e) starting from the respective aminoalcohols (prepared using the procedure described for the synthesis of 21) and 1-benzyloxy-7-chloro-6-fluoro-isoquinoline (1). The aminoalcohols for Example 46 and 47 were prepared starting from 2-(trimethylsilyl)thiazole using the procedure described for the synthesis of 21. The regioisomers formed in the alkylation step (analogously to the preparation of 20) have been separated via flash chromatography. Stereochemistry of the obtained products has not been assigned.

| Ex.-No. | Product | Isomer | Chemical Name | [M + H$^+$] | $R_t$/[min] | Method |
|---|---|---|---|---|---|---|
| 40 | | 1 | 6-[4-(1-Amino-2,2,2-trifluoro-ethyl)-4-cyclopropylmethyl-cyclohexyloxy]-7-chloro-2H-isoquinolin-1-one | 429.1 | 2.55 | A |
| 41 | | 2 | 6-[4-(1-Amino-2,2,2-trifluoro-ethyl)-4-cyclopropylmethyl-cyclohexyloxy]-7-chloro-2H-isoquinolin-1-one | 429.3 | 3.63 | D |
| 42 | | 1 | 6-[4-(1-Amino-2,2,2-trifluoro-ethyl)-4-isopropyl-cyclohexyl-oxy]-7-chloro-2H-isoquinolin-1-one | 417.1 | 2.49 | A |
| 43 | | 2 | 6-[4-(1-Amino-2,2,2-trifluoro-ethyl)-4-isopropyl-cyclohexyl-oxy]-7-chloro-2H-isoquinolin-1-one | 417.1 | 2.58 | A |
| 44 | | 1 | 6-[4-(1-Amino-2,2,3,3,3-pentafluoro-propyl)-4-isopropyl-cyclohexyloxy]-7-chloro-2H-isoquinolin-1-one | 467.1 | 3.24 | A |
| 45 | | 2 | 6-[4-(1-Amino-2,2,3,3,3-pentafluoro-propyl)-4-isopropyl-cyclohexyloxy]-7-chloro-2H-isoquinolin-1-one | 467.1 | 3.27 | A |

| Ex.-No. | Product | Isomer | Chemical Name | [M + H⁺] | R$_t$/ [min] | Method |
|---|---|---|---|---|---|---|
| 46 | | 1 + 2 | 6-[4-(Amino-thiazol-2-yl-methyl)-4-isopropyl-cyclohexyl-oxy]-7-chloro-2H-isoquinolin-1-one | 432.1 | 1.05, 1.13 | F |
| 47 | | 1 | 6-[4-(Amino-thiazol-5-yl-methyl)-4-isopropyl-cyclohexyl-oxy]-7-chloro-2H-isoquinolin-1-one | 432.3 | 0.64 | F |
| 48 | | 2 | 6-[4-(Amino-thiazol-5-yl-methyl)-4-isopropyl-cyclohexyl-oxy]-7-chloro-2H-isoquinolin-1-one | 432.3 | 0.67 | F |

Example 89

6-[4-(1-Amino-2-methyl-propyl)-4-isopropyl-cyclohexyloxy]-7-chloro-2H-isoquinolin-1-one

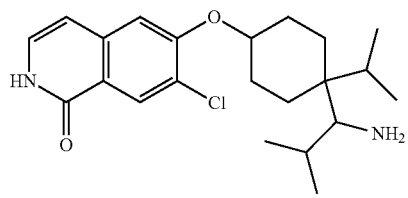 [SMILES: CC(C)C(N)C1(C(C)C)CCC(Oc2cc3cc[nH]c(=O)c3cc2Cl)CC1]

11 mg of Example 89 were synthesized as hydrochloride following the procedure described for Example 1 (Step d and e) starting from 137 mg (642 µmol) of the respective aminoalcohol (prepared from 2-methyl-propane-2-sulfinic acid 1-(8-isopropyl-1,4-dioxa-spiro[4.5]dec-8-yl)-methylideneamide using a protocol similar to the preparation of 21 but using isopropyllithium as nucleophile) and 168 mg (584 µmol) of 1-benzyloxy-7-chloro-6-fluoro-isoquinoline (1). R$_t$=1.84 min (Method J). Detected mass: 3912 ([M+H⁺]).

Example 90 cis-6-[4-(1-Amino-propyl)-4-isopropyl-cyclohexyloxy]-7-chloro-4-fluoro-2H-isoquinolin-1-one a) cis-{1-[4-(7-Chloro-1-oxo-1,2-dihydro-isoquinolin-6-yloxy)-1-isopropyl-cyclohexyl]-propyl}-carbamic acid tert-butyl ester (49)

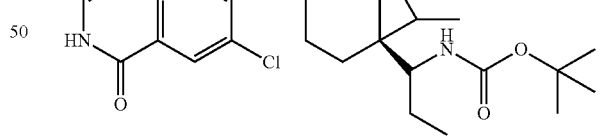

To a solution of 1.71 g (4.14 mmol) of Example 8 in 200 mL of absolute dichloromethane were added triethylamine (0.86 mL, 6.21 mmol) and di-tert.-butyl dicarbonate (1.35 g, 6.21 mmol). After stirring overnight, the reaction was diluted with 100 mL of dichloromethane and washed with 1N aqueous sodium hydroxide solution, twice with 1N aqueous hydrochloric acid, twice with water and once with brine. The organic phase was dried over magnesium sulphate, filtered and evaporated to give crude product which was purified by silica gel chromatography (dichloromethane:methanol) to give 1.00 g of the desired product. R$_t$=0.89 min (Method Q). Detected mass: 421.2 ([M-tert-butyl]+H⁺).

b) cis-6-[4-(1-Amino-propyl)-4-isopropyl-cyclo-hexyloxy]-7-chloro-4-fluoro-2H-isoquinolin-1-one (Example 90)

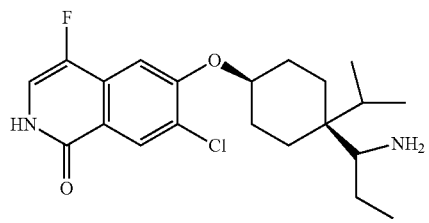 [SMILES: CCC(N)[C@]1(C(C)C)CC[C@H](Oc2cc3c(F)c[nH]c(=O)c3cc2Cl)CC1]

250 mg of 49 were dissolved in 3.6 mL of a mixture of acetonitrile and methanol (1:1). 204 mg of N-Fluoro-N'-chloromethyl-triethylenediamine-bis(tetrafluoroborate) was added and the mixture was allowed to stir for five days. The mixture was diluted with dichloromethane, extracted several times with water, then 2N hydrochloric acid and brine. The organic layer was evaporated to dryness, the residue was dissolved in 10 mL of a mixture of isopropanol and 1 N hydrochloric acid and heated for 45 minutes in a microwave oven at 110° C.

The mixture was diluted with water, extracted twice with methyl tert-butyl ether and lyophilized. The crude material was taken up in water and lyophilized twice to give 177 mg of the desired product as the hydrochloride. $R_t$=2.59 min (Method C). Detected mass: 395.2 (M+H$^+$).

Example 91 cis-6-[4-(1-Amino-propyl)-4-ethyl-cyclohexyloxy]-7-chloro-4-fluoro-2H-isoquinolin-1-one a) cis-{1-[4-(7-Chloro-1-oxo-1,2-dihydro-isoquinolin-6-yloxy)-1-isopropyl-cyclohexyl]propyl}-carbamic acid tert-butyl ester (50)

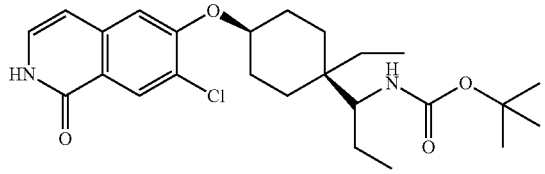 [SMILES: CCC(NC(=O)OC(C)(C)C)[C@]1(CC)CC[C@H](Oc2cc3cc[nH]c(=O)c3cc2Cl)CC1]

To a solution of 1.8 g of Example 34 in 20 mL of absolute dichloromethane were added triethylamine (0.75 mL) and di-tert.-butyl dicarbonate (1.18 g). After stirring overnight, the reaction was diluted with 100 mL of dichloromethane and washed twice with 1N aqueous sodium hydroxide solution, 1N aqueous hydrochloric acid, and water and once with brine. The organic phase was dried over magnesium sulphate, filtered and evaporated to give 2.05 g of the desired product. $R_t$=1.86 min (Method G). Detected mass: 407.2 ([M-tert-butyl]+H$^+$).

b) cis-6-[4-(1-Amino-propyl)-4-ethyl-cyclohexyloxy]-7-chloro-4-fluoro-2H-isoquinolin-1-one (Example 91)

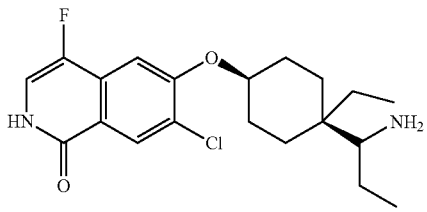 [SMILES: CCC(N)[C@]1(CC)CC[C@H](Oc2cc3c(F)c[nH]c(=O)c3cc2Cl)CC1]

200 mg of 50 were dissolved in 3 mL of a mixture of acetonitrile and methanol (1:1). 168 mg of N-Fluoro-N'-chloromethyl-triethylenediamine-bis(tetrafluoroborate) were added and the mixture was allowed to stir for six days. The mixture was diluted with dichloromethane, extracted several times with water, then 2N hydrochloric acid and brine. The organic layer was evaporated to dryness, the residue was dissolved in 10 mL of a mixture of isopropanol and 1 N hydrochloric acid and heated for 30 minutes in a microwave oven at 100° C.

The mixture was diluted with water, extracted twice with methyl tert-butyl ether and lyophilized. The crude material was taken up in water and lyophilized twice to give 106 mg of the desired product as the hydrochloride. $R_t$=1.31 min (Method G). Detected mass: 381.2 (M+H$^+$).

Example 92 cis-6-[4-(1-Amino-propyl)-4-ethyl-cyclohexyloxy]-4-bromo-7-chloro-2H-isoquinolin-1-one a) cis-{1-[4-(4-Bromo-7-chloro-1-oxo-1,2-dihydro-isoquinolin-6-yloxy)-1-ethyl-cyclohexyl]-propyl}-carbamic acid tert-butyl ester (51)

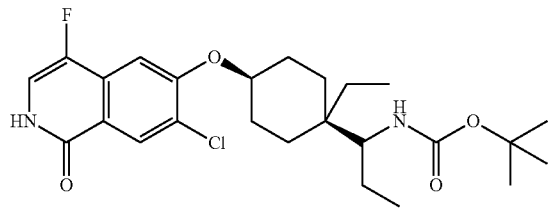 [SMILES: CCC(NC(=O)OC(C)(C)C)[C@]1(CC)CC[C@H](Oc2cc3c(F)c[nH]c(=O)c3cc2Cl)CC1]

1.5 g of 50 were dissolved in 25 mL of chloroform and 3.8 mL of a 1M solution of bromine in chloroform were added dropwise at 0° C. The mixture was allowed to warm to room temperature. When conversion was complete, the mixture was quenched by addition of 20% sodium dithiosulfite solution, extracted with 1N HCl and brine, dried over magnesium sulphate and evaporated to dryness. The crude product was purified by silica gel chromatography to give the desired product. $R_t$=2.02 min (Method G). Detected mass: 485.1/487.1 ([M-tert-butyl]+H$^+$).

b) cis-6-[4-(1-amino-propyl)-4-ethyl-cyclohexyloxy]-4-bromo-7-chloro-2H-isoquinolin-1-one (Example 92)

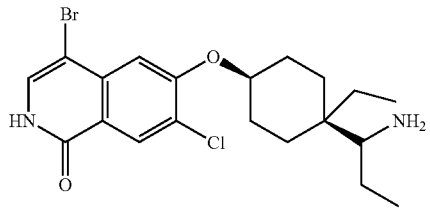 [SMILES: CCC(N)[C@]1(CC)CC[C@H](Oc2cc3c(Br)c[nH]c(=O)c3cc2Cl)CC1]

70 mg of 51 were dissolved in 6 mL of a mixture of isopropanol and 1 N hydrochloric acid and heated for 33 minutes in a microwave oven at 120° C.

The mixture was diluted with water and lyophilized. The crude material was taken up in water and lyophilized twice to give 177 mg of the desired product as the hydrochloride. $R_t$=1.36 min (Method G). Detected mass: 441.2/443.1 (M+H⁺).

Example 93 cis-6-[4-(1-Amino-propyl)-4-ethyl-cyclohexyloxy]-7-chloro-1-oxo-1,2-dihydro-isoquinoline-4-carbonitrile

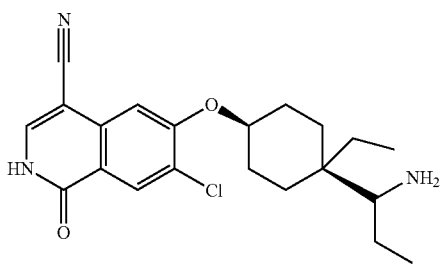 [SMILES: CCC(N)[C@]1(CC)CC[C@H](Oc2cc3c(C#N)c[nH]c(=O)c3cc2Cl)CC1]

150 mg of 51 were dissolved in 9 mL of degassed dimethyl formamide and 43 mg of zinc cyanide and 32 mg of tetrakis(triphenylphosphine)palladium(0) were added under argon. The mixture was heated in a microwave oven for 90 minutes at 150° C. The mixture was filtered, the solvent was evaporated and the crude product was purified by HPLC. The purified product was taken up in 2 mL of isopropanol and 2 mL of 1N hydrochloric acid and heated in a microwave oven at 100° C. for 1 hour. Water was added, the solution was extracted twice with methyl tert.butyl ether and the aqueous layer was lyophilized. The residue was taken up in water and lyophilized again to give 115.7 mg of the desired product as its hydrochloride. $R_t$=2.55 min (Method F). Detected mass: 388.2 (M+H⁺).

Example 94 cis-6-[4-(1-Amino-propyl)-4-isopropyl-cyclohexyloxy]-4-bromo-7-chloro-2H-isoquinolin-1-one

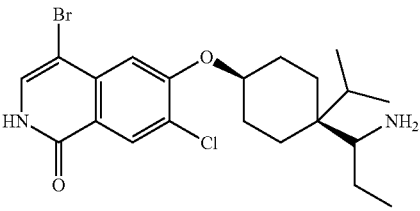 [SMILES: CCC(N)[C@]1(C(C)C)CC[C@H](Oc2cc3c(Br)c[nH]c(=O)c3cc2Cl)CC1]

Following the procedure described for the synthesis of Example 92, cis-6-[4-(1-amino-propyl)-4-isopropyl-cyclohexyloxy]-4-bromo-7-chloro-2H-isoquinolin-1-one was synthesized starting from cis-{1-[4-(7-chloro-1-oxo-1,2-dihydro-isoquinolin-6-yloxy)-1-isopropyl-cyclohexyl]-propyl}-carbamic acid tert-butyl ester (49) and bromine. $R_t$=1.14 min (Method O). Detected mass: 455.1/457.2 (M+H⁺).

Examples 95 and 96 cis-6-[4-(1-amino-2-fluoro-ethyl)-4-ethyl-cyclohexyloxy]-7-chloro-2H-isoquinolin-1-one (Example 95) and trans-6-[4-(1-amino-2-fluoro-ethyl)-4-ethyl-cyclohexyloxy]-7-chloro-2H-isoquinolin-1-one (Example 96)

a) 2-Methyl-propane-2-sulfinic acid [2-benzenesulfonyl-1-(8-ethyl-1,4-dioxa-spiro[4.5]dec-8-yl)-2-fluoro-ethyl]-amide (52)

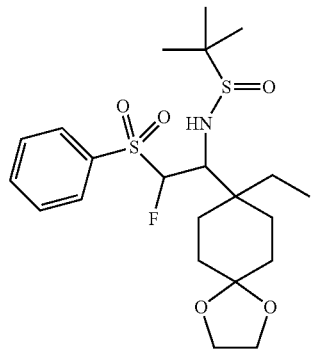 [SMILES: CCC1(C(NS(=O)C(C)(C)C)C(F)S(=O)(=O)c2ccccc2)CCC2(CC1)OCCO2]

To a solution of 1.70 g (5.64 mmol) of 2-methyl-propane-2-sulfinic acid 1-(8-ethyl-1,4-dioxa-spiro[4.5]dec-8-yl)methylideneamide (prepared from 8-ethyl-1,4-dioxa-spiro[4.5]decane-8-carbonitrile using the protocol described for the synthesis of 19) and 982 mg (5.64 mmol) of fluoromethylphenyl sulfone in 60 mL of abs. tetrahydrofuran were added at −78° C. 5.92 mL (5.92 mmol) of a 1M solution of lithium-bis(trimethylsilyl)amide in tetrahydrofuran. The mixture was stirred for 1 h at −78° C. before being quenched by addition of saturated aqueous ammonium chloride solution and extracted twice with 100 mL of ethyl acetate. The combined organic layers were dried over magnesium sulphate, filtered, and concentrated in vacuo to give 2.65 g of the crude title compound. $R_t$=0.91 min (Method P). Detected mass: 476.4 (M+H$^+$)

b) 2-Methyl-propane-2-sulfinic acid [1-(8-ethyl-1,4-dioxa-spiro[4.5]dec-8-yl)-2-fluoro-ethyl]-amide (53) and 2-Methyl-propane-2-sulfinic acid [2-benzene-sulfonyl-1-(8-ethyl-1,4-dioxa-spiro[4.5]dec-8-yl)-ethyl]-amide (54)

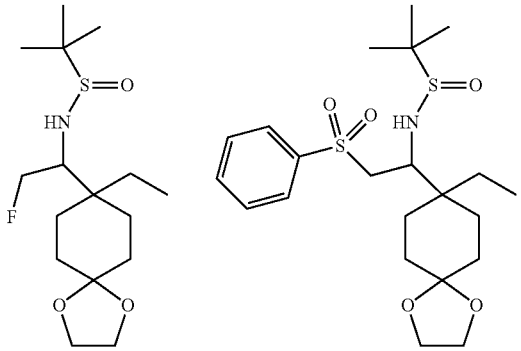

1.0 g (2.10 mmol) of 2-Methyl-propane-2-sulfinic acid [2-benzenesulfonyl-1-(8-ethyl-1,4-dioxa-spiro[4.5]dec-8-yl)-2-fluoro-ethyl]-amide (52) was dissolved in 30 mL of dry methanol and 895 mg (6.31 mmol) of dibasic sodium phosphate were added. The suspension was cooled to −20° C., and treated with 1.41 g of sodium mercury amalgam (5% mercury). The reaction mixture was stirred at 0° C. for 16 h and another 470 mg sodium almalgam were added. After stirring for 7 h at room temperature, the solution was decanted from the solids, evaporated to dryness and the residue partitioned between 50 mL of brine and 100 mL of diethylether. The organic layer was dried over sodium sulphate, filtered and concentrated in vacuo. Purification by flash chromatography (SiO$_2$, 0%→100% ethyl acetate in heptane) yielded 296 mg of 53 [$R_t$ 0.81 min (Method P). Detected mass: 336.4 (M+H$^+$)] and 96 mg of 54 [$R_t$=0.82 min (Method P). Detected mass: 458.3 (M+H$^+$)].

c) 4-(1-Amino-2-fluoro-ethyl)-4-ethyl-cyclohexanol (55)

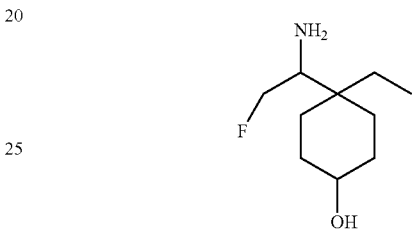

99 mg of 55 were synthesized as mixture of stereoisomers as its hydrochloride from 236 mg (704 µmol) of 53 using the protocol described for the synthesis of compound 21. $R_t$=0.09, 0.14 min (Method P). Detected mass: 190.3 ([M+H$^+$).

The following products were synthesized as their respective hydrochlorides in a similar fashion as described for the alternative synthesis of Example 1 (Step d and e) starting from the respective aminoalcohols, prepared as described above and 7-chloro-6-fluoro-1-methoxy-isoquinoline (4).

| Ex.-No. | Product | Chemical Name | [M + H$^+$] | $R_t$/[min] | Method |
|---|---|---|---|---|---|
| 95 | | cis-6-[4-(1-Amino-2-fluoro-ethyl)-4-ethyl-cyclohexyloxy]-7-chloro-2H-isoquinolin-1-one | 367.1 | 1.64 | N |
| 96 | | trans-6-[4-(1-Amino-2-fluoro-ethyl)-4-ethyl-cyclohexyloxy]-7-chloro-2H-isoquinolin-1-one | 367.1 | 1.66 | N |

Example 98

6-[4-(1-amino-3-methoxy-propyl)-4-ethyl-cyclohexyloxy]-7-chloro-2H-isoquinolin-1-one a) 2-Methyl-propane-2-sulfinic acid [1-(8-ethyl-1,4-dioxa-spiro[4.5]dec-8-yl)-allyl]-amide (57)

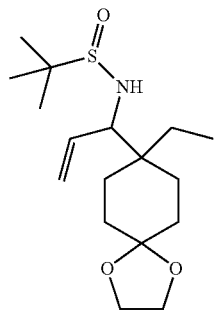 [SMILES: C=CC(NS(=O)C(C)(C)C)C1(CC)CCC2(CC1)OCCO2]

Under argon, 2.00 g (6.64 mmol) of 2-methyl-propane-2-sulfinic acid 1-(8-ethyl-1,4-dioxa-spiro[4.5]dec-8-yl)-methylideneamide (prepared from 8-ethyl-1,4-dioxa-spiro[4.5]decane-8-carbonitrile using the protocol described for the synthesis of 19) were dissolved in 5 mL of absolute tetrahydrofuran. Then, 7.30 mL (7.30 mmol) of vinylmagnesium bromide (1M in tetrahydrofuran) were added dropwise at 0° C. and the reaction mixture was stirred for 17 h at room temperature. Another 16.6 mL (16.6 mmol) of vinylmagnesium bromide (1M in tetrahydrofuran) were added and the mixture stirred for 2 h at room temperature. The reaction mixture was cooled to 0° C. and 15 mL of saturated aqueous sodium sulphate solution were added. The suspension was filtered over celite, the organic layer was dried over magnesium sulphate, filtered, and concentrated in vacuo. The crude product was purified by flash chromatography (SiO$_2$, 0%→100% ethyl acetate in heptane) to yield 1.30 g of the title compound 57 as mixture of diastereoisomers. R$_t$=2.19, 2.26 min (Method N). Detected mass: 330.2 (M+H$^+$).

b) 2-Methyl-propane-2-sulfinic acid [1-(8-ethyl-1,4-dioxa-spiro[4.5]dec-8-yl)-3-methoxy-propyl]-amide (58)

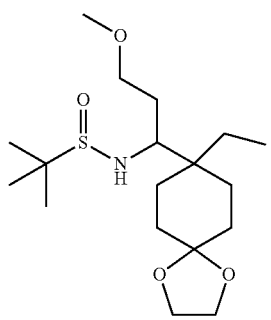 [SMILES: CCC1(C(CCOC)NS(=O)C(C)(C)C)CCC2(CC1)OCCO2]

10.9 mL (5.46 mmol) of a 0.5M solution of 9-BBN in tetrahydrofuran were added to a solution of 600 mg (1.82 mmol) of 2-methyl-propane-2-sulfinic acid [1-(8-ethyl-1,4-dioxa-spiro[4.5]dec-8-yl)-allyl]-amide (57) in 5 mL THF at 0° C. The reaction mixture was allowed to warm to room temperature over night, before being cooled to 0° C. Then, 13.5 mL of 3M aqueous sodium hydroxide and 13.5 mL of 30% aqueous hydrogen peroxide were added slowly, and the mixture was stirred for 16 h at room temperature. The mixture was extracted twice with 50 mL of ethyl acetate, washed with water (30 mL) and saturated sodium chloride solution (30 mL), dried over magnesium sulphate and concentrated in vacuo.

The crude alcohol was dissolved in 9 mL of tetrahydrofuran and added slowly to a suspension of 145 mg (3.63 mmol) of sodium hydride (60%) in 9 mL tetrahydrofuran at 0° C. The suspension was stirred for 30 min, then 339 µL (5.45 mmol) of iodomethane were added. The reaction mixture was stirred at room temperature over a period of 20 h and twice additional 339 µL (5.45 mmol) of iodomethane were added.

Then, 30 mL of methanol and 15 mL of aqueous ammonium hydroxide solution (33%) were added. The reaction mixture was evaporated to dryness to give 655 mg of the title compound 58 in a purity sufficient for further conversion. R$_t$=0.85 min (Method P). Detected mass: 362.3 (M+H$^+$).

c) 4-(1-Amino-3-methoxy-propyl)-4-ethyl-cyclohexanol (59)

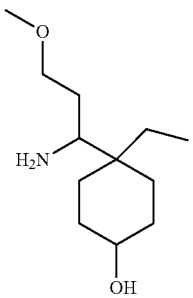

60 mg of 4-(1-Amino-3-methoxy-propyl)-4-ethyl-cyclohexanol (59) as mixture of diastereomers were prepared as hydrochloride using a procedure similar to the one described for the synthesis of 21, starting with 315 mg of 2-methyl-propane-2-sulfinic acid [1-(8-ethyl-1,4-dioxa-spiro[4.5]dec-8-yl)-3-methoxy-propyl]-amide (58). R$_t$=0.20, 0.39 min (Method P). Detected mass: 216.2 (M+H$^+$).

d) 6-[4-(1-amino-3-methoxy-propyl)-4-ethyl-cyclohexyloxy]-7-chloro-2H-isoquinolin-1-one (Example 98)

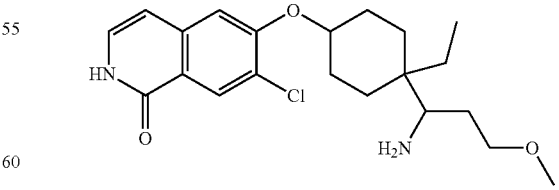

Example 98 was synthesized using the reaction sequence as described for the alternative synthesis of Example 1 (step d and e). 60 mg of 4-(1-Amino-3-methoxy-propyl)-4-ethyl-cyclohexanol (59) and 53.9 mg of 7-chloro-6-fluoro-1-methoxy-isoquinoline (4) were used to give 43 mg of Example 98 as hydrochloride. Stereochemistry was not assigned. $R_t$=1.78 min (Method N). Detected mass: 393.3 (M+H$^+$).

Example 99 cis-6-[4-(1-amino-propyl)-4-(1,1-dioxo-tetrahydrothiopyran-4-yl)-cyclohexyloxy]-7-chloro-2H-isoquinolin-1-one a) cis-{1-[4-(7-Chloro-1-methoxy-isoquinolin-6-yloxy)-1-(tetrahydro-thiopyran-4-yl)-cyclohexyl]-propyl}-carbamic acid tert-butyl ester (60)

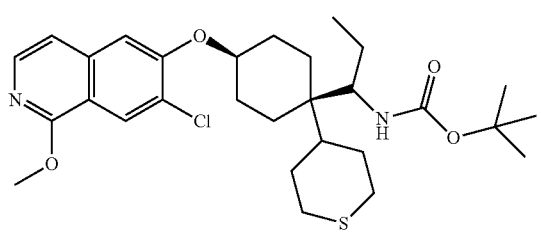 [SMILES: CCC(NC(=O)OC(C)(C)C)[C@]1(C2CCSCC2)CC[C@H](Oc2cc3ccnc(OC)c3cc2Cl)CC1]

To a solution of 61 mg (136 μmol) of cis-1-[4-(7-chloro-1-methoxy-isoquinolin-6-yloxy)-1-(tetrahydro-thiopyran-4-yl)-cyclohexyl]-propylamine [prepared from cis-4-(1-amino-propyl)-4-(tetrahydro-thiopyran-4-yl)-cyclohexanol and 7-chloro-6-fluoro-1-methoxy-isoquinoline (4) in a similar fashion as described for the alternative synthesis of Example 1] in 2 mL of dichloromethane were added 28.2 μL (20.6 mg, 204 μmol) of triethylamine and 44.4 mg (204 μmol) of di-tert-butyl-dicarbonate, and the mixture was stirred overnight at room temperature. The reaction mixture was evaporated, taken up in diethylether, filtered over celite and the filtrate was concentrated in vacuo to give 76 mg of the title compound in a purity sufficient for further conversion. $R_t$=1.06 min (Method Q). Detected mass: 549.2 (M+H$^+$).

b) cis-6-[4-(1-amino-propyl)-4-(1,1-dioxo-tetrahydrothiopyran-4-yl)-cyclohexyloxy]-7-chloro-2H-isoquinolin-1-one (Example 99)

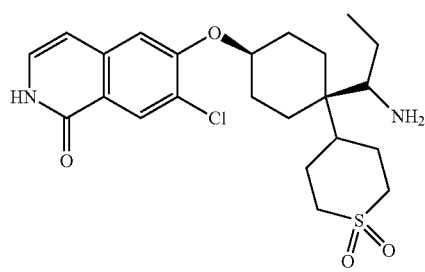 [SMILES: CCC(N)[C@]1(C2CCS(=O)(=O)CC2)CC[C@H](Oc2cc3cc[nH]c(=O)c3cc2Cl)CC1]

A solution of 76 mg (138 μmol) of cis-{1-[4-(7-chloro-1-methoxy-isoquinolin-6-yloxy)-1-(tetrahydro-thiopyran-4-yl)-cyclohexyl]-propyl}-carbamic acid tert-butyl ester (60) in 3 mL of absolute dichloromethane was treated at 0° C. with a solution of 102 mg (415 μmol) of m-chloroperbenzoic acid in 1 mL of dichloromethane, and the reaction mixture was stirred at room temperature for 2 h. Then, 25 mL of water were added and the mixture was extracted three times with dichloromethane. The combined organic layers were washed with a 0.1M aqueous solution of sodium thiosulphate, saturated aqueous sodium bicarbonate solution and brine, dried over magnesium sulphate, filtered and evaporated. After purification by flash chromatography (SiO$_2$, 0%→30% methanol in dichloromethane) to yield 36 mg of {1-[cis-4-(7-chloro-1-methoxy-isoquinolin-6-yloxy)-1-(1,1-dioxo-tetrahydro-thiopyran-4-yl)-cyclohexyl]-propyl}-carbamic acid tert-butyl ester, the product was dissolved in 2 mL of a 1:1 mixture of 2-propanol and 1N aqueous hydrochloric acid and heated in the microwave for 30 min at 100° C. The reaction mixture was evaporated and lyophilized from water twice to give 21 mg of the title compound (Example 99) as its hydrochloride. $R_t$=1.17 min (Method G). Detected mass: 467.2 (M+H$^+$).

Example 100 cis-6-[4-(1-Amino-ethyl)-4-propyl-cyclohexyloxy]-7-chloro-isoquinolin-1-ylamine a) tert-Butyl-(7-chloro-6-fluoro-isoquinolin-1-yl)-amine (61)

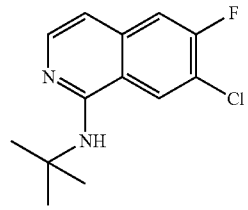 [SMILES: CC(C)(C)Nc1nccc2cc(F)c(Cl)cc12]

A solution of 5.0 g (25.3 mmol) of 7-chloro-6-fluoro-isoquinoline 2-oxide (9) in 120 mL of benzotrifluoride was treated with 15.9 mL (11.1 g, 152 mmol) of tert-butylamine and cooled to 0° C. Then, 17.3 g (53.1 mmol) of p-toluenesulfonic anhydride were slowly added portionwise with temperature control (<10° C.). The reaction mixture was stirred at room temperature for 16 h, before being cooled to 0° C. and another 8.0 mL (76.1 mmol) of tert-butylamine and 8.26 g (25.3 mmol) of p-toluenesulfonic anhydride were added. The reaction mixture was stirred for 24 h at room temperature, then concentrated and partitioned between 120 mL of water and 150 mL of dichloromethane. The phases were separated and the organic phase was washed eight times with 3N aqueous sodium hydroxide, dried over magnesium sulphate, filtered and evaporated to dryness. The crude product was purified twice by silica gel chromatography (dichloromethane: methanol) to give 277 mg of pure desired product (61) and 714 mg of the product slightly contaminated with p-toluenesulfonic acid. $R_t$=2.35 min (Method C). Detected mass: 253.1 (M+H$^+$).

b) cis-6-[4-(1-Amino-ethyl)-4-propyl-cyclohexyloxy]-7-chloro-isoquinolin-1-ylamine (Example 100)

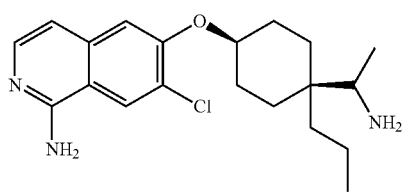 [SMILES: CCC[C@]1(C(C)N)CC[C@@H](Oc2cc3ccnc(N)c3cc2Cl)CC1]

28 mg of Example 100 were obtained following a reaction sequence similar to the one used for the synthesis of Example 1 (step d and e), starting from 73.4 mg (396 μmol) of 4-(1-amino-ethyl)-4-propyl-cyclohexanol and 100 mg (0.40 mmol) of tert-butyl-(7-chloro-6-fluoro-isoquinolin-1-yl)-amine (61). $R_t$=2.26 min (Method C). Detected mass: 362.3 (M+H$^+$).

Example 101 and 102

6-[3-(1-Amino-propyl)-3-propyl-cyclopentoxy]-7-chloro-2H-isoquinolin-1-one a) 1-cyano-1-propylcyclopent-3-ene (62)

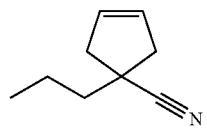

LDA (276 mL, 553 mmol 2M in THF) was added dropwise at −78° C. under argon to a stirred solution of valeronitrile (20 g, 25.3 mL, 241 mmol) in THF (250 mL) and then stirred for 15 minutes. The reaction mixture was then warmed to room temperature and stirred for a further 20 minutes. After cooling to −78° C., cis-1,4-dichlorobutene (30.1 g, 25.3 mL) was added dropwise over 10 minutes and the mixture stirred for 10 minutes. The mixture was allowed to warm to room temperature and was then stirred overnight. The reaction was quenched by gentle addition to 150 mL ice cold water and followed by extraction with methyl tea butyl ether. Evaporation gave 47.5 g of an orange oil. Vacuum distillation 0.2-16 mbar, 55-105° C. gave 2.3 g of a yellow oil which was used without further purification.

b) 1-(1-aminopropyl)-1-propylcyclopent-3-ene (63)

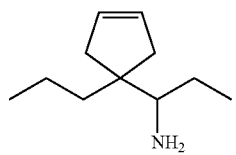

1-cyano-1-propylcyclopent-3-ene (62, 2.3 g, 16.9 mmol) was dissolved in toluene (15 mL) and ethyl magnesium bromide (11.2 mL, 33.7 mmol, 3M in ether) added. After stirring for 30 minutes at 90° C., the reaction mixture was cooled and added dropwise to ice cold methanol (66 mL), followed by sodium borohydride (638 mg, 17 mmol). The mixture was warmed to room temperature and stirred overnight. The white suspension was treated with sodium hydroxide solution (aqueous, 1M), filtered through celite and then extracted with dichloromethane/isopropanol (3:1). The filtrate was washed with dichloromethane. The organic phase was washed with brine, dried over sodium sulphate and evaporated to give 3.8 g of a yellow oil. This was taken up in dichloromethane and extracted twice with hydrochloric acid (2M). The aqueous layer was made basic with sodium hydroxide solution (6M) and extracted with dichloromethane. Evaporation gave 1.38 g of desired product as a yellow oil which was used without further purification.

c) 1-(1-aminopropyl)-1-propylcyclopentan-3-ol (64)

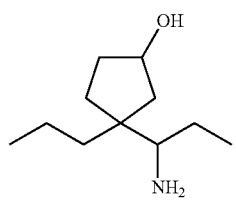

1-(1-aminopropyl)-1-propylcyclopent-3-ene (63, 1.4 g, 8.25 mmol) was dissolved in THF (15 mL) at 0° C. under argon. Borane (9.1 mL, 9.07 mmol, 1M in THF) was added dropwise over 10 minutes. The reaction mixture was allowed to warm to room temperature before stirring overnight. After cooling to 0° C., water was added (4 mL), followed by hydrogen peroxide (5.8 mL, 30% solution in water) and sodium hydroxide solution (9.1 mL, 1M aqueous solution). After stirring for 5 minutes the mixture was extracted with ethyl acetate, dried over sodium sulphate and evaporated to give 1.54 g of desired product as a mixture of isomers. $R_t$=0.81, 0.84, 0.88 min (Method M). Detected mass: 186.2 (M+H$^+$).

d) 1-[3-(7-chloro-1-methoxyisoquinolin-6-yloxy)-cyclopentyl]-1-propyl-propylamines (65 and 66)

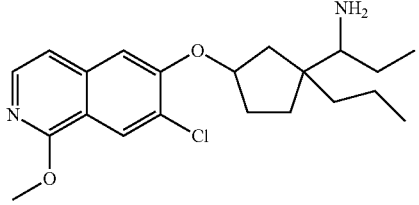 [SMILES: CCCC1(C(N)CC)CCC(Oc2cc3ccnc(OC)c3cc2Cl)C1]

1-[3-(7-chloro-1-methoxyisoquinolin-6-yloxy)-cyclopentyl]-1-propyl-propylamines (65 and 66) were prepared as a mixture of isomers from 1-(1-aminopropyl)-1-propylcyclopentan-3-ol (64) and 7-chloro-6-fluoro-1-methoxyisoquinoline (4) as described for the alternative synthesis of Example 1, step d. $R_t$=1.51 min (Method G). Detected mass: 3772 (M+H$^+$) and $R_t$=1.56 min (Method G). Detected mass: 377.2 (M+H$^+$).

e) 6-[3-(1-Amino-propyl)-3-propyl-cyclopentoxy]-7-chloro-2H-isoquinolin-1-one (Examples 101 and 102)

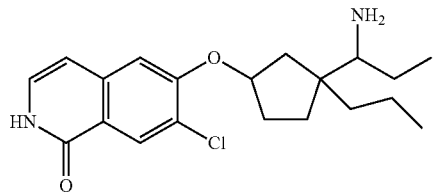 [SMILES: CCCC1(C(N)CC)CCC(Oc2cc3cc[nH]c(=O)c3cc2Cl)C1]

6-[3-(1-Amino-propyl)-3-propyl-cyclopentoxy]-7-chloro-2H-isoquinolin-1-ones Example 101 and Example 102 were prepared from 1-[3-(7-chloro-1-methoxyisoquinolin-6-yloxy)-cyclopentyl]-1-propyl-propylamines 65 and 66 as described for described for the alternative synthesis of Example 1, step e. $R_t$=1.33 min (Method G). Detected mass: 363.2 (M+H$^+$) and $R_t$=0.94 min (Method M). Detected mass: 363.3 (M+H$^+$).

Both examples were obtained as a mixture of isomers, relative stereochemistry was not assigned.

Example 103

6-[4-(1-Amino-propyl)-4-trifluoromethyl-cyclohexyloxy]-7-chloro-2H-isoquinolin-1-one (Isomer 1)

a) N-Methoxy-N-methyl-2-trifluoromethyl-acrylamide (67)

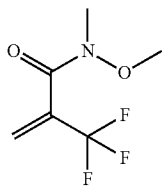

16.6 g (167 mmol) of N,O-dimethylhydroxylamine hydrochloride were suspended in 900 ml of CH$_2$Cl$_2$ and 29.1 ml (167 mmol) of N,N-diisopropylethylamine added dropwise at 0° C. The resulting solution was added dropwise to a solution of 20.0 g (143 mmol) of 2-(trifluoromethyl)propenoic acid in 500 ml of CH$_2$Cl$_2$ at −40° C. Afterwards, 34.5 g (167 mmol) of N,N'-dicyclohexylcarbodiimide were added and the mixture stirred at 0° C. for 16 h. The resulting suspension was then filtrated and the filtrate carefully evaporated (the desired product is volatile!). Afterwards, 100 ml of n-pentane were added and the suspension stirred for 30 minutes at ambient temperature. The precipitate was removed by filtration, the filtrate was carefully evaporated. Chromatography on silica gel using ethyl acetate/n-pentane 1:4 yielded 22.8 g of the desired product. $R_t$=0.56 min (Method P).

b) 4-Oxo-1-trifluoromethyl-cyclohexanecarboxylic acid methoxy-methyl-amide (68)

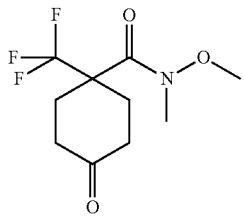

21.8 g (119 mmol) of N-Methoxy-N-methyl-2-trifluoromethyl-acrylamide (67) and 36.1 ml (29.6 mmol) of 2-(trimethylsiloxy)-1,3-butadiene were mixed and divided into 3 portions. Each portion was treated at 120° C. under microwave irradiation for 2 h. The combined reaction products were then diluted using 150 ml of THF, 100 ml of a 5% aqueous solution of HCl was added and stirred for 1 h at ambient temperature. Afterwards, the mixture was extracted three times using 200 ml of ethyl acetate each, dried using MgSO$_4$ and evaporated to yield 18.0 g, used without further purification. $R_t$=0.72 min (Method P).

c) 4-Hydroxy-1-trifluoromethyl-cyclohexanecarboxylic acid methoxy-methyl-amide (69)

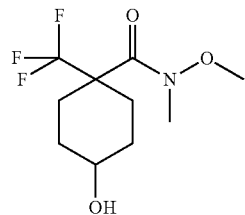 [SMILES: CON(C)C(=O)C1(C(F)(F)F)CCC(O)CC1]

18.0 g (71.1 mmol) of 4-Oxo-1-trifluoromethyl-cyclohexanecarboxylic acid methoxy-methyl-amide (68) were dissolved in 350 ml of anhydrous ethanol and 2.96 g (78.2 mmol) of NaBH$_4$ were added portionwise at −70° C. The mixture was then stirred for 1 h at ambient temperature, followed by addition of 500 ml of water. Initially, the pH was then adjusted to pH=4-5 using a 10% aqueous HCl-solution to remove remaining NaBH$_4$. Afterwards, the pH was adjusted to pH=8 using saturated aqueous NaHCO$_3$-solution and the ethanol was evaporated. The residual solution was extracted three times using 300 ml of ethyl acetate each. Afterwards, the organic layer was washed using 300 ml of a saturated aqueous NaCl-solution, dried over MgSO$_4$ and evaporated. Chromatography on silica gel using ethyl acetate/n-heptane yielded 6.00 g of 69 as a colourless oil, containing only one cis/trans isomer of unknown configuration. $R_t$=0.66 min (Method P).

d) 4-(tert-Butyl-dimethyl-silanyloxy)-1-trifluoromethyl-cyclohexanecarboxylic acid methoxy-methyl-amide (70)

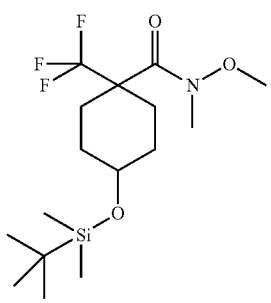 [SMILES: CON(C)C(=O)C1(C(F)(F)F)CCC(O[Si](C)(C)C(C)(C)C)CC1]

6.00 g (23.5 mmol) of 4-Hydroxy-1-trifluoromethyl-cyclohexanecarboxylic acid methoxy-methyl-amide (69) were dissolved in 20 ml of CH$_2$Cl$_2$ and 6.8 ml of 2,6-lutidine were added. Afterwards, 6.48 ml (28.2 mmol) of tert-butyldimethylsilyl trifluoromethanesulfonate were added at 0° C. and the mixture allowed to stand at ambient temperature for 16 h. The mixture was then diluted using 30 ml of CH$_2$Cl$_2$ and washed successively twice using 30 ml of water, twice using 30 ml of a 0.1; N aqueous HCl-solution and once using 30 ml of a saturated aqueous NaHCO$_3$-solution respectively. The organic layer was then dried over MgSO$_4$ and evaporated to yield 8.40 g. $R_t$=0.99 min (Method Q).

e) 4-(tert-Butyl-dimethyl-silanyloxy)-1-trifluoromethyl-cyclohexanecarbaldehyde (71)

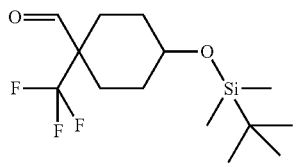 [SMILES: CC(C)(C)[Si](C)(C)OC1CCC(C=O)(C(F)(F)F)CC1]

4.15 g (11.2 mmol) of 4-(tert-Butyl-dimethyl-silanyloxy)-1-trifluoromethyl-cyclohexanecarboxylic acid methoxy-methyl-amide (70) were dissolved in 40 ml of anhydrous THF. Afterwards, 28.1 ml (28.1 mmol) of a 1M solution of diisobutylaluminium hydride in $CH_2Cl_2$ was added at 0° C. and the mixture was stirred at 0° C. for 30 minutes. 40 ml of a 10% aqueous solution of potassium sodium tartrate tetrahydrate were added and the mixture was stirred for 1 h at ambient temperature. The reaction mixture was then extracted twice using 50 ml of ethyl acetate each. The organic layer was dried over $MgSO_4$ and evaporated to give 3.40 g of 71. $R_t$=0.98 min (Method Q).

f) 2-Methyl-propane-2-sulfinic acid 1-[4-(tert-butyl-dimethyl-silanyloxy)-1-trifluoromethyl-cyclohexyl]-methylideneamide (72)

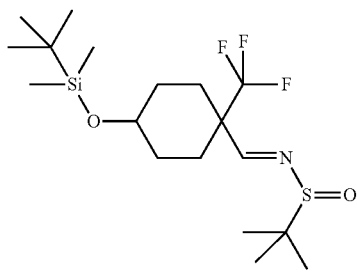 [SMILES: CC(C)(C)S(=O)/N=C/C1(C(F)(F)F)CCC(O[Si](C)(C)C(C)(C)C)CC1]

3.20 g (10.3 mmol) of 4-(tert-Butyl-dimethyl-silanyloxy)-1-trifluoromethyl-cyclohexanecarbaldehyde (71) were dissolved using 25 ml of anhydrous THF. 1.31 g (10.8 mmol) of 2-methyl-2-propanesulfinamide and 4.32 ml (20.6 mmol) of titanium (IV) ethoxide were added and the mixture heated for 4 h at reflux. The reaction mixture was poured into 75 ml of a saturated aqueous solution of $NaHCO_3$ and the precipitate removed by filtration. The filtrate was extracted three times using 50 ml of ethyl acetate each. The organic layer was dried using $MgSO_4$ and evaporated to yield 3.90 g of 72. $R_t$=1.02 min (Method Q).

g) 2-Methyl-propane-2-sulfinic acid {1-[4-(tert-butyl-dimethyl-silanyloxy)-1-trifluoromethyl-cyclohexyl]propyl}-amide (73)

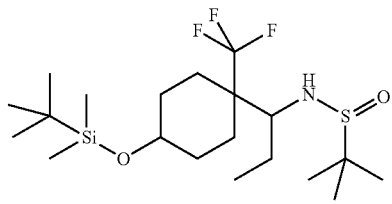 [SMILES: CCC(NS(=O)C(C)(C)C)C1(C(F)(F)F)CCC(O[Si](C)(C)C(C)(C)C)CC1]

13.4 ml (26.8 mmol) of a 2M solution of ethylmagnesium chloride in diethyl ether were diluted using 8 ml of anhydrous diethyl ether and cooled to −78° C. At that temperature, a solution of 3.7 g (8.95 mmol) of 2-methyl-propane-2-sulfinic acid 1-[4-(tert-butyl-dimethyl-silanyloxy)-1-trifluoromethyl-cyclohexyl]methylideneamide (72) in anhydrous diethyl ether was added dropwise. Afterwards, the mixture was allowed to warm to ambient temperature and was stirred for 2 h at ambient temperature. 100 ml of a saturated aqueous $Na_2SO_4$-solution was added, the organic layer separated, dried using $MgSO_4$ and evaporated to give 3.22 g of 73 as an oil, used without further purification. $R_t$=1.09 min (Method Q).

h) 4-(1-Amino-propyl)-4-trifluoromethyl-cyclohexanol (74)

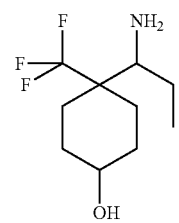

3.22 g (7.26 mmol) of 2-Methyl-propane-2-sulfinic acid {1-[4-(tert-butyl-dimethyl-silanyloxy)-1-trifluoromethyl-cyclohexyl]-propyl}-amide (73) were dissolved using 200 ml of 2-propanol. 60 ml of a 10% aqueous solution of HCl was added and the mixture was stirred for 5 h at ambient temperature and the mixture allowed to stand at ambient temperature for 16 h. Afterwards, 300 ml of a saturated aqueous solution of $K_2HPO_4$ were added and the 2-propanol evaporated. The resulting mixture was extracted twice using 100 ml of ethyl acetate each. The organic layer was dried using $MgSO_4$ and evaporated to yield 1.50 g of 74 as an oil, used without further purification. $R_t$=0.82 min (Method P).

i) 1-[4-(7-Chloro-1-methoxy-isoquinolin-6-yloxy)-1-trifluoromethyl-cyclohexyl]-propylamine (75)

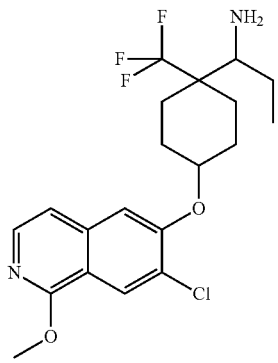 [SMILES: CCC(N)C1(C(F)(F)F)CCC(Oc2cc3ccnc(OC)c3cc2Cl)CC1]

160 mg (4.00 mmol) of NaH were suspended using 3 ml of DMA and a solution of 300 mg (1.33 mmol) of 4-(1-Amino-propyl)-4-trifluoromethyl-cyclohexanol (74) in 3 ml of DMA added. The mixture was stirred for 1 h at ambient temperature. Afterwards, a solution of 282 mg (1.33 mmol) of 7-chloro-6-fluoro-1-methoxy-isoquinoline in 4 ml of DMA was added and the mixture was stirred for 3 h at ambient temperature. The mixture was then poured into 100 ml of a saturated aqueous solution of $NaHCO_3$ and extracted three times using 50 ml of ethyl acetate each. The organic layer was washed twice using 50 ml of water, dried using MgSO₄ and evaporated. Chromatography on silica gel using ethyl acetate/n-heptane, followed by chromatography on silica gel using t-butylmethyl ether/n-heptane 1:1+1% acetic acid yielded 162 mg of the desired product as the acetate. $R_t$=0.77 min (Method P).

k) 6-[4-(1-Amino-propyl)-4-trifluoromethyl-cyclohexyloxy]-7-chloro-2H-isoquinolin-1-one (Isomer 1) (Example 103)

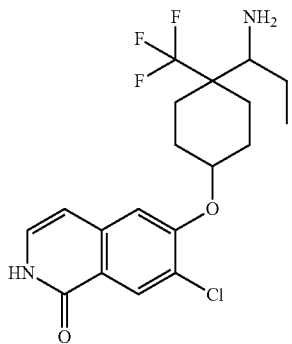 [SMILES: CCC(N)C1(C(F)(F)F)CCC(Oc2cc3cc[nH]c(=O)c3cc2Cl)CC1]

229 mg (480 mmol) of 1-[4-(7-Chloro-1-methoxy-isoquinolin-6-yloxy)-1-trifluoromethyl-cyclohexyl]-propylamine (75) were dissolved using 2 ml of 2-propanol and 2 ml of a 1N aqueous solution of HCl. The mixture was treated for 1 h at 100° C. under microwave irradiation. Afterwards, the mixture was diluted using 50 ml of water and lyophilized to yield 195 mg of Example 103 as the hydrochloride. $R_t$=0.64 min (Method P). Detected mass: 403.10 (M+H⁺).

Example 104

6-[4-(1-Amino-propyl)-4-trifluoromethyl-cyclohexyloxy]-7-chloro-2H-isoquinolin-1-one (Isomer 2)

a) 7-chloro-6-hydroxy-1-methoxyisoquinoline (81)

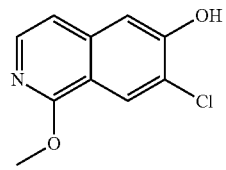

A solution of sodium trimethylsilanoate (149.2 mL, 1M in THF) was added to a solution of 7-chloro-6-fluoro-1-methoxyisoquinoline (4, 10 g, 47.2 mmol) in DMA (200 mL) under argon. After stirring at 60° C. for 24 hours, the solution was evaporated under reduced pressure and then freeze dried to give crude product (20.4 g). This was dissolved in water and the pH adjusted to pH=6.5. A light brown precipitate was collected by filtration and purified by reverse phase chromatography (0 to 4 minutes, 15% acetonitrile/water, 4 to 24 minutes 15 to 90% acetonitrile/water and then 100% acetonitrile) to give 7 g of the desired product $R_t$=2.60 min (Method C). Detected mass: 210.0 (M+H⁺).

b) 1-[4-(7-Chloro-1-methoxy-isoquinolin-6-yloxy)-1-trifluoromethyl-cyclohexyl]-propylamine (76)

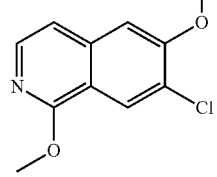

790 mg (3.51 mmol) of 4-(1-Amino-propyl)-4-trifluoromethyl-cyclohexanol (74) were dissolved using 8.0 ml of anhydrous THF. 1.20 g (4.56 mmol) of triphenylphosphin, 0.58 ml (3.51 mmol) of N,N-diisopropylethylamine, and 735 mg (3.51 mmol) of 7-chloro1-methoxy-isoquinolin-6-ol (81) were added and the mixture cooled to 0° C. At this temperature, 0.83 ml (5.26 mmol) of diethyl azodicarboxylate were added and the mixture stirred for 16 h at ambient temperature. Afterwards, the mixture was diluted with 20 ml of CH₂Cl₂ and washed successively with 20 ml of a 1N aqueous solution of NaOH, with 20 ml of a saturated aqueous solution of NH₄Cl, using 20 ml of water, and with 20 ml of a saturated aqueous solution of NaCl, respectively. The organic layer was then treated with 20 ml of a 1N aqueous solution of HCl. Crude product precipitated, was filtered off and resuspended in 20 ml of a 1N aqueous solution of NaOH. This suspension was extracted three times using 20 ml of CH₂Cl₂. The organic layer was then dried using MgSO₄ and evaporated. Chromatography of the residue on silica gel using t.-butylmethyl ether/n-heptane 1:1+1% acetic acid yielded 160 mg of the desired product as its acetate. $R_t$=0.79 min (Method P). Detected mass: 417.2 (M+H⁺).

c) 6-[4-(1-Amino-propyl)-4-trifluoromethyl-cyclohexyloxy]-7-chloro-2H-isoquinolin-1-one (Isomer 2) (Example 104)

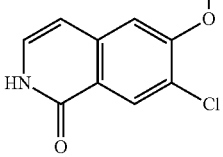

160 mg (336 mmol) of 1-[4-(7-Chloro-1-methoxy-isoquinolin-6-yloxy)-1-trifluoromethyl-cyclohexyl]-propylamine (76) were dissolved using 2 ml of 2-propanol and 2 ml of a 1N aqueous solution of HCl. The mixture was treated for 1 h at 100° C. under microwave irradiation. Afterwards, the mixture was diluted using 50 ml of water and lyophilized to yield 154 mg of the desired product. $R_t$=0.66 min (Method P). Detected mass: 403.2 (M+H⁺).

Example 111

[4-(1-Amino-propyl)-4-methyl-cyclohexyl]-isoquinolin-6-yl-amine a) [1-(8-Methyl-1,4-dioxa-spiro[4.5]dec-8-yl)-propyl]carbamic acid benzyl ester (77)

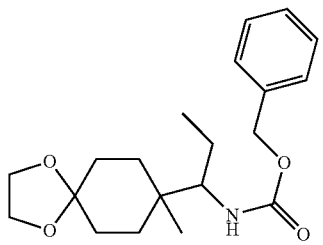 [SMILES: CCC(NC(=O)OCc1ccccc1)C1(C)CCC2(CC1)OCCO2]

7.50 g (41.4 mmol) of 8-Methyl-1,4-dioxa-spiro[4.5]decane-8-carbonitrile (synthesized from 1,4-dioxa-spiro[4.5]decane-8-carbonitrile and methyl iodide in a similar fashion as described for 5) were dissolved in 17 mL of absolute tetrahydrofurane. Then, 20.7 mL (62.1 mmol) of ethylmagnesium chloride (3M in diethylether) were added dropwise and the reaction mixture was heated to reflux for 8 h. After cooling to 0° C., 20 mL of dry methanol were added. After a period of 10 min, 2.56 g (67.7 mmol) of sodium borohydride were added portionwise at 0° C. and the mixture was stirred for 16 h at room temperature. The reaction was quenched by addition of 1M aqueous sodium hydroxide solution (200 mL) and extracted twice with diethylether (150 mL each). The combined organic phases were dried over magnesium sulphate, filtered and the solvent evaporated.

The crude amine (8.20 g) was dissolved in 115 mL of dry dichloromethane, cooled to −78° C. and 5.89 mL (4.28 g, 42.3 mmol) of triethylamine and 6.49 mL. (6.56 g, 38.4 mmol) of benzylchloroformate were added. The reaction mixture was warmed to room temperature and stirred for 2 h. Then, 100 mL of water were added and the mixture was extracted three times with dichloromethane. The combined organic phases were dried over magnesium sulphate, filtered and concentrated to give the crude product 77, which was purified by silica gel chromatography (heptane:ethyl acetate) to give 5.50 g of pure desired product (77). $R_t$=1.03 min (Method P). Detected mass: 348.2 (M+H$^+$).

b) [1-(1-Methyl-4-oxo-cyclohexyl)-propyl]-carbamic acid benzyl ester (78)

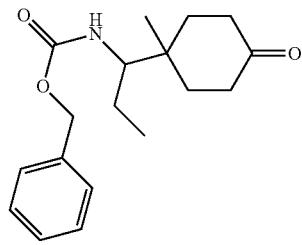 [SMILES: CCC(NC(=O)OCc1ccccc1)C1(C)CCC(=O)CC1]

5.50 g of [1-(8-methyl-1,4-dioxa-spiro[4.5]dec-8-yl)-propyl]-carbamic acid benzyl ester (77) were dissolved in 15 mL of a 2:1 mixture of acetone and 6N aqueous hydrochloric acid. The reaction mixture was stirred for 16 h at room temperature, then dropped into 150 mL of saturated aqueous sodium bicarbonate solution. The mixture was extracted three times with dichloromethane (100 mL each), the combined organic phases were dried over magnesium sulphate, filtered and concentrated to give the ketone 78, which was used directly in the next step. $R_t$=0.59 min (Method P). Detected mass: 304.2 (M+H$^+$).

c) [1-(4-Amino-1-methyl-cyclohexyl)-propyl]-carbamic acid benzyl ester (79)

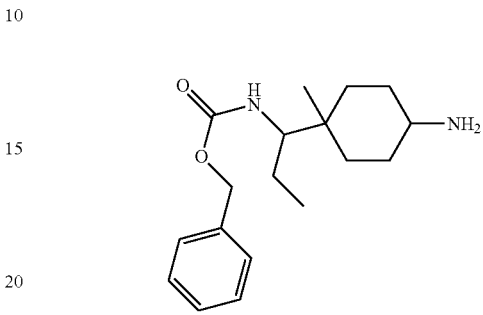

2.10 g (6.92 mmol) of the ketone (78) were dissolved in 21 mL of absolute methanol, then 5.34 g (69.2 mmol) of ammonium acetate and 435 mg (6.92 mmol) of sodium cyanoborohydride were added, and the mixture was stirred at room temperature for 16 h. The reaction mixture was evaporated, the residue dissolved in 50 mL of 1N aqueous sodium hydroxide and extracted twice with 100 mL of dichloromethane. The combined organic layer was dried over magnesium sulphate, filtered, and evaporated to give 1.70 g of the title compound 79 in a purity sufficient to be used directly in the next step. $R_t$=0.75 min (Method P). Detected mass: 305.2 (M+H$^+$).

d) {1-[4-(Isoquinolin-6-ylamino)-1-methyl-cyclohexyl]-propyl}-carbamic acid benzyl ester (80)

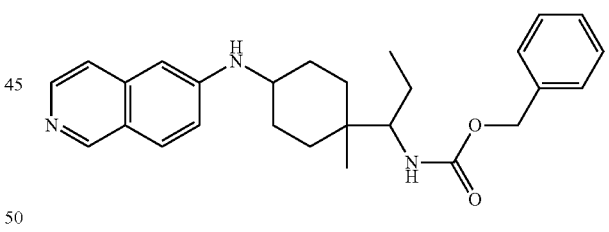

In 2 mL of absolute toluene were dissolved 100 mg (481 μmol) of 6-bromo-isoquinoline, 176 mg (577 μmol) of [1-(4-amino-1-methyl-cyclohexyl)-propyl]-carbamic acid benzyl ester (79), and 235 mg (721 μmol) of cesium carbonate. The solution was degassed twice, then 3.24 mg (14.4 μmol) of palladium acetate and 13.5 mg (21.6 μmol) of 2,2'-bis(diphenylphosphino)-1,1'-binaphthyl were added and the reaction mixture was heated to 100° C. until complete conversion could be observed. The mixture was evaporated, the residue dissolved in 50 mL of dichloromethane and washed twice with 50 mL of saturated aqueous sodium bicarbonate solution. The organic phase was dried over magnesium sulphate, filtered, concentrated and purified by silica gel chromatography (dichloromethane:methanol) to give 66 mg of the pure desired product. $R_t$=1.32 min (Method O). Detected mass: 432.3 (M+H$^+$).

e) [4-(1-Amino-propyl)-4-methyl-cyclohexyl]-isoquinolin-6-yl-amine (Example 111)

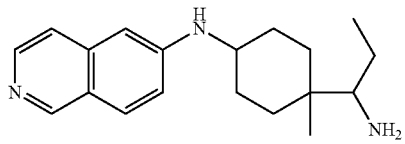 [SMILES: CCC(N)C1(C)CCC(Nc2ccc3cnccc3c2)CC1]

66 mg (153 μmol) of {1-[4-(Isoquinolin-6-ylamino)-1-methyl-cyclohexyl]-propyl}-carbamic acid benzyl ester (80) were dissolved in 500 μL of dry methanol and 5 mg of palladium on activated charcoal (10%) were added. The mixture was stirred under a hydrogen atmosphere until conversion was complete. The catalyst was filtered off and the reaction mixture was evaporated to dryness to give the title compound, which was purified by reversed phase HPLC (water/acetonitrile) to give 30 mg of pure Example 111 as its trifluoroacetic acid salt. $R_t$=1.02 min (Method L). Detected mass: 298.2 ($M+H^+$).

The following racemates were separated by HPLC, using a chiral column. Absolute stereochemistry was not determined, the earlier eluting enantiomer was designated to be enantiomer one.

| Example No. | Racemate | Enantiomer | Method | $R_t$ chiral [min] |
|---|---|---|---|---|
| 32 | Example 26 | 1 | E | 8.68 |
| 33 | Example 26 | 2 | E | 9.98 |
| 105 | Example 1 | 1 | T | 8.33 |
| 106 | Example 1 | 2 | T | 11.3 |
| 107 | Example 34 | 1 | R | 6.31 |
| 108 | Example 34 | 2 | R | 8.30 |
| 109 | Example 16 | 1 | S | 6.56 |
| 110 | Example 16 | 2 | S | 10.6 |

The enantiomers obtained from these examples by separation of the racemate are
cis-6-[4-((S)-1-Amino-propyl)-4-methyl-cyclohexyloxy]-7-chloro-2H-isoquinolin-1-one,
cis-6-[4-((R)-1-Amino-propyl)-4-methyl-cyclohexyloxy]-7-chloro-2H-isoquinolin-1-one,
cis-6-[4-((S)-1-Amino-propyl)-4-(tetrahydro-pyran-4-yl)-cyclohexyloxy]-7-chloro-2H-isoquinolin-1-one,
cis-6-[4-((R)-1-Amino-propyl)-4-(tetrahydro-pyran-4-yl)-cyclohexyloxy]-7-chloro-2H-isoquinolin-1-one,
cis-6-[4-((R)-1-Amino-propyl)-4-ethyl-cyclohexyloxy]-7-chloro-2H-isoquinolin-1-one,
cis-6-[4-((S)-1-Amino-propyl)-4-ethyl-cyclohexyloxy]-7-chloro-2H-isoquinolin-1-one,
cis-6-[4-((S)-Amino-cyclopropyl-methyl)-4-cyclopropylmethyl-cyclohexyloxy]-7-chloro-2H-isoquinolin-1-one, and
cis-6-[4-((R)-Amino-cyclopropyl-methyl)-4-cyclopropylmethyl-cyclohexyloxy]-7-chloro-2H-isoquinolin-1-one.
(The enantiomers have not been assigned to "Enantiomer 1" or "Enantiomer 2", respectively)
Methods
Method A:
Stationary phase: Waters XBridge C18
Gradient: ACN+0.05% TFA:H₂O+0.05% TFA 5:95 (0 min) to 5:95 (0.3 min) to 95:5 (3.5 min) to 95:5 (4 min)
Flow: 1.3 mL/min Method B:
Stationary phase: Col YMC Jsphere ODS H80 20×2
Gradient: ACN:H₂O+0.05% TFA 4:96 (0 min) to 95:5 (2.0 min) to 95:5 (2.4 min)
Flow: 1 mL/min
Method C:
Stationary phase: Col YMC Jsphere 33×2.1
Gradient: ACN+0.05% TFA:H₂O+0.05% TFA 2:98 (0 min) to 2:98 (1 min) to 95:5 (5 min) to 95:5 (6.25 min)
Flow: 1 mL/min
Method D:
Stationary phase: Waters XBridge C18
Gradient: ACN+0.1% FA:H₂O+0.08% FA 3:97 (0 min) to 60:40 (3.5 min) to 98:2 (4.0 min) to 98:2 (5.0 min) to 3:97 (5.2 min) to 3:97 (6.5 min)
Flow: 1.3 mL/min
Method E:
Stationary phase: Chiralpak IA 250×4.6 mm
Heptane:EtOH MeOH 5:1:1+0.1% diethyl amine
Method F:
Stationary phase: Luna 3μ C18(2) 10×2.0 mm
Gradient: ACN:H₂O+0.05% TFA 7:93 (0 min) to 95:5 (1.2 min) to 95:5 (1.4 min)
Flow: 1.1 mL/min
Method G:
Stationary phase: Merck Chromolith fast Grad
Gradient: H₂O+0.05% TFA:ACN+0.035% TFA 98:2 (0 min) to 98:2 (0.2 min) to 2:98 (2.4 min) to 2:98 (3.2 min) to 98:2 (3.3 min) to 98:2 (4 min)
Flow: 2 mL/min
Method H:
Stationary phase: Waters XBridge C18
Gradient: H₂O+0.05% TFA:ACN+0.05% TEA 95:5 (0 min) to 5:95 (3.3 min) to 5:95 (3.85 min) to 95:5 (4.3 min)
Flow: 1.7 mL/min
Method I:
Stationary phase: Waters XBridge C18
Gradient: H₂O+0.05% TFA ACN+0.05% TFA 95:5 (0 min) to 5:95 (3.3 min) to 5:95 (3.85 min) to 95:5 (4 min)
Flow: 1.7 mL/min
Method J:
Stationary phase: Waters XBridge C18
Gradient: H₂O+0.05% TFA:ACN+0.05% TFA 95:5 (0 min) to 5:95 (2.6 min) to 5:95 (3.0 min) to 95:5 (3.1 min) to 95:5 (4.0 min)
Flow: 1.7 mL/min
Method K:
Stationary phase: Waters XBridge C18
Gradient: H₂O+0.05% TFA ACN+0.05% TFA 95:5 (0 min) to 95:5 (0.2 min) to 5:95 (2.4 min) to 5:95 (32 min) to 95:5 (3.3 min) to 95:5 (4.0 min)
Flow: 1.7 mL/min
Method L:
Stationary phase: Merck Chromolith fast Grad
Gradient: H₂O+0.05% TFA:ACN+0.05% TFA 98:2 (0 min) to 98:2 (0.2 min) to 2:98 (2.4 min) to 2:98 (3.2 min) to 98:2 (3.3 min) to 98:2 (4 min)
Flow: 2.4 mL/min
Method M:
Stationary phase: Waters Aquity SDS
Gradient: H₂O+0.1% FA:ACN+0.08% FA 95:5 (0 min) to 5:95 (1.1 min) to 5:95 (1.7 min) to 95:5 (1.8 min) to 95:5 (2.0 min)
Flow: 0.9 mL/min Method N:
Stationary phase: Waters XBridge C18
Gradient: H₂O+0.05% TFA:ACN+0.05% TFA 95:5 (0 min) to 95:5 (0.2 min) to 5:95 (2.4 min) to 5:95 (3.5 min) to 95:5 (3.6 min) to 95:5 (4.5 min)
Flow: 1.7 mL/min
Method O:
Stationary phase: Col YMC Jsphere ODS H80 20×2
Gradient: ACN:H₂O+0.05% TFA 4:96 (0 min) to 95:5 (2.0 min) to 95:5 (2.4 min) to 4:96 (2.45 min)
Flow: 1 mL/min
Method P:
Stationary phase: Luna 3μ C18(2) 10×2.0 mm
Gradient: ACN:H₂O+0.05% TFA 7:93 (0 min) to 95:5 (1.2 min) to 95:5 (1.4 min) to 7:93 (1.45 min)
Flow: 1.1 mL/min
Method Q:
Stationary phase: Luna 3μ C18(2) 10×2.0 mm
Gradient: ACN: H₂O+0.05% TFA 20:80 (0 min) to 95:5 (0.8 min) to 95:5 (1.4 min) to 20:80 (1.45 min)
Flow: 1.1 mL/min
Method R:
Stationary phase: Chiralpak AD-H/83, 250×4.6 mm.
Eluent: MeOH:EtOH (1:1)+0.1% diethylamine.
Flow: 1 mL/min
Detection: 249 nM
Method S:
Stationary phase: Chiralpak AD-H/55, 250×4.6 mm.
Eluent: MeOH:EtOH (1:1)+0.1% diethylamine.
Flow: 1 mL/min
Detection: 249 nM
Method T:
Stationary phase: IA 250×4.6 mm
Eluent: Heptane:EtOH:MeOH (1:1:1)+0.1% diethylamine
Flow: 1 mL/min
Detection: 249 nM
Method U:
Stationary phase: Merck Chromolith fast grad
Gradient: Water+0.05% TFA:ACN+0.05% TFA 98:2 (0 min) to 98:2 (0.2 min) to 2:98 (2.4 min)
Flow 1.3 mL/min 1) Determination of Rho Kinase Inhibition To measure Rho-kinase inhibition, IC₅₀ values were determined according to the following protocol:

Active human recombinant ROCK II (N-terminal His6-tagged recombinant human ROCK-II residues 11-552) was purchased from Millipore GmbH, Schwalbach, Germany. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-hydroxyethyl)piperazine-1-ethanesulfonic acid (Hepes), Brij-35, dithiothreitol (DTT) and Pluronic F-68 were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany. Test compounds were diluted to the appropriate concentrations in buffer 1 (25 mM Tris-HCl, pH 7.4, 5 mM MgCl₂, 2 mM DTT, 0.02% (w/v) BSA, 0.01% Pluronic F-68 and 3% DMSO). The ROCK II enzyme was diluted to a concentration of 100 ng/mL in buffer 2 (25 mM Tris-HCl, pH 7.4, 5 mM MgCl₂, 2 mM DTT and 0.02% (w/v) BSA). The peptide substrate and ATP were diluted to concentrations of 3 μM and 120 μM, respectively, in the buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 2004, 9(5), 409-416). Separation conditions were as follows: Pressure –1.3 psi, upstream voltage –1562 V, downstream voltage –500 V, sample sip time 200 ms. Positive controls (buffer 1 instead of compound) and negative controls (buffer 1 instead of compound and buffer 2 instead of ROCK II) were run in parallel on each plate.

The following products/compounds were tested in said assay by using the respective form (salt or free base) obtained as in the examples described above and the following activities were measured

| Example-No. | pIC50 |
|---|---|
| 1 | +++++++ |
| 2 | +++++ |
| 3 | +++++++ |
| 4 | ++++++ |
| 5 | +++++++ |
| 6 | +++++++ |
| 7 | ++++++ |
| 8 | +++++++ |
| 9 | ++++++ |
| 10 | +++++++ |
| 11 | ++++++ |
| 12 | +++++++ |
| 13 | ++++++ |
| 14 | +++++++ |
| 15 | ++++++ |
| 16 | +++++++ |
| 17 | ++++++ |
| 18 | +++++++ |
| 19 | ++++++ |
| 20 | +++++ |
| 21 | ++++++ |
| 22 | ++++++ |
| 23 | +++++ |
| 24 | ++++++ |
| 25 | ++++++ |
| 26 | +++++++ |
| 27 | ++++++ |
| 28 | +++++ |
| 29 | ++++++ |
| 30 | ++++++ |
| 31 | ++++++ |
| 32 | +++++++ |
| 33 | +++++++ |
| 34 | +++++++ |
| 35 | ++++++ |
| 37 | ++++++ |
| 38 | +++++++ |
| 39 | +++++ |
| 40 | +++++ |
| 41 | +++++ |
| 46 | +++++ |
| 47 | ++++++ |
| 50 | ++++++ |
| 51 | +++++ |
| 52 | +++++ |
| 53 | +++++ |
| 54 | +++++ |
| 56 | +++++ |
| 57 | +++++ |
| 58 | ++++++ |
| 59 | ++++++ |
| 60 | ++++++ |

| Example-No. | pIC50 |
| --- | --- |
| 61 | ++++++ |
| 62 | +++++++ |
| 63 | +++++ |
| 64 | +++++++ |
| 65 | ++++++ |
| 66 | +++++++ |
| 67 | ++++++ |
| 68 | +++++++ |
| 69 | +++++++ |
| 70 | +++++++ |
| 71 | +++++++ |
| 72 | ++++++ |
| 73 | +++++++ |
| 74 | +++++++ |
| 75 | +++++++ |
| 76 | +++++++ |
| 77 | +++++++ |
| 78 | ++++++ |
| 79 | +++++ |
| 80 | +++++ |
| 81 | +++++ |
| 82 | +++++ |
| 84 | +++++ |
| 85 | +++++ |
| 86 | +++++ |
| 87 | +++++ |
| 88 | +++++ |
| 89 | +++++ |
| 90 | ++++++ |
| 95 | +++++++ |
| 96 | ++++++ |
| 97 | +++++ |
| 98 | ++++++ |
| 99 | +++++++ |
| 100 | +++++ |
| 103 | +++++++ |
| 104 | +++++ |
| 105 | ++++++ |
| 106 | +++++++ |
| 107 | +++++++ |
| 108 | +++++++ |

The given activity is denoted as the negative decadal logarithm of the $IC_{50}$ ($pIC_{50}$) as follows:
+: $pIC50 \leq 3.0$
++: $3.0 \leq pIC_{50} < 4.0$
+++: $4.0 \leq pIC_{50} < 5.0$
++++: $5.0 \leq pIC_{50} < 6.0$
+++++: $6.0 \leq pIC50 < 7.0$
++++++: $7.0 \leq pIC50 < 8.0$
+++++++: $8.0 \leq pIC50$ 2) Determination of Protein Kinase a and Protein Kinase G Inhibition To measure PKA and PKG1-beta inhibition, $IC_{50}$ values were determined according to the following protocol:

Active recombinant human PKG1-beta (full-length, with N-terminal His-tag) was purchased from Millipore GmbH, Schwalbach, Germany. Active recombinant human PKA (residues 1-351, N-terminal His-tag) was obtained from Invitrogen, Karlsruhe, Germany. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-Hydroxyethyl)piperazine-1-ethanesulfonic acid (Hepes), Brij-35, dithiothreitol (DTT) and Pluronic F-68 were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany. Test compounds were diluted to the appropriate concentrations in buffer 1 (25 mM Tris-HCl, pH 7.4, 5 mM $MgCl_2$, 2 mM DTT, 0.02% (w/v) BSA, 0.01% Pluronic F-68 and 3% DMSO). PKG1-beta and PKA were diluted to concentrations of 150 ng/ml and 30 ng/ml, respectively, in buffer 2. The peptide substrate and ATP were diluted to concentrations of 3 μM and 120 μM, respectively, in the buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 9(5), 409-416, 2004). Separation conditions were as follows: Pressure −1.3 psi, upstream voltage −1562 V, downstream voltage −500 V, sample sip time 200 ms, Positive controls (buffer 1 instead of compound) and negative controls (buffer 1 instead of compound and buffer 2 instead of kinase solution) were run in parallel on each plate. The following products/compounds were tested in said assay by using the respective form (salt or free base) obtained as in the examples described above and the following activities were measured.

| Example No. | Selectivity against PKA | Selectivity against PKG |
| --- | --- | --- |
| 1 | >1000 fold | >300 fold |
| 2 | >10 fold | >1 fold |
| 3 | >1000 fold | >1000 fold |
| 4 | >300 fold | >100 fold |
| 5 | >1000 fold | >1000 fold |
| 6 | >1000 fold | >1000 fold |
| 7 | >300 fold | >100 fold |
| 8 | >100 fold | >100 fold |
| 9 | >10 fold | >10 fold |
| 10 | >1000 fold | >300 fold |
| 11 | >100 fold | >300 fold |
| 12 | >1000 fold | >300 fold |
| 13 | >10 fold | >10 fold |
| 14 | >1000 fold | >100 fold |
| 15 | >10 fold | >10 fold |
| 16 | >300 fold | >300 fold |
| 17 | >10 fold | >10 fold |
| 18 | >300 fold | >300 fold |
| 19 | >1000 fold | >300 fold |
| 21 | >300 fold | >100 fold |
| 22 | >300 fold | >100 fold |
| 23 | >10 fold | >10 fold |
| 25 | >300 fold | >100 fold |
| 27 | >1000 fold | >1000 fold |
| 28 | >10 fold | >10 fold |
| 30 | >300 fold | >10 fold |
| 31 | >10 fold | >100 fold |
| 32 | >1000 fold | >300 fold |
| 33 | >1000 fold | >1000 fold |
| 34 | >1000 fold | >300 fold |
| 35 | >300 fold | >10 fold |
| 37 | >300 fold | >100 fold |
| 38 | >1000 fold | >300 fold |
| 47 | >300 fold | >300 fold |
| 50 | >300 fold | >10 fold |
| 52 | >100 fold | >10 fold |
| 54 | >10 fold | >10 fold |
| 58 | >300 fold | >300 fold |
| 59 | >100 fold | >100 fold |
| 61 | >100 fold | >300 fold |
| 62 | >1000 fold | >100 fold |
| 64 | >1000 fold | >300 fold |
| 65 | >300 fold | >100 fold |
| 68 | >1000 fold | >300 fold |
| 69 | >1000 fold | >300 fold |

-continued

| Example No. | Selectivity against PKA | Selectivity against PKG |
|---|---|---|
| 70 | >1000 fold | >1000 fold |
| 72 | >300 fold | >100 fold |
| 73 | >1000 fold | >300 fold |
| 74 | >1000 fold | >1000 fold |
| 75 | >1000 fold | >1000 fold |
| 76 | >1000 fold | >1000 fold |
| 77 | >1000 fold | >300 fold |
| 78 | >300 fold | >100 fold |
| 90 | >300 fold | >100 fold |
| 95 | >1000 fold | >300 fold |
| 96 | >300 fold | >100 fold |
| 99 | >1000 fold | >300 fold |
| 103 | >1000 fold | >1000 fold |
| 106 | >1000 fold | >1000 fold |
| 107 | >1000 fold | >1000 fold |
| 108 | >1000 fold | >10 fold |
| 109 | >300 fold | >100 fold |
| 110 | >1000 fold | >1000 fold |

The invention claimed is:
1. A compound of the formula (I)

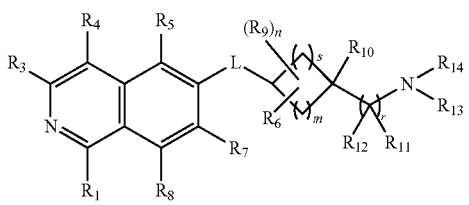

wherein
$R_1$ is H, OH or $NH_2$;
$R_3$ is H, halogen, CN, $(C_1-C_6)$alkyl, OH, $NH_2$, or NHR';
$R_4$ is H, halogen, hydroxy, CN, $(C_1-C_6)$alkyl, R', or $(C_1-C_6)$alkylene-R';
$R_5$ is H, halogen, CN, $(C_1-C_6)$alkyl, or R';
$R_7$ is H, halogen, CN, $(C_1-C_6)$alkyl, O—$(C_1-C_6)$alkyl, R', or $SO_2$—$NH_2$;
$R_8$ is H, halogen or $(C_1-C_6)$alkyl;
$R_9$ is
R',
OH,
halogen,
$(C_1-C_6)$alkyl,
O—$(C_1-C_6)$alkyl,
$(C_1-C_6)$alkylene-R',
$(C_2-C_6)$alkenyl,
$(C_2-C_6)$alkynyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)$NH_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
COOH,
C(O)O—$(C_1-C_6)$alkyl,
C(O)OR',
C(O)$(C_1-C_6)$alkyl,
C(O)R',
C(O)$NH_2$,
C(O)—NH—$(C_2-C_6)$alkenyl,
C(O)—NH—$(C_2-C_6)$alkynyl,
C(O)NH—$(C_1-C_6)$alkyl,
C(O)NHR',
C(O)—NH$(C_1-C_6)$alkylene-R',
C(O)N[$(C_1-C_6)$alkyl]R'
C(O)N[$(C_1-C_6)$alkyl]$_2$,
C(O)—$(C_1-C_6)$alkylene-R', or
C(O)O$(C_1-C_6)$alkylene-R',
$R_6$ is absent;
or is one $(C_1-C_4)$alkylene bound to the cycloalkyl ring, in which the $(C_1-C_4)$alkylene forms a second bond to a different carbon atom of the cycloalkyl ring to form a bicyclic ring system, wherein in the bicyclic ring system optionally one or two carbon atoms are replaced by a group independently selected from O, N—$R_{15}$, S, SO or $SO_2$;
or, if m and s are 2, m is 3 and s is 1, or m is 4 and s is 0, $R_6$ is $CH_2$—CH—$(CH_2)_2$ which is bound with one $CH_2$ to the cycloalkyl ring and the two other $CH_2$ are bound to different carbon atoms of the cycloalkyl ring;
and, if m is 3 and s is 3,
$R_6$ are two methylene groups bound to different carbon atoms of the cycloalkyl ring, wherein the methylene groups or the $CH_2$—CH—$(CH_2)_2$ group are bound to carbon atoms of the cycloalkyl ring such that they form an adamantane system of the formula

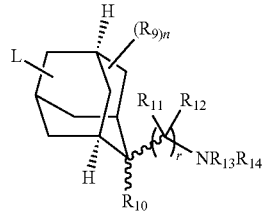

wherein L can be bound to any secondary or tertiary carbon atom and
wherein the bicyclic ring system or adamantane system is unsubstituted or optionally substituted by $R_9$;
$R_{10}$ is
$(C_1-C_6)$alkyl,
$(C_1-C_8)$heteroalkyl,
$(C_3-C_8)$cycloalkyl,
$(C_3-C_8)$heterocycloalkyl,
$(C_1-C_6)$alkylene-$(C_3-C_8)$cycloalkyl,
$(C_1-C_6)$alkylene-$(C_6-C_{10})$aryl,
$(C_1-C_6)$alkylene-$(C_5-C_{10})$heteroaryl,
$(C_1-C_6)$alkylene-$(C_3-C_8)$heterocycloalkyl,
C(O)NH—$(C_1-C_6)$alkyl,
C(O)N[$(C_1-C_6)$alkyl]$_2$
C(O)NH—R',
C(O)N—(($C_1-C_6$)alkyl)-R', or
C(O)NH—$(C_1-C_6)$alkylene-R';
$R_{11}$ is
H,
$(C_1-C_6)$alkyl,
$(C_1-C_6)$alkylene-R'
R',
or $R_{11}$ and $R_{12}$ together with carbon atom to which they are attached form a $(C_3-C_8)$cycloalkyl or a $(C_3-C_8)$-heterocycloalkyl ring;
$R_{12}$ is
$(C_1-C_6)$alkyl,
$(C_3-C_8)$cycloalkyl, ($C_5$-$C_{10}$)heteroaryl,
($C_3$-$C_8$)heterocycloalkyl, or
($C_6$-$C_{10}$)aryl;
or $R_{12}$ is H, provided that r=2 and the other $R_{12}$ is not H;
or $R_{11}$ and $R_{12}$ together with carbon atom to which they are attached form a ($C_3$-$C_8$)cycloalkyl or a ($C_3$-$C_8$)-heterocycloalkyl ring;
$R_{13}$ and $R_{14}$ are independently of each other
H,
R',
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)NH$_2$,
($C_1$-$C_6$)alkylene-C(O)NH—R',
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)N[R']$_2$,
($C_1$-$C_6$)alkylene-C(O)O—($C_1$-$C_6$)alkyl,
C(O)O—($C_1$-$C_6$)alkyl,
C(O)OR',
C(O)($C_1$-$C_6$)alkyl,
C(O)R',
C(O)NH—($C_1$-$C_6$)alkyl,
C(O)NHR',
C(O)N[($C_1$-$C_6$)alkyl]R'
C(O)N[($C_1$-$C_6$)alkyl]$_2$,
C(O)—($C_1$-$C_6$)alkylene-R',
C(O)O($C_1$-$C_6$)alkylene-R', or
$R_{13}$ and $R_{14}$, together with the N-atom to which they are attached, form a ($C_3$-$C_8$) heterocycloalkyl;
$R_{15}$ is H or ($C_1$-$C_6$)alkyl;
n is 0, 1, 2, 3 or 4;
m is 1, 2, 3 or 4;
s is 0, 1, 2, or 3;
r is 1 or 2;
L is O(CH$_2$)p, S(CH$_2$)p, S(O)(CH$_2$)p, SO$_2$(CH$_2$)p, NH(CH$_2$)p, N($C_1$-$C_6$)alkyl-(CH$_2$)p, N($C_3$-$C_6$)cycloalkyl-(CH$_2$)p; or N[($C_1$-$C_3$)alkylene-R']—(CH$_2$)p;
p is 0, 1, 2, 3 or 4;
R' is
($C_3$-$C_8$)cycloalkyl,
($C_5$-$C_{10}$)heteroaryl,
($C_3$-$C_8$)heterocycloalkyl,
($C_6$-$C_{10}$)aryl;
wherein in residues $R_3$ to $R_{15}$ alkyl or alkylene is unsubstituted or optionally substituted one or more times by OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues $R_3$ to $R_{15}$ cycloalkyl or heterocycloalkyl is unsubstituted or optionally substituted one or more times by ($C_1$-$C_6$)alkyl, halogen, OH, OCH$_3$, C(O) OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues $R_3$ to $R_{15}$ alkyl or alkylene is unsubstituted or optionally substituted one or more times by halogen;
wherein in residues $R_3$ to $R_{15}$ ($C_6$-$C_{10}$)aryl and ($C_5$-$C_{10}$) heteroaryl are unsubstituted or optionally substituted one or more times by a group independently selected from halogen, OH, NO$_2$, N$_3$, CN, O—($C_1$-$C_6$)alkyl, C(O)—($C_6$-$C_{10}$)aryl, C(O)OH, C(O)O($C_1$-$C_6$)alkyl, C(O)NH$_2$, C(O)NH($C_1$-$C_6$)alkyl, C(O)N[($C_1$-$C_6$) alkyl]$_2$, ($C_3$-$C_8$)cycloalkyl, ($C_1$-$C_6$)alkyl, ($C_1$-$C_6$)alkylene-NH($C_1$-$C_6$)alkyl, ($C_1$-$C_6$)alkylene-N[($C_1$-$C_6$) alkyl]$_2$, ($C_2$-$C_6$)alkenyl, ($C_2$-$C_6$)alkynyl, O—($C_1$-$C_6$) alkyl, O—C(O)—($C_1$-$C_6$)alkyl, PO$_3$H$_2$, SO$_3$H, SO$_2$—NH$_2$, SO$_2$NH($C_1$-$C_6$)alkyl, SO$_2$N[($C_1$-$C_6$)alkyl]$_2$, S—($C_1$-$C_6$)alkyl, SO—($C_1$-$C_6$)alkyl, SO$_2$—($C_1$-$C_6$) alkyl, SO$_2$—N—CH—N[($C_1$-$C_6$)alkyl]$_2$, SF$_5$, C(NH) (NH$_2$), NH$_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$) alkyl, NH—SO$_2$—($C_1$-$C_6$)alkyl, NH—SO$_2$—($C_6$-$C_{10}$) aryl, NH—SO$_2$—($C_5$-$C_{10}$)heteroaryl, NH—SO$_2$—($C_3$-$C_8$)heterocycloalkyl, N($C_1$-$C_6$)alkyl-C(O)—($C_1$-$C_6$) alkyl, N($C_1$-$C_6$)alkyl-C(O)O—($C_1$-$C_6$)alkyl, N($C_1$-$C_6$) alkyl-C(O)—NH—($C_1$-$C_6$)alkyl], ($C_6$-$C_{10}$)aryl, ($C_1$-$C_6$)alkylene-($C_6$-$C_{10}$)aryl, O—($C_6$-$C_{10}$)aryl, O—($C_1$-$C_6$)alkylene-($C_6$-$C_{10}$)aryl, ($C_5$-$C_{10}$)heteroaryl, ($C_3$-$C_8$) heterocycloalkyl, ($C_1$-$C_6$)alkylene-($C_5$-$C_{10}$)heteroaryl, ($C_1$-$C_6$)alkylene-($C_3$-$C_8$)heterocycloalkyl, O—($C_1$-$C_6$) alkylene-($C_5$-$C_{10}$)heteroaryl, O—($C_1$-$C_6$)alkylene-($C_3$-$C_8$)heterocycloalkyl, wherein said ($C_6$-$C_{10}$)aryl or ($C_5$-$C_{10}$)heteroaryl or ($C_3$-$C_8$)heterocycloalkyl or ($C_3$-$C_8$) cycloalkyl may be substituted one to three times by a group independently selected from halogen, OH, NO$_2$, CN, O—($C_1$-$C_6$)alkyl, ($C_1$-$C_6$)alkyl, NH$_2$, NH($C_1$-$C_6$) alkyl, N[($C_1$-$C_6$)alkyl]$_2$, SO$_2$CH$_3$, C(O)OH, C(O)O—($C_1$-$C_6$)alkyl, C(O)NH$_2$, ($C_1$-$C_6$)alkylene-O—($C_1$-$C_6$) alkyl, ($C_1$-$C_6$)alkylene-O—($C_6$-$C_{10}$)aryl, or O—($C_1$-$C_6$)alkylene-($C_6$-$C_{10}$)aryl;

or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to; and wherein aryl substituents of ($C_6$-$C_{10}$)aryl, ($C_5$-$C_{10}$)heteroaryl, cycloalkyl or ($C_3$-$C_8$)heterocycloalkyl groups may not be further substituted by an aryl, heteroaryl, cycloalkyl or heterocycloalkyl containing group;

their stereoisomeric and/or tautomeric forms or their pharmaceutically acceptable salts.

2. A compound of formula (I) according to claim 1, wherein $R_1$ is H and is characterized by the formula (II)

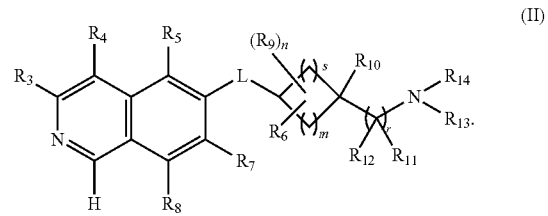

3. A compound of formula (I) according to claim 1, wherein $R_1$ is OH and is characterized by the formula (IIIa)

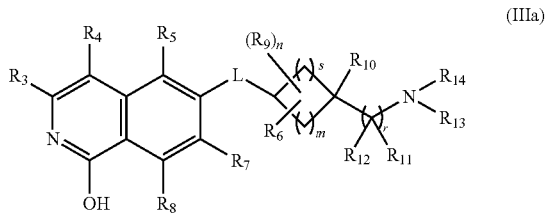

or by the formula (IIIb)

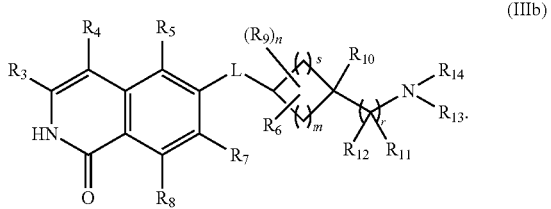

4. A compound according to claim 1, wherein $R_1$ is $NH_2$.
5. A compound according to one of claims 1 to 4, wherein $R_3$ is H, halogen, $(C_1-C_6)$alkyl, or NHR', wherein $(C_1-C_6)$alkyl and R' are unsubstituted or substituted.
6. A compound according to claim 1, wherein $R_3$ is H.
7. A compound according to claim 1, wherein $R_4$ is H, halogen, $(C_1-C_6)$alkyl or $(C_1-C_2)$alkenyl-phenyl, wherein $(C_1-C_6)$alkyl or phenyl are unsubstituted or substituted.
8. A compound according to claim 1, wherein $R_4$ is H.
9. A compound according to claim 1, wherein $R_5$ is H, halogen, $(C_1-C_6)$alkyl, $(C_6-C_{10})$aryl, $(C_3-C_8)$cycloalkyl or $(C_5-C_{10})$heteroaryl, wherein $(C_1-C_6)$alkyl, $(C_3-C_8)$cycloalkyl, $(C_6-C_{10})$aryl, or $(C_5-C_{10})$heteroaryl are unsubstituted or substituted.
10. A compound according to claim 1, wherein $R_5$ is H.
11. A compound according to claim 1, wherein $R_7$ is H, halogen, $(C_1-C_6)$alkyl, O—$(C_1-C_6)$alkyl, or R', wherein $(C_1-C_6)$alkyl or R' are unsubstituted or substituted.
12. A compound according to claim 1, wherein $R_7$ is hydrogen, methyl or chloro.
13. A compound according to claim 1, wherein $R_8$ is H.
14. A compound according to claim 1, wherein $R_9$ is
R',
OH,
halogen,
$(C_1-C_6)$alkyl,
$(C_1-C_6)$alkylene-R',
$(C_2-C_6)$alkenyl,
$(C_1-C_6)$alkylene-C(O)NH—R',
$(C_1-C_6)$alkylene-C(O)NH—$(C_1-C_6)$alkyl,
COOH,
$CONH_2$,
C(O)NH—$(C_1-C_6)$alkyl,
C(O)NHR',
C(O)—NH—$(C_1-C_6)$alkynyl,
C(O)—NH$(C_1-C_6)$alkylene-R', or
C(O)N[$(C_1-C_6)$alkyl]$_2$;
wherein $(C_1-C_6)$alkyl, $(C_1-C_6)$alkylene or R' are unsubstituted or substituted.
15. A compound according to claim 1, wherein $R_9$ is OH, halogen, $(C_1-C_6)$alkyl, C(O)OH, C(O)$NH_2$, or O—$CH_3$, wherein $(C_1-C_6)$alkyl is unsubstituted or substituted.
16. A compound according to claim 1, wherein $R_9$ is unsubstituted or substituted $(C_1-C_6)$alkyl.
17. A compound according to claim 1, wherein $R_{10}$ is
$(C_1-C_6)$alkyl,
$(C_1-C_8)$heteroalkyl,
$(C_3-C_8)$cycloalkyl,
$(C_3-C_8)$heterocycloalkyl,
$(C_1-C_6)$alkylene-$(C_3-C_8)$cycloalkyl,
$(C_1-C_6)$alkylene-phenyl,
$(C_1-C_6)$alkylene-$(C_5-C_6)$heteroaryl, or
$(C_1-C_6)$alkylene-$(C_5-C_6)$heterocycloalkyl, wherein $(C_1-C_6)$alkyl, $(C_1-C_8)$heteroalkyl, $(C_3-C_8)$cycloalkyl, $(C_3-C_8)$heterocycloalkyl, $(C_1-C_6)$alkylene, phenyl or $(C_5-C_{10})$heteroaryl are unsubstituted or substituted.
18. A compound according to claim 1, wherein $R_{10}$ is methyl, ethyl, propyl, isopropyl, butyl, isobutyl, cyclopropyl, cyclobutyl, cyclopentyl, cyclopropylmethylene, isopropyloxymethylene, tetrahydrofuranyl, tetrahydropyranyl or benzyl.
19. A compound according to claim 1, wherein $R_{11}$ is
H,
$(C_1-C_6)$alkyl,
$(C_3-C_8)$cycloalkyl, or
$(C_5-C_6)$heteroaryl,
wherein $(C_1-C_6)$alkyl, $(C_3-C_8)$cycloalkyl, or $(C_5-C_6)$heteroaryl are unsubstituted or substituted.
20. A compound according to claim 1, wherein $R_{11}$ is H or methyl.
21. A compound according to claim 1, wherein $R_{12}$ is
$(C_1-C_6)$alkyl, wherein optionally one or more hydrogen are substituted by fluoro;
$(C_3-C_8)$cycloalkyl,
$(C_5-C_6)$heteroaryl, or
$(C_{1-6}-C_{10})$aryl,
wherein $(C_3-C_8)$cycloalkyl, $(C_5-C_6)$heteroaryl or $(C_6-C_{10})$aryl are unsubstituted or substituted.
22. A compound according to claim 1, wherein $R_{12}$ is methyl, ethyl, propyl, isopropyl, cyclopropyl, trifluoromethyl, pentafluoroethyl, thiazolyl or phenyl.
23. A compound according to claim 1, wherein $R_{11}$ and $R_{12}$ form a substituted or unsubstituted $(C_3-C_8)$cycloalkyl ring.
24. A compound according to claim 1, wherein $R_{13}$ and $R_{14}$ are independently of each other
H,
$(C_1-C_6)$alkyl,
$(C_3-C_8)$cycloalkyl,
$(C_1-C_4)$alkylene-$(C_3-C_8)$cycloalkyl,
$(C_1-C_4)$alkylene-$(C_5-C_{10})$heteroaryl,
$(C_1-C_4)$alkylene-$(C_3-C_8)$heterocycloalkyl,
$C_1-C_4$)alkylene-$(C_6-C_{10})$aryl,
$(C_1-C_6)$alkylene-O—$(C_1-C_6)$alkyl,
C(O)NH—$(C_1-C_6)$alkyl, or
$R_{13}$ and $R_{14}$, together with the N-atom to which they are attached, form a $(C_3-C_8)$ heterocycloalkyl group,
wherein $(C_1-C_6)$alkyl, $(C_3-C_8)$cycloalkyl, $(C_1-C_4)$alkylene, $C_5-C_{10})$heteroaryl, $(C_3-C_8)$heterocycloalkyl, or $(C_6-C_{10})$aryl are unsubstituted or substituted.
25. A compound according to claim 1, wherein $R_{13}$ is H, $(C_1-C_6)$alkyl, $(C_3-C_8)$cycloalkyl, or $(C_1-C_4)$alkylene-$(C_3-C_8)$cycloalkyl; and $R_{14}$ is
H,
$(C_1-C_6)$alkyl,
$(C_3-C_8)$cycloalkyl,
$(C_1-C_4)$alkylene-$(C_3-C_8)$cycloalkyl,
$(C_1-C_4)$alkylene-$(C_5-C_{10})$heteroaryl,
$(C_1-C_4)$alkylene-$(C_3-C_8)$heterocycloalkyl,
$(C_1-C_4)$alkylene-$(C_6-C_{10})$aryl,
$(C_1-C_4)$alkylene-O—$(C_1-C_6)$alkyl, or
C(O)$(C_1-C_6)$alkyl,
wherein $(C_1-C_6)$alkyl, $(C_3-C_8)$cycloalkyl, $(C_1-C_4)$alkylene, $(C_5-C_{10})$heteroaryl, $(C_3-C_8)$heterocycloalkyl, or $(C_6-C_{10})$aryl are unsubstituted or substituted.
26. A compound according to claim 1, wherein
$R_{13}$ is H or $(C_1-C_6)$alkyl; and
$R_{14}$ is
H,
$(C_1-C_6)$alkyl, ($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
($C_1$-$C_4$)alkylene-($C_6$-$C_{10}$)aryl, or
($C_1$-$C_4$)alkylene-O—($C_1$-$C_6$)alkyl,
wherein ($C_1$-$C_6$)alkyl, ($C_3$-$C_8$)cycloalkyl, ($C_1$-$C_4$)alkylene, ($C_5$-$C_{10}$)heteroaryl, ($C_3$-$C_8$)heterocycloalkyl, or ($C_6$-$C_{10}$)aryl are unsubstituted or substituted.

27. A compound according to claim 1, wherein
$R_{13}$ is H, ($C_1$-$C_6$)alkyl and
$R_{14}$ is H, ($C_1$-$C_6$)alkyl or ($C_3$-$C_8$)cycloalkyl,
wherein ($C_1$-$C_6$)alkyl or ($C_3$-$C_8$)cycloalkyl are unsubstituted or substituted.

28. A compound according to claim 1, wherein $R_{13}$ and $R_{14}$ are H.

29. A compound according to claim 1, wherein $R_6$ is absent or the bicyclic ring system or adamantane formed with $R_6$ is selected from

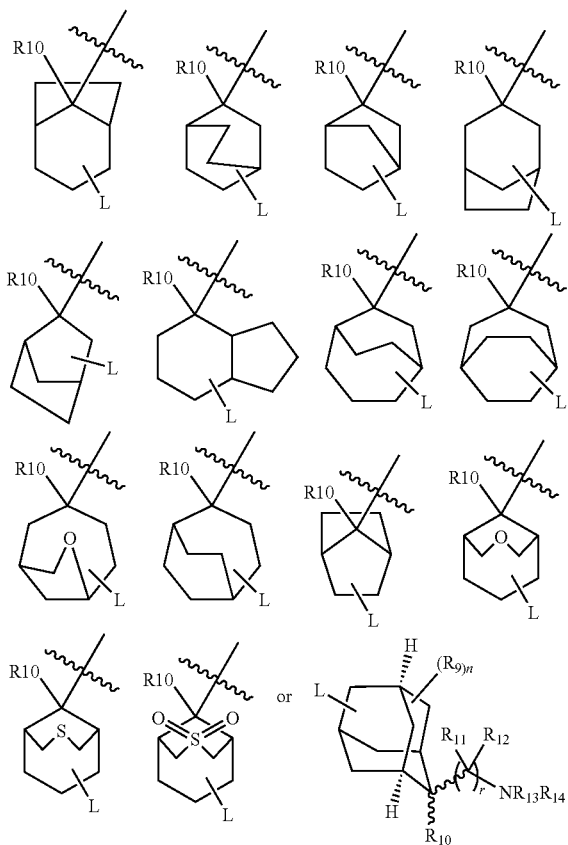

which are unsubstituted or optionally substituted by $R_9$.

30. A compound according to claim 1, wherein $R_6$ is absent.

31. A compound according to claim 1, wherein m is 2 and s is 2.

32. A compound according to claim 1, wherein m is 3 and s is 1.

33. A compound according to claim 1, wherein n is 0, 1, or 2.

34. A compound according to claim 1, wherein n is 0.

35. A compound according to claim 1, wherein r is 1.

36. A compound according to claim 1, wherein L is S($CH_2$)p, S(O)($CH_2$)p, or $SO_2$($CH_2$)p.

37. A compound according to claim 1, wherein L is NH($CH_2$)p or N($C_1$-$C_6$alkyl)-($CH_2$)p.

38. A compound according to claim 1, wherein L is O($CH_2$)p.

39. A compound according to claim 1, wherein p is 0.

40. A compound according to claim 1 selected from the group consisting of
6-[4-(1-Amino-propyl)-4-(tetrahydro-pyran-4-yl)-cyclohexyloxy]-7-chloro-2H-isoquinolin-1-one,
6-[4-(1-Amino-ethyl)-4-ethyl-cyclohexyloxy]-7-chloro-2H-isoquinolin-1-one,
6-[4-(1-Amino-propyl)-4-propyl-cyclohexyloxy]-7-chloro-2H-isoquinolin-1-one,
6-[4-(Amino-cyclopropyl-methyl)-4-propyl-cyclohexyloxy]-7-chloro-2H-isoquinolin-1-one,
6-[4-(1-Amino-propyl)-4-isopropyl-cyclohexyloxy]-7-chloro-2H-isoquinolin-1-one,
6-[4-(1-Amino-ethyl)-4-cyclopropylmethyl-cyclohexyloxy]-7-chloro-2H-isoquinolin-1-one,
6-[4-(1-Amino-propyl)-4-cyclopropylmethyl-cyclohexyloxy]-7-chloro-2H-isoquinolin-1-one,
6-[4-(1-Amino-butyl)-4-cyclopropylmethyl-cyclohexyloxy]-7-chloro-2H-isoquinolin-1-one,
6-[4-(Amino-cyclopropyl-methyl)-4-cyclopropylmethyl-cyclohexyloxy]-7-chloro-2H-isoquinolin-1-one,
6-[4-(1-Amino-2-methyl-propyl)-4-cyclopropylmethyl-cyclohexyloxy]-7-chloro-2H-isoquinolin-1-one,
6-[4-(1-Amino-propyl)-4-isopropoxymethyl-cyclohexyloxy]-7-chloro-2H-isoquinolin-1-one,
6-[4-(1-Amino-ethyl)-4-cyclobutyl-cyclohexyloxy]-7-chloro-2H-isoquinolin-1-one,
6-[4-(1-Amino-propyl)-4-cyclobutyl-cyclohexyloxy]-7-chloro-2H-isoquinolin-1-one,
6-[4-(1-Amino-propyl)-4-cyclopentyl-cyclohexyloxy]-7-chloro-2H-isoquinolin-1-one,
6-[4-(Amino-phenyl-methyl)-4-cyclopentyl-cyclohexyloxy]-7-chloro-2H-isoquinolin-1-one,
6-[4-(1-Amino-propyl)-4-methyl-cyclohexyloxy]-7-chloro-2H-isoquinolin-1-one,
6-[4-(1-Amino-propyl)-4-isobutyl-cyclohexyloxy]-7-chloro-2H-isoquinolin-1-one,
6-[4-(1-Amino-propyl)-4-benzyl-cyclohexyloxy]-7-chloro-2H-isoquinolin-1-one
6-[4-(1-Amino-propyl)-4-ethyl-cyclohexyloxy]-7-chloro-2H-isoquinolin-1-one,
6-[4-(1-Amino-butyl)-4-isopropyl-cyclohexyloxy]-7-chloro-2H-isoquinolin-1-one,
6-[4-(1-Amino-butyl)-4-ethyl-cyclohexyloxy]-7-methyl-2H-isoquinolin-1-one,
6-[4-(1-Amino-ethyl)-4-ethyl-cyclohexyloxy]-7-methyl-2H-isoquinolin-1-one,
6-[4-(1-Amino-propyl)-4-butyl-cyclohexyloxy]-7-chloro-2H-isoquinolin-1-one,
6-[4-(1-Amino-propyl)-4-butyl-cyclohexyloxy]-4-benzyl-7-chloro-2H-isoquinolin-1-one,
6-[4-(1-Amino-2,2,2-trifluoro-ethyl)-4-cyclopropylmethyl-cyclohexyloxy]-7-chloro-2H-isoquinolin-1-one,
6-[4-(1-Amino-2,2,2-trifluoro-ethyl)-4-isopropyl-cyclohexyloxy]-7-chloro-2H-isoquinolin-1-one,
6-[4-(1-Amino-2,2,3,3,3-pentafluoro-propyl)-4-isopropyl-cyclohexyloxy]-7-chloro-2H-isoquinolin-1-one,
6-[4-(Amino-thiazol-2-yl-methyl)-4-isopropyl-cyclohexyloxy]-7-chloro-2H-isoquinolin-1-one, and
6-[4-(Amino-thiazol-5-yl-methyl)-4-isopropyl-cyclohexyloxy]-7-chloro-2H-isoquinolin-1-one, their stereoisomeric and/or tautomeric forms or their pharmaceutically acceptable salts thereof.

41. A compound according to claim 1 selected from the group consisting of cis-6-[4-(1-amino-propyl)-4-(tetrahydropyran-4-yl)-cyclohexyloxy]-7-chloro-2H-isoquinolin-1-one,
cis-6-[4-(1-Amino-propyl)-4-ethyl-cyclohexyloxy]-7-chloro-2H-isoquinolin-1-one,
cis-6-[4-(1-Amino-butyl)-4-isopropyl-cyclohexyloxy]-7-chloro-2H-isoquinolin-1-one,
cis-6-[4-(1-Amino-butyl)-4-ethyl-cyclohexyloxy]-7-methyl-2H-isoquinolin-1-one,
cis-6-[4-(1-Amino-ethyl)-4-ethyl-cyclohexyloxy]-7-methyl-2H-isoquinolin-1-one,
cis-6-[4-(1-Amino-propyl)-4-butyl-cyclohexyloxy]-7-chloro-2H-isoquinolin-1-one, and
cis-6-[4-(1-Amino-propyl)-4-butyl-cyclohexyloxy]-4-benzyl-7-chloro-2H-isoquinolin-1-one,
their stereoisomeric or tautomeric forms and/or pharmaceutically acceptable salts thereof.

42. A compound according to claim 1 selected from the group consisting of cis-6-[4-((S)-1-Amino-propyl)-4-methyl-cyclohexyloxy]-7-chloro-2H-isoquinolin-1-one,
cis-6-[4-((R)-1-Amino-propyl)-4-methyl-cyclohexyloxy]-7-chloro-2H-isoquinolin-1-one,
cis-6-[4-((S)-1-Amino-propyl)-4-(tetrahydro-pyran-4-yl)-cyclohexyloxy]-7-chloro-2H-isoquinolin-1-one,
cis-6-[4-((R)-1-Amino-propyl)-4-(tetrahydro-pyran-4-yl)-cyclohexyloxy]-7-chloro-2H-isoquinolin-1-one,
cis-6-[4-((R)-1-Amino-propyl)-4-ethyl-cyclohexyloxy]-7-chloro-2H-isoquinolin-1-one,
cis-6-[4-((S)-1-Amino-propyl)-4-ethyl-cyclohexyloxy]-7-chloro-2H-isoquinolin-1-one,
cis-6-[4-((S)-Amino-cyclopropyl-methyl)-4-cyclopropylmethyl-cyclohexyloxy]-7-chloro-2H-isoquinolin-1-one, and
cis-6-[4-((R)-Amino-cyclopropyl-methyl)-4-cyclopropylmethyl-cyclohexyloxy]-7-chloro-2H-isoquinolin-1-one,
their tautomeric forms or pharmaceutically acceptable salts thereof.

43. A compound according to claim 1 selected from the group consisting of cis-6-[4-(1-Amino-ethyl)-4-ethyl-cyclohexyloxy]-7-methyl-2H-isoquinolin-1-one,
cis-6-[4-(1-Amino-propyl)-4-ethyl-cyclohexyloxy]-7-fluoro-2H-isoquinolin-1-one,
cis-6-[4-(1-Amino-propyl)-4-ethyl-cyclohexyloxy]-7-fluoro-5-methyl-2H-isoquinolin-1-one,
cis-6-[4-(1-Amino-propyl)-4-ethyl-cyclohexyloxy]-7-methyl-2H-isoquinolin-1-one,
cis-6-[4-(1-Amino-propyl)-4-ethyl-cyclohexyloxy]-5,7-dimethyl-2H-isoquinolin-1-one,
cis-6-[-4-(1-Amino-propyl)-4-methoxy-cyclohexyloxy]-7-chloro-2H-isoquinolin-1-one,
trans-6-[4-(1-Amino-propyl)-4-methoxy-cyclohexyloxy]-7-chloro-2H-isoquinolin-1-one,
6-[4-(1-Amino-propyl)-4-ethoxy-cyclohexyloxy]-7-chloro-2H-isoquinolin-1-one,
cis-6-[4-(Amino-phenyl-methyl)-4-methyl-cyclohexyloxy]-7-chloro-2H-isoquinolin-1-one,
cis-6-[4-(1-Amino-butyl)-4-methyl-cyclohexyloxy]-7-chloro-2H-isoquinolin-1-one,
cis-6-[4-(Amino-phenyl-methyl)-4-cyclopropylmethyl-cyclohexyloxy]-7-chloro-2H-isoquinolin-1-one,
cis-6-[4-(1-Amino-3-methyl-butyl)-4-cyclopropylmethyl-cyclohexyloxy]-7-chloro-2H-isoquinolin-1-one,
cis-6-[4-(1-Amino-2-methyl-propyl)-4-cyclohexyl-cyclohexyloxy]-7-chloro-2H-isoquinolin-1-one,
cis-6-[4-(1-Amino-propyl)-4-(4,4,4-trifluoro-butyl)-cyclohexyloxy]-7-chloro-2H-isoquinolin-1-one,
cis-6-[4-(1-Amino-propyl)-4-(tetrahydro-pyran-4-ylmethyl)-cyclohexyloxy]-7-chloro-2H-isoquinolin-1-one,
cis-6-[4-(Amino-cyclopropyl-methyl)-4-(tetrahydro-pyran-4-ylmethyl)-cyclohexyloxy]-7-chloro-2H-isoquinolin-1-one,
cis-6-[4-(Amino-cyclopropyl-methyl)-4-methyl-cyclohexyloxy]-7-chloro-2H-isoquinolin-1-one,
cis-6-[4-(Amino-cyclopropyl-methyl)-4-ethyl-cyclohexyloxy]-7-chloro-2H-isoquinolin-1-one,
cis-6-[4-(1-Amino-propyl)-4-ethoxymethyl-cyclohexyloxy]-7-chloro-2H-isoquinolin-1-one,
cis-6-[4-(1-Amino-ethyl)-4-cyclopropyl-cyclohexyloxy]-7-chloro-2H-isoquinolin-1-one,
cis-6-[4-(Amino-cyclopropyl-methyl)-4-(4,4,4-trifluoro-butyl)-cyclohexyloxy]-7-chloro-2H-isoquinolin-1-one,
cis-6-[4-(1-Amino-propyl)-4-cyclopropyl-cyclohexyloxy]-7-chloro-2H-isoquinolin-1-one,
cis-6-[4-(Amino-cyclopropyl-methyl)-4-cyclopropyl-cyclohexyloxy]-7-chloro-2H-isoquinolin-1-one,
cis-6-[4-(1-Amino-propyl)-4-(tetrahydro-thiopyran-4-yl)-cyclohexyloxy]-7-chloro-2H-isoquinolin-1-one,
cis-6-[4-(1-Amino-ethyl)-4-propyl-cyclohexyloxy]-7-chloro-2H-isoquinolin-1-one,
cis-6-[4-(1-Amino-ethyl)-4-ethyl-cyclohexyloxy]-7-fluoro-2H-isoquinolin-1-one,
cis-6-[4-(1-Amino-ethyl)-4-ethyl-cyclohexyloxy]-7-fluoro-5-methyl-2H-isoquinolin-1-one,
cis-6-[4-(1-Amino-ethyl)-4-ethyl-cyclohexyloxy]-4-benzyl-7-chloro-2H-isoquinolin-1-one,
cis-7-Chloro-6-{4-[1-(cyclopropylmethyl-amino)-propyl]-4-ethyl-cyclohexyloxy}-2H-isoquinolin-1-one,
cis-6-[4-(1-Benzylamino-propyl)-4-ethyl-cyclohexyloxy]-7-chloro-2H-isoquinolin-1-one,
cis-7-Chloro-6-[4-ethyl-4-(1-isobutylamino-propyl)-cyclohexyloxy]-2H-isoquinolin-1-one,
cis-6-[4-(1-Butylamino-propyl)-4-ethyl-cyclohexyloxy]-7-chloro-2H-isoquinolin-1-one,
6-[4-(1-Amino-2-methyl-propyl)-4-isopropyl-cyclohexyloxy]-7-chloro-2H-isoquinolin-1-one,
cis-6-[4-(1-Amino-propyl)-4-isopropyl-cyclohexyloxy]-7-chloro-4-fluoro-2H-isoquinolin-1-one,
cis-6-[4-(1-Amino-propyl)-4-ethyl-cyclohexyloxy]-7-chloro-4-fluoro-2H-isoquinolin-1-one,
cis-6-[4-(1-Amino-propyl)-4-ethyl-cyclohexyloxy]-4-bromo-7-chloro-2H-isoquinolin-1-one,
cis-6-[4-(1-Amino-propyl)-4-ethyl-cyclohexyloxy]-7-chloro-1-oxo-1,2-dihydro-isoquinoline-4-carbonitrile,
cis-6-[4-(1-Amino-propyl)-4-isopropyl-cyclohexyloxy]-4-bromo-7-chloro-2H-isoquinolin-1-one,
cis-6-[4-(1-amino-2-fluoro-ethyl)-4-ethyl-cyclohexyloxy]-7-chloro-2H-isoquinolin-1-one,
trans-6-[4-(1-amino-2-fluoro-ethyl)-4-ethyl-cyclohexyloxy]-7-chloro-2H-isoquinolin-1-one,
6-[4-(1-amino-3-methoxy-propyl)-4-ethyl-cyclohexyloxy]-7-chloro-2H-isoquinolin-1-one,
cis-6-[4-(1-amino-propyl)-4-(1,1-dioxo-tetrahydrothiopyran-4-yl)-cyclohexyloxy]-7-chloro-2H-isoquinolin-1-one,
6-[3-(1-Amino-propyl)-3-propyl-cyclopentoxy]-7-chloro-2H-isoquinolin-1-one, and
6-[4-(1-Amino-propyl)-4-trifluoromethyl-cyclohexyloxy]-7-chloro-2H-isoquinolin-1-one, their stereoisomeric and/or tautomeric forms or pharmaceutically acceptable salts thereof.

44. A compound according to claim 1 selected from the group consisting of cis1-[4-(5,7-Dimethyl-isoquinolin-6-yloxy)-1-ethyl-cyclohexyl]-propylamine,
cis-1-[1-Ethyl-4-(7-fluoro-isoquinolin-6-yloxy)-cyclohexyl]-propylamine,
cis-1-[1-Ethyl-4-(7-methyl-isoquinolin-6-yloxy)-cyclohexyl]-propylamine,
cis-1-[1-Ethyl-4-(7-fluoro-5-methyl-isoquinolin-6-yloxy)-cyclohexyl]-propylamine,
cis-1-[1-Ethyl-4-(7-fluoro-5-methyl-isoquinolin-6-yloxy)-cyclohexyl]-ethylamine,
cis-1-[4-(7-Bromo-isoquinolin-6-yloxy)-1-ethyl-cyclohexyl]-ethylamine,
cis-1-[4-(7-Methyl-isoquinolin-6-yloxy)-1-ethyl-cyclohexyl]-ethylamine,
cis-1-[4-(5-Chloro-isoquinolin-6-yloxy)-1-ethyl-cyclohexyl]-ethylamine,
cis-6-[4-(1-Amino-ethyl)-4-propyl-cyclohexyloxy]-7-chloro-isoquinolin-1-ylamine, and
[4-(1-Amino-propyl)-4-methyl-cyclohexyl]-isoquinolin-6-yl-amine, and their stereoisomeric and/or tautomeric forms or pharmaceutically acceptable salts thereof.

45. A compound of formula (I) or its pharmaceutically acceptable salt according to claim 1 for use as a medicament.

46. A pharmaceutical composition comprising an effective amount of at least one compound of formula (I) or pharmacologically acceptable salt thereof according to claim 1, pharmaceutically tolerated excipients and carriers and, where appropriate, further additives and/or other active ingredients.

* * * * *